United States Patent [19]

Johnson

[11] 4,206,225
[45] Jun. 3, 1980

[54] 2,10-DISUBSTITUTED DIBENZO[B,D]PYRANS AND BENZO[C]QUINOLINES

[75] Inventor: Michael R. Johnson, Gales Ferry, Conn.

[73] Assignee: Pfizer Inc., New York, N.Y.

[21] Appl. No.: 944,846

[22] Filed: Sep. 22, 1978

[51] Int. Cl.² .................. C07D 215/20; C07D 311/20
[52] U.S. Cl. ................ 424/283; 260/326.34; 260/343.21; 260/345.3; 424/258; 544/126; 544/150; 544/361; 544/375; 546/101; 546/196
[58] Field of Search ............ 260/345.3, 326.34; 546/101, 196; 544/126, 150, 361, 375; 424/258, 283

[56] References Cited

PUBLICATIONS

Ghosh, J. Chem. Soc., p. 1118, (1940).
Russell et al., J. Chem. Soc., p. 169 (1941).

Primary Examiner—Robert Gerstl
Attorney, Agent, or Firm—Connolly and Hutz

[57] ABSTRACT

A compound of the formula

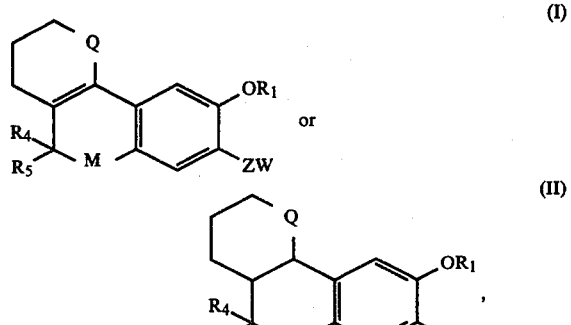

wherein Q is $CH_2$, C=O, CHOH or $CHCH_2OH$; M is O or $NR_6$; where $R_6$ is hydrogen, or certain alkyl, aralkyl, acyl or carboalkoxy substituted alkyl groups; $R_1$ is hydrogen, or certain alkanoyl or amino substituted alkanoyl groups; $R_4$ and $R_5$ are each hydrogen or alkyl having from 1 to 4 carbon atoms; Z is alkylene having from 1 to 9 carbon atoms or $-(alk_1)-X-(alk_2)_n-$ where $(alk_1)$ and $(alk_2)$ are certain alkylene groups and X is O, S, SO or $SO_2$; W is a methyl, phenyl, substituted phenyl, pyridyl, piperidyl, cycloalkyl or substituted cycloalkyl group and the pharmaceutically acceptable and addition salts of said compounds having a basic nitrogen atoms. Said compounds are useful as analgesics and as intermediates therefore.

35 Claims, No Drawings

2,10-DISUBSTITUTED DIBENZO[B,D]PYRANS AND BENZO[C]QUINOLINES

BACKGROUND OF THE INVENTION

1. Field of the Invention

This invention relates to 7,8,9,10-tetrahydro-2-hydroxy-3-substituted-dibenzo[b,d]pyrans, corresponding 6,7,8,9,10,10a-hexahydrodibenzo[b,d]pyrans, 5,6,7,8,9,10-hexahydro-2-hydroxy-3-substituted-benzo[c]quinolines, 5,6,6a,7,8,9,10,10a-octahydro-benzo[c]quinolines and derivatives thereof of the formula (I) and (II) all of which are useful as analgesics in mammals, including man. Some of the compounds of formula (I) and (II) are also useful as tranquilizers or diuretics in mammals, including man and as intermediates.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesic agent such as d-propoxyphene, codeine, and morphine possess addictive liability. The need for improved and potent analgesic agents is, therefore, evident.

The CNS active dibenzo[b,d]pyrans disclosed in the prior art are 1-hydroxy-9-substituted compounds closely related in structure to the naturally occurring dibenzo[b,d]pyrans. See, for example, the following review articles: R, Mechoulam, Editor, "Marijuana, Chemistry, Pharmacology, Metabolism and Clinical Effects," Academic Press, New York, N.Y., 1973; Mechoulam, et. al., *Chemical Reviews*, 76, 75–112 (1976). In addition, rather comprehensive reviews are set forth in U.S. Pat. No. 3,886,184 and U.S. Pat. No. 3,968,125.

U.S. Pat. Nos. 3,507,885 and 3,363,058, issued Apr. 21, 1970 and Jan. 18, 1972, respectively, describe various 1-hydroxy-3-alkyl-6H-dibenzo[b,d]pyrans having at the 9-position substituents such as: oxo, hydrocarbyl and hydroxy or chloro, hydrocarbylidene, and intermediates therefor.

Hoops et al., *J. Org. Chem.*, 33, 2995–2996 (1968) describe the preparation of the 5-aza analog of $\Delta^{6a(10A)}$-tetrahydrocannabinol referred to therein as 7,8,9,10-tetrahydro-1-hydroxy-5,6,6,9-tetramethyl-3-n-pentyl-phenanthridine, but report no utility for the compound. Beil, in "Pyschomimetic Drugs", edited by Efron, Raven Press, New York, 1970, page 336, reports the compound was "completely inert in animal pharmacology."

Hardman et al., *Proc. West. Pharmacol. Soc.* 14, 14–20 (1971) reports some pharmacological activity for 7,8,9,10-tetrahydro-1-hydroxy-6,6,9-trimethyl-3-n-pentyl phenanthridine, a 5-aza $\Delta^{6a(10a)}$-tetrahydrocannabinol.

The only known 2-hydroxy-isomer of tetrahydrocannabinol is 6,7,8,9-tetrahydro-2-hydroxy-3-n-amyl-6,6,9-trimethyldibenzo[b,d]pyran prepared by Russell et al., *J. Chem. Soc.*, 169 (1941). It was found to be inactive at does of 20 mg./kg. in rabbits.

Mechoulam and Edery in "Marijuana", edited by Mechoulam, Academic Press, New York, 1973 page 127, observe that major structural changes in the tetrahydrocannabinol molecule seem to result in steep reductions in anagesic activity.

Paton, In *Annual Review of Pharmacology*, 15, 192 (1975) presents generalizations on structure-action relationships among canabinoids. The presence of the gem dimethyl group in the pyran ring is critical for cannabinoid activity and substitution of N for O in the pyran ring removes activity.

SUMMARY OF THE INVENTION

The present invention relates to certain 2-hydroxydibenzo[b,d]pyrans and 2-hydroxybenzo[c]quinolines all of which are useful analgesic agents in mammals, including man, and some of which are also useful as tranquilizing agents or diurectic agents in mammals, including man, and as intermediates for preparing other compounds of the invention. These compounds are of the formulae

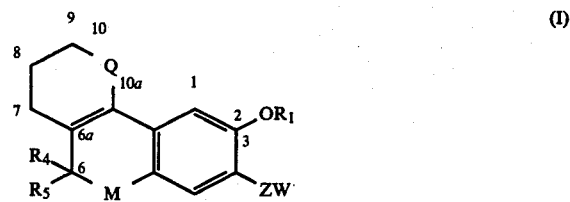

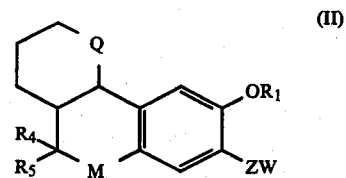

where

Q is a member selected from the group consisting of $CH_2$, $C=O$, $CHOH$ and $CHCH_2OH$;

M is O or $NR_6$ wherein $R_6$ is a member selected from the group consisting of hydrogen, $-(CH_2)_y$-carboalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms, $C_6H_5-(CH_2)_x-$ wherein x is an integer from one to four and $C_6H_5-(CH_2)_{x-1}-CO-$;

$R_1$ is hydrogen, alkanoyl having from one to five carbon atoms or $-CO-(CH_2)_p-NR_2R_3$ wherein p is 0 or an integer from 1 to 4; each of $R_2$ and $R_3$ when taken individually is hydrogen or alkyl having from one to four carbon atoms; $R_2$ and $R_3$ when taken together with the nitrogen to which they are attached form a 5- or 6-membered heterocyclic ring selected from piperidino, pyrrolo, pyrrolidino, morpholino and N-alkylpiperazino having from one to four carbon atoms in the alkyl group;

each of $R_4$ and $R_5$ is hydrogen, or unbranched alkyl having from one to four carbon atoms;

Z is (a) alkylene having from one to nine carbon atoms;

(b) $-(alk_1)_m-X-(alk_2)_n-$ wherein each of $(alk_1)$ and $(alk_2)$ is alkylene having from one to nine carbon atoms, with the proviso that the summation of carbon atoms in $(alk_1)$ plus $(alk_2)$ is not greater than nine;

each of m and n is 0 or 1;

X is O, S, SO or $SO_2$;

W is methyl, phenyl, p-chlorophenyl, p-fluorophenyl, pyridyl, piperidyl, cycloalkyl having from three to seven carbon atoms, or monosubstituted cycloalkyl wherein the substituent is phenyl, p-chlorophenyl or p-fluorophenyl; with the proviso that when W is methyl, Z is $-(alk_1)_m-X-(alk_2)_n-$ and the pharmaceutically acceptable acid addition salts of said compound which contain a basis group. In compounds where two or more basic groups are present, such as those wherein M is $-NH$, W is pyridyl and/or $R_1$ represents a basic ester moiety, polyaddition salts of said acids are included in the invention.

Compounds having the formula (II) above contain assymetric centers at the 6a- and 10a-positions. For both compounds (I) and (II) above there may be additional assymetric centers in the $R_1$ substituent, at the 3-position substituent (-ZW), and the 5-, 6- and 10-positions. For convenience, the above formulae depict the racemic compounds. However, the above formulae are considered to be generic to and embracive of the racemic modifications of the compounds of this invention, the diastereomeric mixture, the pure enantiomeres and diastereomers thereof. The utility of the racemic mixtures, the diastereomeric mixtures as well as of the pure enantiomers and diastereomers is determined by the biological evaluations described below.

In addition to being useful CNS agents of the invention, certain compounds included herein are especially valuable as intermediates useful in providing other compounds of the invention. Said intermediates are those compounds of formula (I) and (II) wherein $R_1$ is hydrogen, $R_4$, $R_5$, Z and W are as previously defined and
(a) for those of formula (I):
  i. M is O and Q is C=O or $CH_2$;
  ii. M is $NR_6$ where $R_6$ is hydrogen or alkyl having from one to six carbon atoms and Q is C=O or $CH_2$;
(b) for those of formula (II):
  i. M is O and Q is C=O;
  ii. M is $NR_6$ where $R_6$ is hydrogen or alkyl having from one to six carbon atoms and Q is C=O.

Especially valuable analgesic agents of the invention are the compounds of formula (I) wherein $R_1$ is hydrogen, Z is $CH(CH_3)CH_2CH_2CH_2$, W is phenyl, $R_4$ and $R_5$ are each methyl, M is O and Q is $CH_2$ or CHOH wherein said hydroxy group in Q is in the α-confirguration.

Further especially valuable analgesic agents of the invention are compounds of formula (II) wherein $R_1$ is hydrogen, Z is $CH(CH_3)CH_2CH_2CH_2$, W is phenyl, $R_4$ and $R_5$ are each methyl, M is O, the hydrogen atoms in the 6a- and 10a-positions are in a cis-relationship and Q is C=O or CHOH.

A further object of the invention is to provide a process for producing analgesia in a mammal which comprises orally or parenterally administering to the mammal an analgesic producing quantity of a compound of formula (I) or (II).

A still further object of the invention is to provide a pharmaceutical composition active as an analgesic comprising a pharmaceutically acceptable carrier and an analgesia producing amount of a compound of formula (I) and (II).

DETAILED DESCRIPTION OF THE INVENTION

The compounds of the invention of formula I and II are prepared as shown in Flow Sheets A through E, below. The preparation of the 6a,10a-unsaturated-dibenzo[b,d]-pyran-10-ones of formula (IX) wherein $R_4$ and $R_5$ are the same prepared as shown in Flow Sheet A. The WZ-substituted hydroquinones of formula (III) where W and Z are as previously defined are reacted with an alkyl ester of 2-oxalyl adipic acid (IV) where $R_7$ is preferably alkyl having from one to four carbon atoms and methyl or ethyl are especially preferred. The reaction is carried out in the presence of an equimolar amount of a condensing agent, preferably phosphorous oxychloride. While temperatures of from about 0° to 50° C. may be employed, the use of room temperature is preferred for reasons of convenience at which temperature the reaction is ordinarily complete within five to ten days. The reaction mixture is then taken up in a water immiscible organic solvent, such as, for example, chloroform, methylene, chloride, benzene, or 1,2-dichloroethane, washed with water and isolated and purified by means well known to one skilled in the art to obtain the 2-oxo-benzopyran diester intermediate of formula (V) wherein $R_7$, W and Z are as defined above.

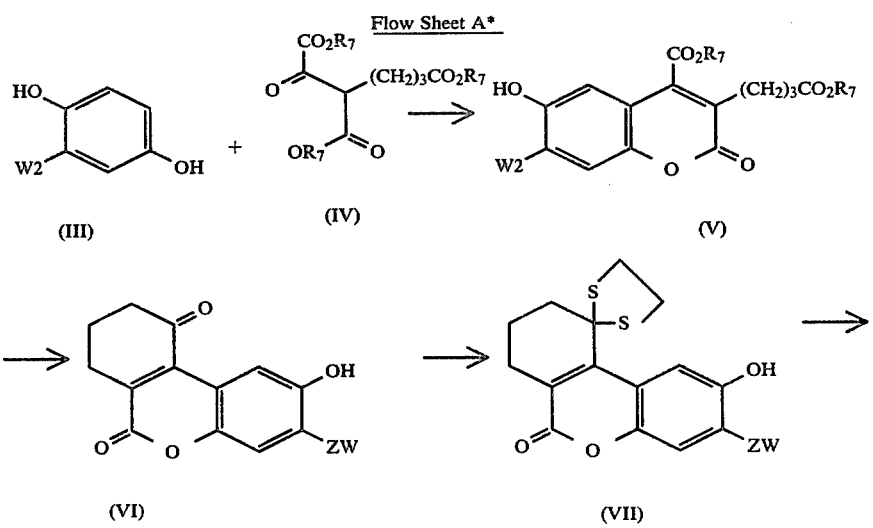

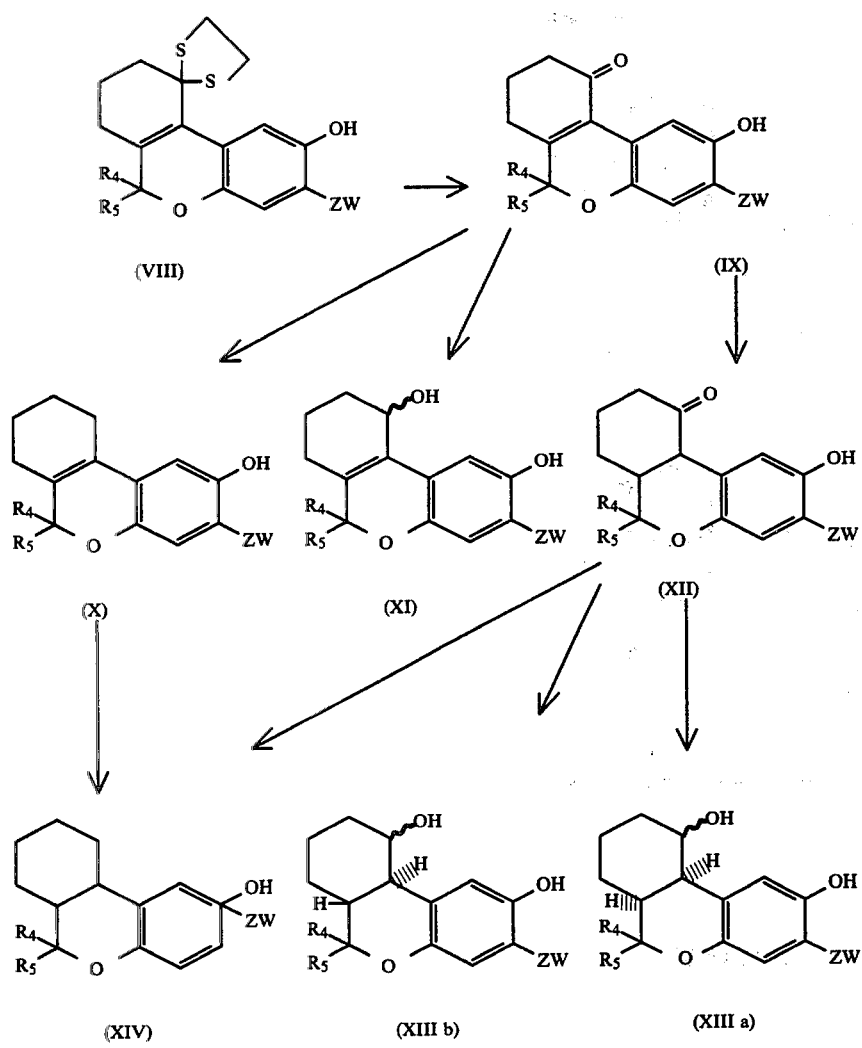
(XIV)
$R_4$ and $R_5$ are the same.
Flow Sheet B
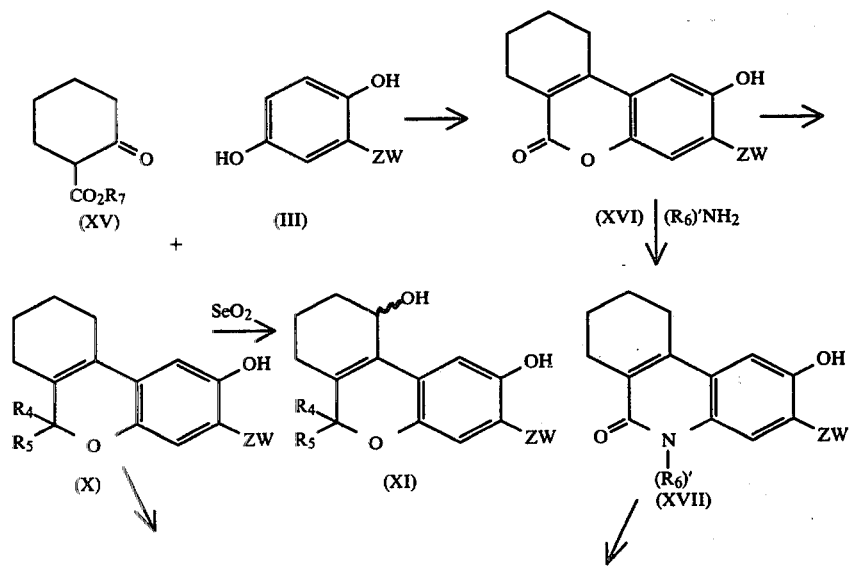

-continued
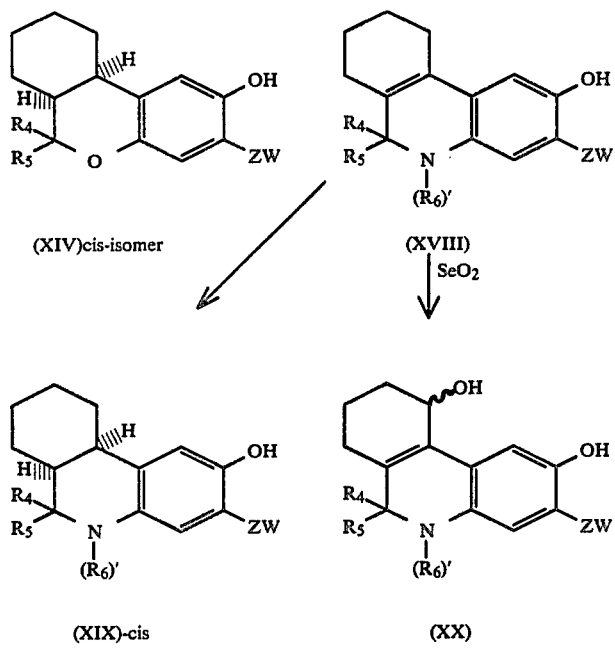
*(R₆)' is hydrogen or alkyl having from one to six carbon atoms, R₄ and R₅ are the same.
Flow Sheet C*
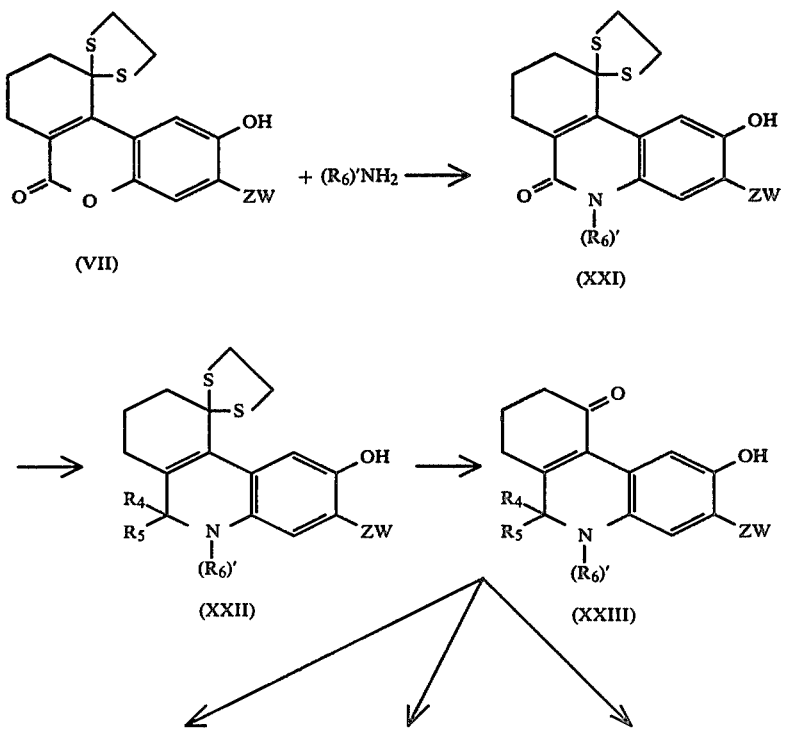

-continued
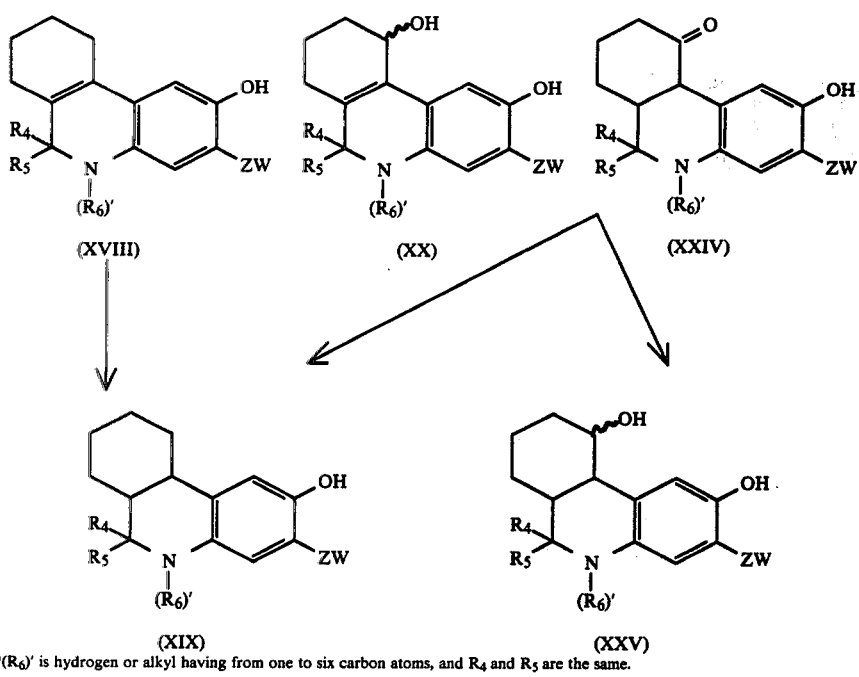
*(R$_6$)' is hydrogen or alkyl having from one to six carbon atoms, and R$_4$ and R$_5$ are the same.
Flow Sheet D*
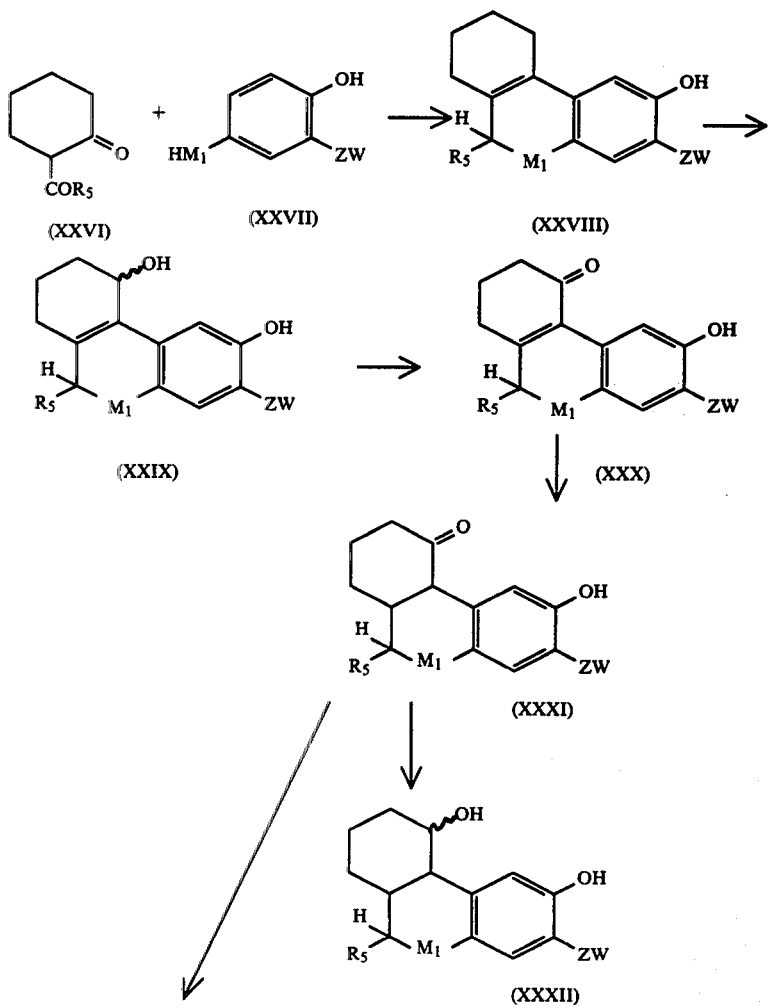

(XXVIII) → 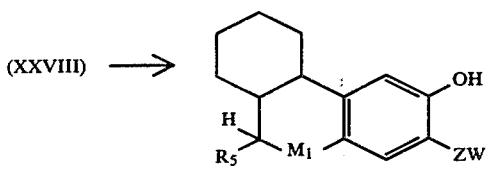

(XXXIII)

*M$_1$ is —O— or —NH—, R$_5$ is alkyl as previously defined.

Flow Sheet E

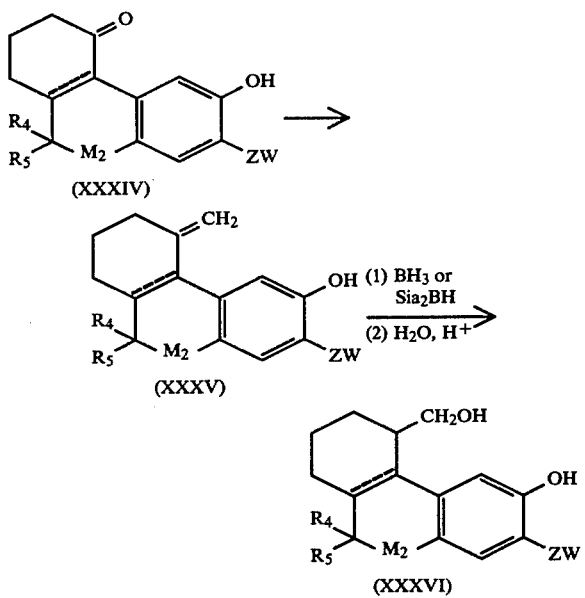

Sia$_2$BH is di-sec-isoamylborane, see Hoffsommer et. al., J. Org. Chem., 28, 1751 (1963).

M$_2$ is —O— or N(R$_6$)' where (R$_6$)' is hydrogen or alkyl having from one to six carbon atoms.

The diester intermediate (V) is then reacted under the base catalyzed intramolecular cyclization conditions of the well known Dieckmann Reaction (see e.g., House, "Modern Synthetic Reactions" W. A. Benjamin, Menlo Park, California, 1972, p. 740) and the reaction mixture hydrolyzed and decarboxylated under acidic hydrolysis conditions to obtain the 2-oxodibenzo[b,d]pyrans of formula (VI) wherein Z and W are as preiously defined. The cyclization is carried out in the presence of a reaction inert organic solvent, for example, benzene, toluene, xylene, diethylether, tetrahydrofuran or the like. Preferred as base for the reaction are the alkali metal alkoxides of alkanols having from one to four carbon atoms and especially preferred are sodium methoxide or sodium ethoxide. A two to twenty fold molar excess of such base is ordinarly employed. The diester of formula (V) is typically added in portions to the mixture of said base and solvent and the resulting mixture allowed to react at a temperature of from room temperature up to the reflux temperature of the solvent. The latter temperature being preferred because the reaction is substantially complete within a shorter time at the higher temperature. Typically, when benzene is employed as solvent and the reaction is carried out at room temperature, the cyclization step is complete within one to three hours. The reaction mixture is then acidified with strong acid, preferably hydrochloric or sulfuric acid in the presence of water and the organic layer separated and isolated by well known methods. The isolate is then subjected to acid hydrolysis conditions, preferably by refluxing the isolate in a mixture of hydrochloric acid and acetic acid until hydrolysis and decarboxylation are complete, usually within one hour. The desired intermediate of formula (VI) is then isolated and purified by methods well known in the art.

In order to obtain the desired dibenzo[b,d]pyrans of formula (IX) wherein R$_4$ and R$_5$ are the same and are hydrogen or unbranched alkyl having from one to four carbon atoms, it is preferred to protect the 10-oxo group of the intermediates (VI) prior to introduction of the R$_4$ and R$_5$ substituents. While such protection may be accomplished by converting the 10-oxo group of said compounds (VI) to a ketal or thioketal employing any of the alcohols or thiols known in the art to form such ketal or thioketal groups, it has been found that the use of the 1,2-ethanedithiol to provide the corresponding dithioethylene ketals of formula (VII) are preferred since they are smoothly reacted with a metal hydride or Grignard reagent to afford the 6,6-disubstituted derivatives of formula (VIII) with minimal side reaction. The compounds of formula (VI) are converted to the 10-(1,2-dithioethylene)ketals of formula (VII) by methods well known in the art and as illustrated in the examples. Said dithioketals (VII) may then be reacted smoothly to form the compounds of formula (VIII) wherein R$_4$ and R$_5$ are the same and are hydrogen or unbranched alkyl having from one to four carbon atoms.

When said compounds (VIII) are desired wherein R$_4$ and R$_5$ are each hydrogen, the intermediate (VII) is reacted by methods known to selectively reduce a lactone carbonyl group to a methylene group. Examples of such methods are the use of borane-tetrahydrofuran complex [see, e.g. Pettit et al., J. Org. Chem. 26, 4557 (1961)] and the well known reduction by means of lithium aluminum hydride. The latter method is preferred for reasons of efficiency and convenience. The preferred method of reduction with lithium aluminum hydride is carried out in the presence of ethereal solvent such as diethyl ether or tetrahydrofuran employing a stoichiometric excess of the hydride reagent and at a temperature of from about 20° up to the reflux temperature of the solvent. The desired product of formula (VIII) wherein R$_4$ and R$_5$ are each hydrogen and Z and W are as defined above are isolated and purified by well known methods.

The compounds of formula (VIII) wherein R$_4$ and R$_5$ are the same and are each unbranched alkyl are obtained by reaction of a Grignard reagent, R$_4$ Mg X (X=Cl, Br, I), with the intermediate of formula (VII). The reaction is carried out under conditions known in the art for analogous reactions with 1,3-disubstituted dibenzopyrones to obtain 6,6-dimethyldibenzopyrans, see e.g., Adams, et al., J. Amer. Chem. Soc. 62, 2201 (1940). Typically, a large excess of Grignard reagent is added slowly to an ethereal solution of the intermediate (VII) under anhydrous conditions, the resulting mexture is heated at the reflux temperature of the solvent for a few days and the reaction mixture treated with dilute hydrochloric acid in the cold to decompose the intermediate and excess reagent. The product of formula (VIII) is then isolated by well known methods. A preferred solvent is diethylether.

The intermediate (VIII) wherein $R_4$ and $R_5$ are the same and are hydrogen or alkyl as defined above is then further reacted to remove the 1,2-ethylenedithio protecting group. This is typically carried out in aqueous acetone and in the presence of mercuric chloride and cadmium carbonate. The deprotection is ordinarily effected at room temperature, the reaction being substantially complete in about 10 to 50 hours. The desired products of formula (IX) are isolated and may be purified, if desired, by methods well known to one skilled in the art and as set forth in the examples.

The $\Delta^{6a,10a}$-10-oxo-compounds of formula (IX) are valuable CNS agents of the invention, they are also valuable as intermediates for preparation of other useful CNS agents of the invention as shown in Flow Sheet A.

The conversion of said compounds of formula (IX) to compounds of formula (X) or (I) wherein Q is $CH_2$ and M is O, is accomplished by employing the well known Wolff-Kishner reduction, see e.g., Todd, *Organic Reactions,* 4, 378 (1948). The reaction is carried out in the presence of an organic solvent, preferably diethylene glycol, the intermediate (IX), and a base, preferably potassium hydroxide or, sodium hydroxide, and hydrazine are combined, the mixture is warmed cautiously until no longer exothermic, then heated at the reflux temperature of the solvent, typically for a few hours. The bulk of the solvent is then distilled off and the residue heated at 190°–205° C. for several hours and the product of formula (X) isolated by well known methods. As shown below, the products (X) are also obtained by an alternative method.

The $\Delta^{6,10a}$-unsaturated-10-hydroxy compounds of formula (XI) are provided by reduction of the corresponding compounds of formula (IX) employed reagents known to selectively reduce $\alpha,\beta$-unsaturated ketones to allyic alcohols. Examples of such reagents are sodium borohydride, potassium borohydride, sodium cyanoborohydride and lithium aluminum hydride. A preferred reagent is sodium borohydride for reasons of economy and efficiency. The reduction is carried out employing a stoichiometric excess of sodium borohydride in the presence of a reaction inert solvent and at a temperature of from about $-20°$ to 50° C., preferably 0°–25° C. Examples of suitable reaction inert solvents are the lower alkanols such as methanol, ethanol and isobutanol, ethers such as diethyl ether and 1,2-dimethyoxyethane and their mixtures with water. Preferred such solvents are methanol and ethanol.

The products of formula (XI) are isolated by methods well known in the art. The reduction affords a mixture of $10\alpha$-ol and $10\beta$-ol isomers of formula (XI) which may be separated, if desired, by methods known in the art to separate such mixtures. A preferred method for such separation is by means of silica gel column chromatography.

Reduction of the compounds of formula (IX) with lithium metal in anhydrous ammonia affords mixture of 6a,10a-cis and 6a,10a-trans isomers of formula (XII). The reaction is preferably carried out in the presence of a large excess of ammonia and the presence of a reaction inert organic solvent, for example diethyl ether, tetrahydrofuran or 1,2-dimethoxyethane. A preferred solvent is tetrahydrofuran. A large excess of lithium metal, ammonia, said solvent and reactant of formula (IX) are combined and reacted under anhydrous conditions at a temperature of from about $-100°$ to $-40°$ C. at which temperature the reduction is ordinarily completed within 30 minutes. The excess of lithium is decomposed by addition of ammonium chloride, the ammonia evaporated and the product isolated by standard methods known in the art. The mixture of cis and trans isomers is separted, if desired, by means of column chromatography, on silica gel, for example.

The mixture of cis and trans isomers of formula (XII) may be further reduced to provide the corresponding 10-hydroxy compounds of formula (XIII). This reduction is accomplished by employing any of the reagents and conditions known to reduce ketones to alcohols. Examples of such reagents and conditions are catalytic hydrogenation over metal or metal oxide catalysts such as, for example, those of platinum, rhodium, nickel and the like; reduction with metal hydrides such as, for example, sodium borohydide, lithium aluminum hydride or sodium cyanoborohydride. A referred method for reduction of compounds of formula (XII) to obtain products of formula (XIII) is by means of sodium borohydride employing conditions as set forth above for similar reduction of compounds (IX) to products of formula (XI).

Prior to carrying out said reduction of compounds (XII) it is desirable to separate the cis and trans mixture of compounds (XII) in order to obtain a reaction product of the 6a,10a-cis-configuration (XIIIa) or 6a, 10a-trans-configuration (XIIIb), each of which is more readily separated to provide the corresponding $10\alpha$-ol and $10\beta$-ol compounds. Without prior separation of the cis, trans-mixture of formula (XII) a four component reaction mixture is obtained which is considerably more difficult to separate.

The compounds of formula (XIV) or (II) wherein Q is $CH_2$ and M is O, are obtained from the above described products of formula (X) or (XII) by reduction techniques.

Employing a compound of formula (X) as starting material, the corresponding 6a,10a-cis-compound of formula (XIV) is obtained by any of the method known in the art for catalytic, cis-hydrogenation of alkenes. Examples of catalysts which may be employed for such hydrogenation are palladium, platinum, rhodium, nickel and the metal oxides and salts thereof. A preferred catalyst is palladium. The hydrogenation is carried out in the presence of a reaction inert organic solvent, preferably an alkanol having from one to four carbon atoms. The reduction and isolation of desired cis-isomer of formula (XIV) are carried out by methods well known in the art, see, e.g., Friefelder, "Practical Catalytic Hydrogenation, Techniques and Applications," Wiley and Sons, Inc., New York, 1971.

As mentioned above, the compounds of formula (XIV) are also obtained by reduction of the compounds (XII). In this case the reduction is accomplished by means of hydrazine and base by the Wolff-Kishner reduction as described above for the preparation of compounds of formula (X). This reduction can be carried out on purified cis-isomer of formula (XII) to provide cis-(XIV), the trans-isomer of formula (XII) to provide trans-(XIV), or on the mixture of isomers to provide the corresponding mixed isomers of formula (XIV).

An alternate method for preparation of certain dibenzo[b,d]pyrans of the invention is set forth in Flow Sheet B. A ZW-substituted hydroquinone of formula (III) wherein Z and W are previously described, is reacted with a 2-oxocyclohexane carboxylic acid ester of formula (XV), wherein $R_7$ is as defined above, to provide an intermediate of formula (XVI). The reaction is carried out and product isolated as described above for the preparation of benzopyrones of formula (V).

The intermediate (XVI) is further reacted with a metal hydride, preferably lithium aluminum hydride or a Grignard reagent as described above for the preparation of compounds of formula (VIII) to provide the desired compound (X) directly, wherein $R_4$ and $R_5$ are the same and are hydrogen or unbranched alkyl having from one to four carbon atoms.

The compounds of the invention of formula (X) are valuable as CNS agents and as intermediates for providing the CNS agents of the invention of formula (XI) and (XIV). The cis-compounds (XIV) are obtained from compounds of formula (X) by methods known in the art for the cis-hydrogenation of alkenes employing metal catalysts as described above.

An alternate method for preparation of compounds of formula (XI) is carried out by oxidation of compounds of formula (X) with selenium dioxide or selenious acid. The reaction is carried out in the presence of a reaction inert organic solvent, for example, ethanol, dioxane, 1,2-dimethoxyethane or acetic acid, a preferred solvent is dioxane. The reaction is carried out at a temperature of from about 0° C. up to the reflux temperature of the solvent, a preferred temperature is room temperature for reasons of convenience and improved selectivity over higher reaction temperatures. At room temperature the reaction is substantially complete in from one to three weeks. The product is isolated and purified by standard methods known to those skilled in the art, see, for example, Fieser et al., "Reagents for Organic Synthesis," John Wiley and Sons, Inc., New York, 1967, Vol. I, p. 992, and references cited therein. The resulting mixture of $10\alpha$-ol and $10\beta$-ol compounds of formula (XI) are readily separated, for example, by silica gel column chromatography.

As indicated in Flow Sheets B and C pyrones of formulae (XVI) and (VII) may also be reacted with ammonia or primary amines to provide the corresponding 6-oxo-benzo[c]quinolines of formulae (XVII) and (XXI) which are further reacted to provide the valuable benzo[c]quinolines of the invention of formulae (I) and (II) wherein $R_4$ and $R_5$ are the same and M is $N(R_6)'$ where $(R_6)'$ is hydrogen or alkyl having form one to six carbon atoms.

The reaction of the pyrones with ammonia or amines to provide the 6-oxo-benzo[c]quinolines of formulae (XVII) and (XXI) is carried out essentially by the methods of Hoops et al. *J. Org. Chem.*, 33, 2995 (1968) and Kraatz et al., *Chemische Berichte,* 106, 62 (1973).

The pyrone and excess ammonia or amine are combined and heated under pressure in the presence of water or organic solvent. When the reation is substantially complete, the reaction mixture is cooled, acidified and the product of formulae (XVII) or (XXI) isolated by known methods. While the reaction may be carried out with ammonia and a wide variety of primary amines including alkyl, alkenyl, aralkyl and cycloalkyl primary amines, preferred such reactants are those of the formula $(R_6)'$—$NH_2$ wherein $(R_6)'$ is hydrogen and alky having from one to six carbon atoms. Although the reaction may be carried out successfully in the presence of equimolar amounts of pyrone and reactant $(R_6)'NH_2$, excess of the latter, up to 50 moles per mole of said pyrone, are preferred. Typically, the reaction is carried out in standard pressure reactors such as an autoclave or sealed glass tube at elevated temperature. A preferred temperature is from about 100° to 250° C., especially 150° to 200° C.

The 6-oxo-benzo[c]quinolines (XVII) and (XXI) are then reacted with metal hydrides or Grignard reagents, by methods previously described for the preparation of the corresponding dibenzopyrans (VIII) and (X), to provide the products of formulae (XVIII) and (XXII) wherein $R_4$ and $R_5$ are the same and $R_4$, $R_5$, $(R_6)'$, Z and W are as previously defined.

The compounds of formula XVIII are valuable pharmaceuticals of the invention as well as being valuable intermediates which may be employed to provide compounds of formula (XIX) wherein the 6a,10a hydrogens are in a cis-relationship to each other by methods described above for cis-hydrogenation of a carbon-carbon double bond and to provide the corresponding 10-hydroxy compounds of formula (XX) by selenium dioxide or selenious acid oxidation also as described above.

The dithioketal intermediates (XXII) are hydrolyzed as described above for compounds of formula (VIII) to provide the valuable 6a,10a-unsaturated-10-oxo-benzo[c]quinolines of formula (XXIII) which are valuable pharmaceuticals of the invention as well as being valuable intermediates. As intermediates, the compounds (XXIII) undergo the same reactions, employing the same reagents and conditions as previously described for the corresponding dibenzopyran products derived from intermediate (IX). Such valuable products derived from intermediate (XXIII) are those of the formulae (XVIII), (XIX), (XX), (XXIV) and (XXV) as shown in Flow Sheet C.

Compounds of the invention of formulae (I) and (II) wherein $R_4$ is hydrogen and $R_5$ is unbranched alkyl having from one to four carbon atoms are obtained by methods outlined in Flow Sheet D. 2-Alkylcarbonylcyclohexanones of formula (XXVI), wherein $R_5$ is as previously defined, are condensed with ZW-substituted hydroquinones or ZW-substituted p-aminophenols of formula (XXVII) wherein $M_1$ is an oxygen atom or —NH— to provide the compounds of the invention of formula (XXVIII).

Approximately equimolar amounts of reactants of formula (XXVI) and (XXVII) are contacted in the presence of organic solvent at a temperature of from about 0° to 50° C., preferably 10° to 30° C. An anhydrous acid, preferably hydrogen chloride, is added in excess, and the resulting acid mixture is held at a temperature in the above range, typically for 2 to 8 days. The mixture is neutralized and treated with at least a stoichiometric amount of sodium cyanoborohydride in the presence of organic solvent to selectively effect reduction and thus provide the desired dibenzopyrans or benzo[c]quinolines of the formula (XXVIII) which are isolated and purified by methods known to one skilled in the art and as exemplified herein. For the initial phase of this procedure under acidic conditions, examples of suitable solvents are organic acids such as formic, acetic, propionic and isobutyric acids; alkanols such as methanol, ethanol, isopropanol, butanol and isoamyl alcohol; ethers such as tetrahydrofuran, dimethoxyethane and diethyleneglycol dimethylether; dimethylformamide and dimethylsulfoxide. A particularly preferred solvent is glacial acetic acid. For the reduction phase with sodium cyanoborohydride examples of suitable solvents are the same as for the first phase, excepting the above-mentioned acids. Preferred solvents for the reduction are the lower alkanols having from one to four carbon atoms, and methanol is especially preferred.

The compounds of formula (XXVIII) are valuable as CNS agents of the invention and as intermediates for the preparation of compounds (XXIX) through (XXXIII) of the invention as shown in Flow Sheet D. The conversion of compounds (XXVIII) to 10-hydroxy compounds (XXIX) is effected by selenium dioxide or selenious acid oxidation employing methods and conditions described above for the preparation of compounds of formula (XI). The 6a,10a-unsaturated-10-keto compounds of formula (XXX) are provided by oxidation of compounds of formula (XXIX). This oxidation is effected by a variety of oxidizing agents and conditions known in the art for oxidizing $\alpha,\beta$-unsaturated secondary alcohols to the corresponding $\alpha,\beta$-unsaturated ketones. Examples of such oxidizing agents are mixtures of alkali metal dichromate salts and sulfuric acid, chromic acid and sulfuric acid, chromic anhydride in acetic acid, chromic acid-pyridine complex and manganese dioxide, see e.g., Fieser, "Reagents for Organic Synthesis," Wiley and Sons, Inc., New York, 1967. A particularly preferred method employs chromic anhydride and sulfuric acid in acetone as solvent. Equimolar amounts of chromic anhydride and alcohol of formula (XXIX) are contacted in the presence of acetone at a temperature of from about $-20°$ to $30°$ C., typically at $-10°$ C. and in a dry oxygen free atmosphere, e.g. a nitrogen atmosphere. After from a few minutes, up to about one hour, under these conditions the reaction mixture is poured onto water and the product of formula (XXX) isolated by known methods.

The compounds of formula (XXX) undergo further reaction, as shown in Flow Sheet D, by employing the same methods and conditions previously described for the analogous compounds of formula (IX). Thus, lithium, ammonia reduction of compounds (XXX) provides the ketones of formula (XXXI) which, in turn, may be reduced with, e.g., sodium borohydride to provide the 10-hydroxy compounds of formula (XXXII). Alternatively, compounds (XXXI) may be reduced under the Wolff-Kishner conditions described above, to provide the compounds of formula (XXXIII). However, the latter compounds are more efficiently produced by catalytic hydrogenation of the above described intermediates of formula (XXVIII) by methods which have also been described above, for example, for the preparation of the compounds of formula (XIV).

The valuable CNS agents of the invention of the formulae (IX), (XII), (XXIII), (XXIV), (XXX) and (XXXI), all of which are 10-oxo-or 6a,10a-unsaturated-10-oxo compounds, are all represented by the formula (XXXIV) in which the broken line represents either a bond or no bond, $R_4$ $R_5$, Z and W are as previously defined and $M_2$ is $-O-$ or $N(R_6)'$ where $(R_6)'$ is hydrogen or alkyl having from one to six carbon atoms. The compounds denoted by the formula (XXXIV) and (XXXV) all serve as intermediates for the preparation of the CNS agents of the invention of the formula (XXXVI), wherein $R_4$, $R_5$, $M_2$, Z and W are as defined above.

As shown in Flow Sheet E the compounds of the invention of formula (XXXIV) are first converted to the 10-methylene intermediates of formula (XXXV) by reaction with methylene triphenylphosphine ylid, the so called Wittig reagent, see e.g., Fieser, loc. cit., p. 1238 and reference cited therein. In a typical reaction a molar excess of ylid is generated from methyl triphenylphosphonium bromide, dimethylsulfoxide, which also serves as solvent, and sodium hydride, the compound of formula (XXXIV) is added and the mixture heated at about $65°$ C. until the reaction is substantially complete. The mixture is then poured into ice/water, isolated and purified by standard methods known to one skilled in the art to obtain the intermediate 10-methylene intermediates of formula (XXXV).

The intermediates of formula (XXXV) are converted to the corresponding 10-hydroxymethylene products of formula (XXXVI) by hydroboration of the 10-methylene group, see for example, Zweifel and Brown, *Organic Reactions*, 13, 1 (1963); and Hoffsommer et al., *J. Org. Chem.*, 28, 1751 (1963).

First the intermediate (XXXV) is contacted with borane, diborane or a dialkylborane, said alkyl having from one to eight carbon atoms, in the presence of a reaction inert organic solvent under anhydrous conditions. This step is carried out at a temperature of from about $-20°$ to $50°$ C., preferably at $-5°$ to $30°$ C. to form a boron-containing intermediate. The excess of borane reagent is then decomposed and the mixture oxidized with alkaline hydrogen peroxide at a temperature of from about $-20°$ to $50°$ C., preferably at about room temperature. In a typical reaction approximately equimolar amounts of borane or said dialkylborane are contacted in tetrahydrofuran as solvent at about $0°$ C. and the mixture stirred overnight at room temperature. Water is added to decompose the excess borane reagent. The mixture is then treated with sodium acetate solution and hydrogen peroxide, stirred for 24 hours, poured onto ice and the 10-hydroxymethylene compound is isolated by known methods.

As mentioned above, any of the boron containing reagents, borane, diborane and dialkylboranes having from one to eight carbon atoms in each of said alkyl groups may be advantageously employed to convert the 10-methylene compounds of the formula (XXXV) to the corresponding 10-hydromethyl compounds of formula (XXXVI). However, when 6a,10a-unsaturated-10-methylene compounds of formula (XXXV) are employed as starting material, the preferred boron containing reagents are said dialkylboranes and di-sec-isoamylborane (also named bis-3-methyl-2-butylborane and disiamylborane, see e.g., Fieser, loc. cit., p. 57). When the starting material is a compound of formula (XXXV) wherein hydrogen atoms are attached at the 6a,10a positions, the preferred reagent is borane and the borane-tetrahydrofuran complex is especially preferred for reasons of efficiency and economy.

Preparation of Starting Materials

The 2-(ZW-substituted) hydroquinone starting materials of formula (III), if not known, are prepared from gentisic acid (2,5-dihydroxybenzoic acid) or the corresponding alkylphenyl ketones of formula (XXXVIII, $Y_2$ is alkyl) in which the hydroxy groups are protected, e.g., by methyl, ethyl or benzyl groups. The overall abbreviated sequence is illustrated below in Flow Sheet F.

Flow Sheet F*

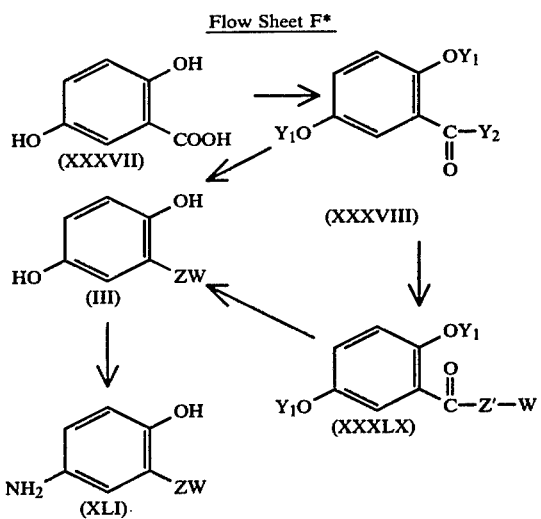

*Y₁ is alkyl having from one to four carbon atoms or benzyl;
Y₂ is alkyl, alkoxy having from one to four carbon atoms OH or NH₂.

The starting 2,5-dihydroxybenzoic acid (XXXVII) is converted to a compound of formula (XXXVIII) wherein Y₂ represents an alkoxy group, desirably methoxy or ethoxy for ease of preparation, or an amino group; and Y₁ is a hydroxy protecting group, by methods described in the literature.

The diprotected benzoic acid derivative is then converted to a compound of formula (III) by known technology. In one procedure the ester (XXXVIII) is hydrolyzed to the corresponding acid (Y₂=OH), or lithium salt, and reacted with the appropriate alkyl lithium to produce an alkyl disubstituted phenyl ketone (Y₂=alkyl). When methyl lithium is used, the resulting acetophenone derivative is treated with a Grignard Reagent (W-Z'-MgBr). The intermediate adduct is hydrolyzed to the corresponding alcohol which is then hydrogenolyzed to replace the hydroxy group with hydrogen. This procedure is especially useful for those compounds wherein Z is alkylene.

The ether groups are deblocked by suitable means: treatment with pyridine hydrochloride (Y₁=methyl) or catalytic hydrogenolysis (Y₁=benzyl), or by treatment with an acid such as trifluoroacetic acid, hydrochloric, hydrobromic or sulfuric acids, acid debenzylation is, of course, used when the group —Z—W contains sulfur.

A further method for converting compounds of formula (XXXVIII) to those of formula (III) comprises reaction of a ketone of formula (XXXVIII, Y₂=alkyl) with the appropriate triphenyl phosphonium bromide derivative [(C₆H₅)₃P⁺—Z—W]Br⁻ in the presence of a base (e.g., sodium hydride). The reaction preceeds via an alkene which is subsequently catalytically hydrogenated to the corresponding alkane (Z-W) and deblocked to the dihydroxy compound (III). Of course, when —Z— is (alk₁)ₘ—X— (alk₂)ₙ and Y₁ is benzyl, the catalytic hydrogenation also results in cleavage of the benzyl ethers.

Alternatively, conversion of structure (XXXVIII) compounds to those of structure (III) can be achieved by the sequence (XXXVIII)→(XXXIX)→(III). In this sequence, the diprotected benzamide (XXXVIII), Y₂=NH₂) is converted to the ketone (XXXIX, Z'=Z less one CH₂ group) by reaction with the appropriate Grignard reagent (BrMg-Z'-W) followed by reaction with methyl- or ethyl-magnesium halide to form the corresponding carbinol. Dehydration of the carbinol, e.g., with p-toluenesulfonic acid, affords the corresponding alkene which is then catalytically hydrogenated (Pd/C) to the alkane (III). The ether groups are deblocked (converted to hydroxy) as described above.

When Z is alkylene, Y₁ is desirably alkyl having from one to four carbon atoms or benzyl. The function of group Y₁ is to protect the hydroxy groups during subsequent reactions. It is its ability to perform a specific function; i.e., protection of the hydroxy groups, rather than its structure which is important. The selection and identification of appropriate protecting groups can easily and readily be made by one skilled in the art. The suitability and effectiveness of a group as a hydroxy protecting group are determined by employing such a group in the above-illustrated reaction sequence. It should, therefore, be a group which is easily removed to permit restoration of the hydroxy groups. Methyl is favored as a protecting alkyl group since it is easily removed by treatment with pyridine hydrochloride. The benzyl group, if used as a protecting group, is removed by catalytic hydrogenolysis or acid hydrolysis.

When Z is —(alk₁)ₘ—X—(alk₂)ₙ—, Y₁ is preferably benzyl or a substituted benzyl group since it can subsequently be removed without detriment to the Z group.

Compounds of formula (III) wherein —Z—W is -alkylene-W or —(alk₁)— X'—(alk₂)ₙ—W wherein (alk₁), (alk₂), W and n are as defined above and X' is O or S, are obtained by the following sequence (Flow Sheet G);

Flow Sheet G

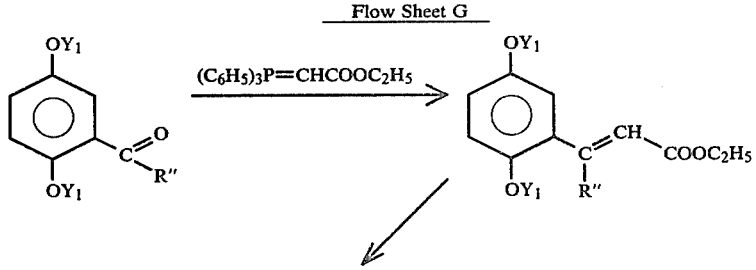

-continued

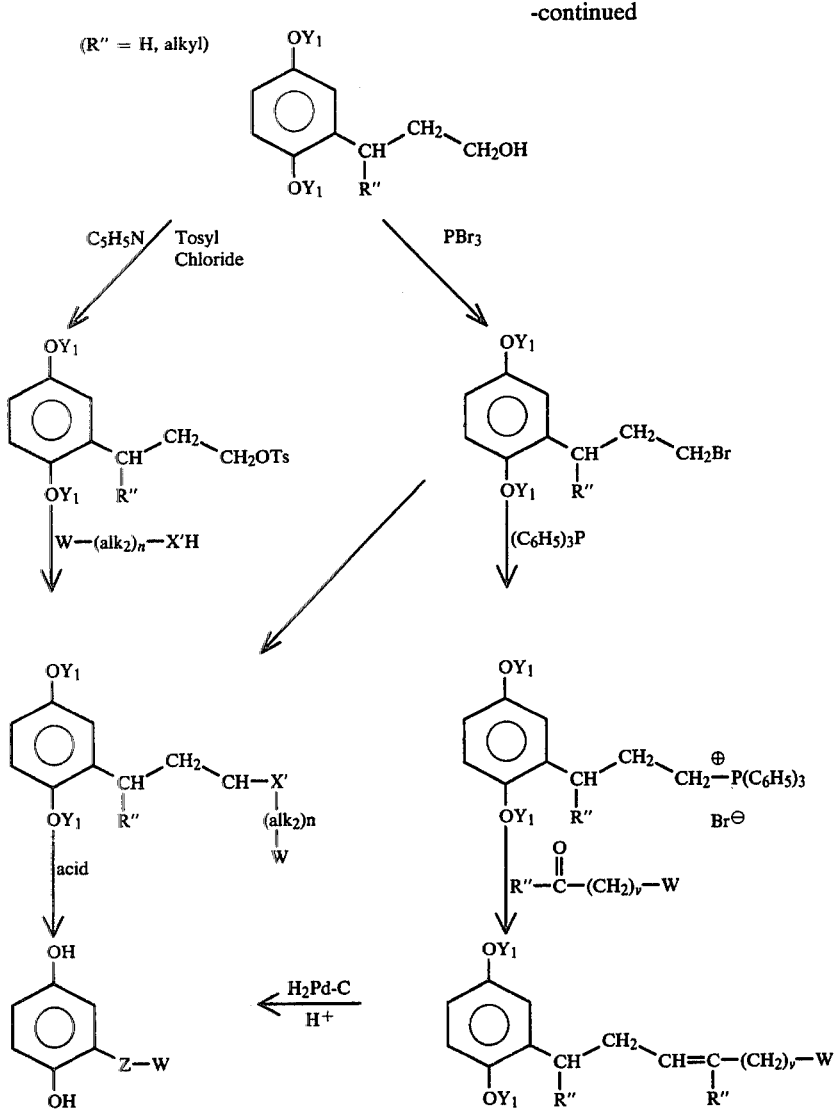

(III)
*R is hydrogen or alkyl having from one to six carbon atoms; X' is O or S; V is alkyl having from one to four carbon atoms or benzyl; v is zero to five; and Z, W, (alk$_2$) and n are previously defined.

The first step in the above sequence (the Wittig reaction) provides opportunity, by choice of appropriate reactants, to produce compounds having straight or branched alkylene groups. In the given illustration, the value of R" as methyl or ethyl permits formation of a compound having alkyl substitution on the carbon atoms ($\alpha$) adjacent to the phenyl group. Substitution of a methyl or ethyl group at other sites, e.g., the b-carbon atoms of the alkylene group, is achieved by choice of the appropriate carboalkoxy alkylidene triphenylphosphorane, e.g. $(C_6H_5)_3P=C(R")$—$COOC_2H_5$. The unsaturated ester thus produced is reduced to the corresponding saturated alcohol by reaction with lithium aluminum hydride. The presence of a small amount of aluminum chloride sometimes accelerates this reaction. Alternatively, when Y$_1$ is other than benzyl (e.g. methyl), the alcohol is produced by catalytic reduction of the unsaturated ester using palladium-carbon, followed by treatment of the saturated ester thus produced with lithium aluminum hydride. Conversion of the alcohol to the corresponding tosylate or mesylate followed by alkylation of the tosylate or mesylate with an alkali metal salt of the appropriate HX'—(alk$_2$)$_n$—W reactant, and finally removal of the protecting groups (Y$_1$) affords the desired compound of formula (III). When X' is sulfur, the protecting group Y$_1$ is methyl.

A variation of the above sequence comprises bromination of the alcohol rather than converting it to a tosylate or mesylate. Phosphorous tribromide is a convenient brominating agent. The bromo derivative is then reacted with the appropriate HX'—(alk$_2$)$_n$—W in the presence of a suitable base (Williamson reaction).

The bromo compounds also serve as valuable intermediates for increasing the chain length of the alkylene moiety in the above sequence to give compounds wherein Z is alkylene. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

In this variation, the value of the protecting group ($Y_1$) selected depends upon the particular sequence followed. When the vertical sequence on the right (Flow Sheet G) is used, benzyl is the preferred protecting group by reason of the catalytic hydrogenation step. Methyl is the preferred protecting group when the left vertical sequence is followed, since it is conveniently removed by treatment with acid as described herein.

The 4-hydroxy-3-(Z-W-substituted)anilines of formula (XLI) are prepared from corresponding 2-(Z-W-substituted)hydroquinones, (III), via the Bucherer Reaction which comprises reacting the appropriate compound of formula (III) with aqueous ammonium sulfite or bisulfite. The reaction is conducted in an autoclave at elevated temperatures, e.g. from about 150° to about 230° C. The aniline product is isolated by acidifying the cooled reaction mixture and extracting the acid mixture with, for example, ethyl acetate. The acid solution is neutralized and extracted with a suitable solvent, e.g. chloroform, to recover the aniline product. Alternatively, the aniline product is isolated by extracting the cooled reaction mixture with an appropriate solvent followed by column chromatography of the crude product.

The 4-hydroxy-3-(Z-W-substituted)anilines of formula (XLI) are alternatively prepared by the procedures described above in conjunction with Flow Sheet C but employing, for example, a starting material of the formula

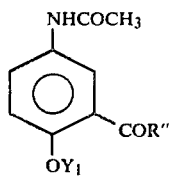

wherein R" and $Y_1$ are as defined above. This starting material is obtained from commercially available 5-aminosalicylic acid. The amino group is protected by acetylation according to standard procedures and the hydroxy protecting group, $Y_1$, introduced as described above. The resulting diprotected aminosalicylic acid is converted to aldehydes and ketones of the above structure by standard methods known to one skilled in the art. The product obtained by carrying this starting material through the process of Flow Sheet G is a N-acetyl derivative of the 4-hydroxy-3-(Z-W-substituted)anilines of formula (XLI). The acetyl group is then removed by standard hydrolysis techniques to provide the desired product of formula (XLI).

Compounds of formula (I) and (II) wherein —Z—W is —(alk$_1$)$_m$—X— (alk$_2$)$_n$—W and X is —SO— or —SO$_2$— are obtained by oxidation of the corresponding compounds in which X is —S—. Hydrogen peroxide is a convenient agent for oxidation of the thio ethers to sulfoxides. Oxidation of the thio ethers to corresponding sulfones is conveniently accomplished by means of a peracid such as perbenzoic, perphthalic or m-chloroperbenzoic acid. This latter peracid is especially useful since the by-product m-chlorobenzoic acid is easily removed.

Esters of compounds of formulae (I) and (II) wherein $R_1$ is alkanoyl or —CO—(CH$_2$)$_p$—NR$_2$R$_3$ are readily prepared by reacting formulae (I) or (II) compounds wherein $R_1$ is hydrogen with the appropriate alkanoic acid or acid of formula HOOC—(CH$_2$)$_p$—NR$_2$R$_3$ in the presence of a condensing agent such as dicyclohexylcarbodiimide. Alternatively, they are prepared by reaction with the appropriate alkanoic acid chloride or anhydride, e.g. acetyl chloride or acetic anhydride, in the presence of a base such as pyridine.

Compounds of formula (I) and (II) wherein Q is CHOH or CHCH$_2$OH and $R_1$ is hydrogen are converted to diesters by acylation according to the above-described procedures. Compounds in which only the above-defined Q moiety is acylated are obtained by mild hydrolysis of the corresponding diester derivative, advantage being taken of the greater ease of hydrolysis of the phenolic acyl group. Formula (I) and (II) compounds wherein Q is CHOH and only the 2-hydroxy group is esterified are obtained by borohydride reduction of the corresponding compounds wherein Q is C=O and $R_1$ is said alkanoyl or aminosubstituted alkanoyl. The thus-produced monoacylated dihydroxy compounds can then be acylated further with a different acylating agent to produce a diesterified compound of formula (I) and (II) in which the ester group at the 2 position is different than that in the Q moiety.

The presence of a basic group in the ester moiety (OR$_1$) in the compounds of this invention permits formation of acid-addition salts involving said basic group. When the herein described basic esters are prepared via condensation of the appropriate amino acid hydrochloride (or other acid addition salt) with the appropriate compound of formula (I) or (II) in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with the nitrogen of the benzo[c]quinoline system. Such salts are prepared by standard procedures. The basic ester derivative are, of course, able to form mono- or di-acid addition salts because of their dibasic functionality.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

Tests Using Thermal Nociceptive Stimuli (a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛" think aluminum plate. A 250 watt reflector infrared heat lamp is place under the bottom of the aluminum plate. A thermal regulator, connected to thermistors on the plate surface, programs the heat lamp to maintain a constant temperature of 57° C. Each mouse dropped into a glass cylinder (6½" diameter) resting on the hot plate, and timing is begun when the animal's feet touch the plate. At 0.5 and 2 hours after treatment with the test compound the mouse is observed for the first "flicking" movements of one or both hind feet or until 10 seconds elapse without such movements. Morphine has an MPE$_{50}$=4–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_550$ of 3.2–5.6 mg./kg. (s.c.).

(c) Tail Immersion Procedure

The method is a modification of the receptacle procedure developed by Bendasset, et. al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trail is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD-strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack reported in seconds. The clamp is removed in 30 seconds if attacking has not yet occurred, and the latency of response is recorded for 30 seconds. Morphine is active 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \, MPE = \frac{\text{test time} - \text{control time}}{\text{cutoff time} - \text{control time}} \times 100$$

The analgesic activity is reported in terms of $MPE_{50}$, the dose at which half of the maximal possible analgesic effect is observed in a given test.

The analgesic activity of several compounds of the invention in the above described test for suppresion of phenylbenzoquinone (PBQ) irritant-induced writhing are set forth below in Table I.

TABLE I

| Compound | $ED_{50}$ mg./kg., in PBQ Writhing Test | Route of Administration |
|---|---|---|
| 7,8,9,10-Tetrahydro-2-hydroxy-6,6-dimethyl-3-(1-methyl-4-phenylbutyl)-6H-dibenzo[b,d]pyran (Example 16) | 10 | oral |
| dl-7,8,9,10-Tetrahydro-2,10α-dihydroxy-6,6-dimethyl-3-(1-methyl-4-phenylbutyl)-6H-dibenzo[b,d]pyran (Example 21) | 10 | oral |
| cis-6aα,7,8,9,10,10aα-Hexahydro-2-hydroxy-6,6a-dimethyl-3-(1-methyl-4-phenylbutyl)-10-oxo-6H-dibenzo[b,d]pyran (Example 9A) | 10–32 | subcutaneous |
| dl-cis-6aα,7,8,9,10,10aα-Hexahydro-2,10-dihydroxy-6,6-dimethyl-3-(1-methyl-4-phenyl- | 27 | subcutaneous |

TABLE I-continued

| Compound | ED$_{50}$ mg./kg., in PBQ Writhing Test | Route of Administration |
|---|---|---|
| butyl)-6H-dibenzo[b,d]pyran (Example 11) | | |

The compounds of the present invention are active analgesics via oral and parenteral administration and are conveniently administered in composition form. Such compositions include a pharmaceutical carrier selected on the basis of the chosen route of administration and standard pharmaceutical practice. For example, they can be administered in the form of tablets, pills, powders or granules containing such excipients as starch, milk sugar, certain types of clay, etc. They can be administered in capsules, in admixtures with the same or equivalent excipents. They can also be administered in the form of oral suspensions, solution, emulsions, syrups and elixirs which may contain flavoring and coloring agents. For oral administration of the therapeutic agents of this invention, tablets or capsules containing from about 0.20 to about 250 mg. are suitable for most applications.

The physician will determine the dosage which will be most suitable for an individual patient and it will vary with the age, weight and response of the particular patient and the route of administration. Generally, however the initial analgesic dosage in adults may range from about 1.0 to about 1500 mg. per day in single or divided doses. In many instances, it is not necessary to exceed 250 mg. daily. The favored oral dosage range is from about 1.0 to about 300 mg./day; the preferred range is from about 1.0 to about 100 mg./day. The favored parenteral dose is from about 1.0 to about 100 mg./day; the preferred range from about 1.0 to about 50 mg./day.

This invention also provides pharmaceutical compositions, including unit dosage forms, valuable for the use of the herein described compounds as analgesics and other utilities disclosed herein. The dosage form can be given in single or multiple doses, as previously noted, to achieve the daily dosage effective for a particular utility.

In addition to having useful analgesic activity some of the instant compounds will also produce one or more of the following activities: tranquilizing agent, diuretic agent. It is not unusual to find such dual activity in a single compound. The fact that such dual activity exists may detract from the commercial desireability of the compound, but it is still useful for patients requiring both or each of these treatments.

As is well known, their tranquilizer activity is demonstrated by oral administration to rats at doses of from about 1.0 to 100 mg./kg. with subsequent decreases in spontaneous motor activity. Their activity as diuretic agents is determined by the procedure of Lipschitz et al., J. Pharmacol., 79., 97 (1943) which utilizes rats as the test animals.

This invention also provides pharmaceutical composition, including unit dosage forms, valuable for the use of the herein described compounds as analgesics and other utilities disclosed herein. The dosage form may be given in single or multiple doses, as previously noted, to achieve the daily dosage effective for a particular utility.

The compounds (drugs) described herein can be formulated for administration in solid or liquid form or oral or parenteral administration. Capsules containing drugs of this invention; i.e.; compounds of formulae (I) or (II) are prepared by mixing one part by weight of drug with nine parts of excipient such as starch or milk sugar and then loading the mixture into telescoping gelatin capsules such that each capsule contains 100 parts of the mixture. Tablets containing compounds of formulae (I) or (II) are prepared by compounding suitable mixtures of drug and standard ingredients used in preparing tablets, such as starch, binders and lubricants, such that each tablet contains from 0.5 to 100 mg. of drug per tablet.

Suspensions and solutions of these drugs, particularly those wherein $R_1$ (formulae I and II) is hydroxy, are generally prepared just prior to use in order to avoid problems of stability of the drug (e.g. oxidation) or of suspensions or solution (e.g. precipitation) of the drug up on storage. Compositions suitable for such are generally dry solid compositions which are reconstituted for injectable administration.

EXAMPLE 1 dl-Ethyl 4-[4-carboethoxy-6-hydroxy-7-(1-methyl-4-phenylbutyl)-2-oxo-2H-benzopyran-3-yl]butyrate A mixture of 51.0 g. (0.20 mole) of 2-(2',5'-dihydroxyphenyl)-5-phenylpentane, 66.2 g. (0.22 mole) of triethyl-2-oxalyl adipate [prepared by the method of Goldberg et al., Helv. Chem. Acta, 30,200 (1947)] and 18.2 ml. (0.20 mole) of phosphorous oxychloride was stirred at room temperature under a nitrogen atmosphere for seven days. The resulting dark, viscous residue was dissolved in one liter of chloroform, washed with 3×350 ml. of water, 1×350 ml. of saturated sodium chloride, dried over anhydrous magnesium sulfate and evaporated in vacuo to obtain 116 g. of a dark oil. Purification of the oil by column chromatograph over two kilograms of silica gel afforded 61.5 g. (62%) of the title compound as a yellow oil. $^1$H-NMR (CDCl$_3$), ppm. (δ): 7.3–7.1 (m,5,phenyl), 7.1 and 6.8 (s,1 aromatic), 6.7 (broad s,1,phenolic), 4.5 and 4.1 (q,2,J=8, CH$_2$CH$_3$)

EXAMPLE 2 dl-7,8,9,10-Tetrahydro-6,10-dioxo-2-hydroxy-3-(1-methyl-4-phenylbutyl)-6H-dibenzo[b,d]pyran To a dry four-necked flask fitted with condenser, mechanical stirrer, nitrogen inlet and addition funnel was placed 4.36 g. (0.090 mole) of 50% sodium hydride in mineral oil. The hydride was washed three times with pentane then a mixture of 72 ml. each of benzene and ethanol was added dropwise. When hydrogen evolution and exotheric reaction had ceased, a solution of 9.0 g. (0.018 mole) of dl-ethyl 4-[4-carboethoxy-6-hydroxy-7-(1-methyl-4-phenyl)butyl-2-oxo-2H-benzopyran-3-yl]butyrate in 108 ml. of benzene was added dropwise and the resulting gummy suspension was heated at reflux for 1.5 hours. The mixture was acidified with 10% hydrochloric acid at 0° C. and the organic layer was separated. The aqueous phase was extracted with 2×200 ml. of ethyl ether and the combined organic layers dried over anhydrous magnesium sulfate and evaporated to dryness in vacuo to obtain 7.2 g. of an orange foam. To the foam was added 70 ml. of concentrated hydrochloric acid, 140 ml. of glacial acetic acid and 11 ml. of water and the resulting mixture heated at reflux for 30 minutes during which the mixture darkened and a crystalline solid precipitated. Upon cooling and filtration 2.0 g. of the title compound was obtained as yellow crystals, M.P. 200°-202° C. Upon dilution of the filtrate with water, extraction with ether, backwashing with water and saturated sodium bicarbonate solution, drying (MgSO$_4$) and evaporation to dryness an additional 0.46 g. of product was obtained, M.P. 196°-200° C. (total yield 40%). A portion was recrystallized twice from ethyl acetate to provide an analytical sample, M.P. 206°-207° C.; $^1$H-NMR (perdeuterodimethylsulfoxide), ppm. ($\delta$): 9.8 variable (s,1,phenolic), 8.2 (s,1,aromatic), 7.4–7.0 (m,6,aromatic), 1.3 (d,3,J=5, $\alpha$-CH$_3$); IR (KBr), ($\mu$): 3.45, 5.88, and 6.0; Mass Spectrum (m/e), 376 (M+).

Anal. Calc'd. for C$_{24}$H$_{24}$O$_4$: C, 76.57; H, 6.43. Found: C, 76.25; H, 6.63.

EXAMPLE 3

Employing the procedures of Examples 1 and 2 but using the appropriate starting material in the procedure of Example 1 in place of 2-(2',5'-dihydroxyphenyl)-5-phenylpentane in each case, the following dibenzopyrones are obtained.

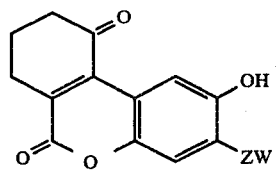

where Z is alkylene:

| Z | W |
|---|---|
| —(CH$_2$)$_6$— | C$_6$H$_5$ |
| —(CH$_2$)$_7$— | 4-FC$_6$H$_4$ |
| —(CH$_2$)$_8$— | 2-ClC$_6$H$_4$ |
| —(CH(CH$_3$)(CH$_2$)$_5$— | cyclohexyl |
| —CH(CH$_3$)(CH$_2$)$_6$— | 4-FC$_6$H$_4$ |
| —CH(CH$_3$)(CH$_2$)$_7$— | C$_6$H$_5$ |
| —(CH$_2$)$_3$— | cyclopentyl |
| —CH$_2$— | 4-ClC$_6$H$_4$ |
| —(CH$_2$)$_3$— | 2-pyridyl |
| —(CH$_2$)$_4$— | 4-pyridyl |
| —(CH$_2$)$_4$— | 3-pyridyl |
| —(CH(CH$_3$)— | C$_6$H$_5$ |
| —CH(CH$_3$)CH$_2$CH(C$_2$H$_5$)— | C$_6$H$_5$ |
| —CH(C$_2$H$_5$) (CH$_2$)$_3$— | C$_6$H$_5$ |
| —CH$_2$CH(CH$_3$)(CH$_2$)$_2$— | C$_6$H$_5$ |
| —(CH$_3$)$_2$C(CH$_2$)$_5$— | C$_6$H$_5$ | where Z is (alk$_1$)—X—)alk$_2$)$_n$

| alk$_1$ | X | Alk$_2$ | n | W |
|---|---|---|---|---|
| (CH$_2$)$_3$ | O | — | 0 | C$_6$H$_5$ |
| (CH$_2$)$_3$ | O | CH$_2$ | 1 | CH$_3$ |
| (CH$_2$)$_3$ | O | (CH$_2$)$_2$ | 1 | 4-pyridyl |
| (CH$_2$)$_3$ | O | CH(CH$_3$) | 1 | 4-piperidyl |
| CH(CH$_3$)(CH$_2$)$_2$ | O | CH$_2$CH(C$_2$H$_5$) | 1 | cyclohexyl |
| CH(C$_2$H$_5$)(CH$_2$)$_2$ | O | — | 0 | 2-(4-FC$_6$H$_4$)C$_7$H$_{12}$ |
| (CH$_2$)$_4$ | O | CH$_2$ | 1 | 3-pyridyl |
| (CH$_2$)$_4$ | O | CH$_2$CH(CH$_3$) | 1 | 4-(C$_6$H$_5$)C$_6$H$_{10}$ |
| (CH$_2$)$_4$ | O | (CH$_2$)$_5$ | 1 | 3-piperidyl |
| (CH$_2$)$_3$ | S | — | 0 | cyclopropyl |
| (CH$_2$)$_3$ | S | — | 0 | 4-(4-ClC$_6$H$_4$)C$_6$H$_{10}$ |
| (CH$_2$)$_3$ | S | CH$_2$ | 1 | cyclopentyl |
| (CH$_2$)$_3$ | S | (CH$_2$)$_2$ | 1 | 4-ClC$_6$H$_5$ |
| CH(CH$_3$)(CH$_2$)$_2$ | S | (CH$_2$)$_4$ | 1 | CH$_3$ |
| CH(C$_2$H$_5$)(CH$_2$)$_2$ | S | — | 0 | C$_6$H$_5$ |
| (CH(C$_2$H$_5$)(CH$_2$)$_2$ | S | (CH$_2$)$_2$CH(CH$_3$) | 1 | 4-pyridyl |
| CH(CH$_3$)(CH$_2$)$_3$ | O | — | 0 | 2-(4-FC$_6$H$_4$)C$_5$H$_8$ |
| CH(CH$_3$)(CH$_2$)$_3$ | S | (CH$_2$)$_4$ | 1 | CH$_3$ |
| — | S | CH(CH$_3$(CH$_2$)$_5$ | 1 | CH$_3$ |
| — | S | C(CH$_3$)$_2$(CH$_2$)$_5$ | 1 | CH$_3$ |
| — | S | (CH$_2$)$_8$ | 1 | CH$_3$ |
| — | S | CH$_2$ | 1 | C$_6$H$_5$ |
| — | S | CH(CH$_3$)(CH$_2$)$_3$ | 1 | C$_6$H$_5$ |
| — | S | CH$_2$ | 1 | cyclohexyl |
| — | S | (CH$_2$)$_4$ | 1 | 2-pyridyl |
| — | S | CH(CH$_3$)(CH$_2$)$_2$ | 1 | 4-ClC$_6$H$_4$ |
| — | S | — | 0 | C$_6$H$_5$ |
| — | S | — | 0 | 3-(C$_6$H$_5$)C$_7$H$_{12}$ |
| — | S | — | 0 | CH$_3$ |
| — | O | CH$_2$C(CH$_3$)$_2$(CH$_2$)$_4$ | 1 | CH$_3$ |
| — | O | (CH$_2$)$_9$ | 1 | C$_6$H$_5$ |
| — | O | (CH$_2$)$_9$ | 1 | CH$_3$ |
| — | O | CH(CH$_3$)CH$_2$ | 1 | 2-pyridyl |
| — | O | (CH$_2$)$_3$ | 1 | 4-FC$_6$H$_4$ |
| — | O | CH(CH$_3$)(CH$_2$)$_2$ | 1 | 4-piperidyl |
| — | O | CH(CH$_3$)(CH$_2$)$_2$ | 1 | 4-ClC$_6$H$_4$ |
| — | O | CH$_2$ | 1 | C$_6$H$_5$ |
| — | O | — | 0 | C$_6$H$_5$ |
| — | O | — | 0 | cyclopropyl |

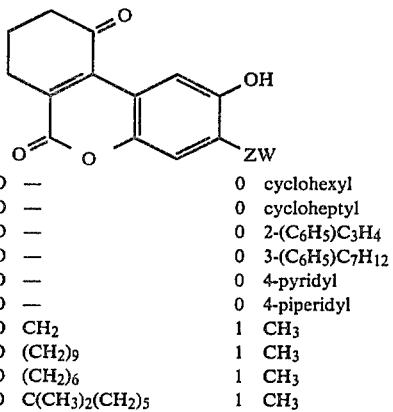

| | O | — | | 0 | cyclohexyl |
| --- | --- | --- | --- | --- | --- |
| — | O | — | | 0 | cycloheptyl |
| — | O | — | | 0 | 2-($C_6H_5$)$C_3H_4$ |
| — | O | — | | 0 | 3-($C_6H_5$)$C_7H_{12}$ |
| — | O | — | | 0 | 4-pyridyl |
| — | O | — | | 0 | 4-piperidyl |
| — | O | $CH_2$ | | 1 | $CH_3$ |
| — | O | $(CH_2)_9$ | | 1 | $CH_3$ |
| — | O | $(CH_2)_6$ | | 1 | $CH_3$ |
| — | O | $C(CH_3)_2(CH_2)_5$ | | 1 | $CH_3$ |

EXAMPLE 4 dl-7,8,9,10-Tetrahydro-6,10-dioxo-2-hydroxy-3-(1-methyl-4-phenylbutyl)-6H-di-benzo[b,d]pyran 10-(1,2-dithioethylene)ketal A suspension of 2.0 g. of dl-7,8,9,10-tetrahydro-6,10-dioxo-2-hydroxy-3-(1-methyl-4-phenylbutyl)-6H-dibenzo[b,d]pyran in 4 ml. of 1,2-ethanedithiol was treated with 1 ml. of boron trifluoride etherate under a nitrogen atmosphere. After 30 minutes the resulting green solution was diluted with 100 ml. of ethyl ether, washed with 3×30 ml. of water, 30 ml. of saturated sodium bicarbonate solution, dried (MgSO4) and concentrated in vacuo in a well ventilated hood to an oil. The oil was crystallized from hexane, washing with benzene and ether. After drying in vacuo at 68° C., 1.72 g. of cyclic thioketal was obtained, M.P. 140°–147° C. An additional 0.64 g. was obtained from the mother liquor. An analytical sample was obtained by recrystallization from benzene-hexane as yellow crystals, M.P. 144°–150° C. Mass Spectrum: (M/e) 452 (M+).

Anal. Calc'd. for $C_{26}H_{28}O_2S_2$: C, 68.99; H, 6.24; S, 14.17. Found: C, 68.99; H, 6.11; S, 13.83.

EXAMPLE 5 dl-7,8,9,10-Tetrahydro-2-hydroxy-3-(1-methyl-4-phenylbutyl)-6,6-dimethyl-10-oxo-6H-dibenzo[b,d]pyran 1,2-dithioethyleneketal A suspension of 11.5 g. (25.4 mmoles) of dl-7,8,9,10-tetrahydro-6,10-dioxo-2-hydroxy-3-(1-methyl-4-phenylbutyl)-6H-dibenzo[b,d]pyran 10-(1,2-dithioethylene)ketal in 225 ml. of dry ether was added dropwise to a solution of 131 ml. of 2.9 M methyl magnesium iodide in ether diluted with an additional 225 ml. of ether. The resulting yellow suspension was heated at reflux for two days. The light yellow reaction mixture containing a gummy precipitate was carefully treated with 50 ml. of 1 N hydrochloric acid at 0° C., then 150 ml. of 6 N HCl was added and the dark red mixture was stirred at room temperature for one hour. The ether layer was separated, washed with 2×200 ml. of water, 2×200 ml. of saturated sodium bicarbonate, dried over magnesium sulfate and concentrated to obtain 13 g. of a dark foam which was purified by silica gel column chromatography to afford 8.8 g. of the title compound as a foam. $^1$H-NMR (CDCl$_3$) ppm, (δ: 7.6 and 6.6 (s,1,aromatic), 7.4–6.9 (m,5,phenyl), 4.7 (s,1,phenolic), 3.4 (s,4, SCH$_2$CH$_2$S), 1.3 (s,6,gem dimethyl).

EXAMPLE 6 dl-7,8,9,10-Tetrahydro-2-hydroxy-6,6-dimethyl-3-(1-methyl-4-phenylbutyl)-10-oxo-6H-dibenzo[b,d]pyran The purified foam obtained in the preceding example, 8.8 g. (18.8 mmoles) was dissolved in a mixture of 590 ml. of acetone and 29.5 ml. of water. Mercuric chloride (11.1 g., 41 mmoles) and cadmium carbonate (11.1 g., 64 mmoles) were added and the mixture stirred at ambient temperature for 0.5 hr. The mixture was further treated with 5.0 g. each of the latter two reagents, stirred for an additional hour, treated with 2.0 g. of each reagent, then stirred overnight. The resulting suspension was filtered, the filtrate concentrated to a solid residue and 500 ml. of ethyl acetate and 300 ml. of water were added. Filtration of the resulting suspension gave 2.65 g. of product, M.P. 186°–188° C. The organic layer of the filtrate was separated, washed with 10% potassium iodide solution (3×175 ml.) and water (1×200 ml.), dried over magnesium sulfate and concentrated until solids (yellow) precipitated. Upon filtration an additional 2.70 g. of product was obtained. A third crop was obtained from the mother liquor, 0.46 g. Combined yield 75%.

Two recrystallizations from ethanol afforded an analytical sample of the title compound as yellow crystals, M.P. 188°–189° C. IR (CHCl$_3$)µ: 5.85 and 6.00. UV in ethanol $\lambda_{max}$. 283 (ε=21,800), 269 (ε=18,200), 300 (ε=7,730), 348 (ε=5,680).

Anal. Calc'd for $C_{26}H_{30}O_3$: C, 79.96; H, 7.74. Found: C, 79.75; H, 7.68.

EXAMPLE 7

Employing the dibenzopyrones provided in Examples 2 and 3 as starting materials, preparing the 1,2-dithioethylene ketals by the procedure of Example 4, reacting said ketals by the procedure of Example 5 but using either methylmagnesium iodide, ethylmagnesium iodide, n-propylmagnesium iodide, n-butylmagnesium iodide, or the corresponding chloride or bromides; followed by deprotection of the 10-keto group by the procedure of Example 6, in each case, affords analogous compounds of the structure

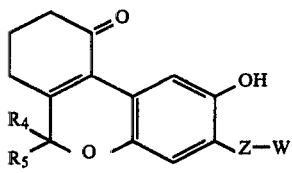

wherein R₄ and R₅ are the same and are each methyl, ethyl, n-propyl or n-butyl.

EXAMPLE 8 dl-7,8,9,10-Tetrahydro-2-hydroxy-3-(1-methyl-4-phenylbutyl)-10-oxo-6H-dibenzo[b,d]pyran To a suspension of 2 g. of lithium aluminium hydride in 50 ml. of dry ether is added a mixture of 9.35 g. (20 mmoles) of dl-7,8,9,10-tetrahydro-6,10-dioxo-2-hydroxy-3-(1-methyl-4-phenylbutyl)-6H-dibenzo[b,d]pyran 10-(1,2-dithioethylene)ketal in 100 ml. of the same solvent. After heating at reflux overnight the excess hydride is decomposed by the cautious addition of water, the resulting paste filtered washing several times with ether. The combined ether layers were dried (MgSO₄) and evaporated to dryness in vacuo to provide the 10-(1,2-dithioethylene)ketal of the desired product. After removal of the thioketal protecting group by the procedure of Example 6, the title compound is obtained.

When each of the compounds provided in Example 3 is converted to its 10-(1,2-dithioethylene)ketal by the procedure of Example 4 then reduced with lithium aluminum hydride by the above method, the corresponding compounds of of the following structure are obtained.

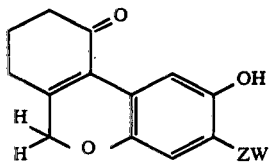

EXAMPLE 9

A.

dl-cis-6a,7,8,9,10,10a-Hexahydro-2-hydroxy-6,6-dimethyl-3-(1-methyl-4-phenylbutyl)-10-oxo-6H-dibenzo[b,d]pyran To a rapidly stirred solution of 600 mg. of lithium metal in 500 ml. of anhydrous ammonia maintained at −75° C. was added over a five minute period a solution of 2.00 g. (5.12 mmoles) of dl-7,8,9,10-tetrahydro-2-hydroxy-6,6-dimethyl-3-(1-methyl-4-phenylbutyl)-10-oxo-6H-dibenzo[b,d]pyran in 250 ml. of tetrahydrofuran. Ten minutes after the addition was completed, the blue color was discharged with excess ammonium chloride, the ammonia allowed to evaporate, the residue diluted with 250 ml. of water and extracted with ether. The ether extracts were washed with saturated sodium chloride, dried over anhydrous magnesium sulfate and evaporated to dryness to obtain 2.31 g. of yellow foam.

The foam was chromatographed on a column containing 140 g. of silica gel eluting first with pure benzene, then with benzene containing 2% ether, and finally, 4% ether. Fractions of 20 ml. each were collected. Fractions 61–80 were combined and evaporated to afford 80 mg. of the title compound as tan crystals, M.P. 108°–115° C. Recrystallization from ether gave white crystals, M.P. 121°–123° C.; ¹H-NMR (CDCl₃) ppm. (δ): 7.5–7.1 (m,5,phenyl), 7.1 (broad s,1,phenolic), 6.7 and 6.4 (s,1,aromatic), 3.9 (d,1,J=5, benzylic CH), 1.5 and 1.3 (s,3,gem-methyls); IR(KBr) μ: 3.0, 3.45, 5.90; Mass spectrum (m/e): 392 (M+), 377 (M-15).

Anal. Calc'd. for C₂₆H₃₂O₃: C, 79.55; H, 8.22. Found: C, 79.86; H, 8.20.

B.

dl-trans-6a,7,8,9,10,10a-Hexahydro-2-hydroxy-6,6-dimethyl-3-(1-methyl-4-phenylbutyl)-10-oxo-6H-dibenzo[b,d]pyran Upon combining fractions 161–210 from the silica gel column, evaporation to dryness and crystallization from ether-ethyl acetate, 100 mg. of the title compound was obtained as tan crystals. M.P. 143°–148° C. Recrystallization from ethanol-water afforded white crystals, M.P. 155°–157° C.;, ¹H-NMR (CDCl₃) ppm (δ): 7.5–7.1 (m,5,phenyl), 6.6 and 6.7 (s,1,aromatic), 5.9 (broad s,1,phenolic), 3.5 (d,1,J=12, benzylic CH), 1.4 and 1.1 (s,3,gem-methyls); IR (KBr)μ: 3.0,3.45,5.78; Mass spectrum (M/e): 392 (M+), 377 (M-15).

Anal. Calc'd for C₂₆H₃₂O₃: C, 79.55; H, 8.22. Found: C, 79.34; H, 8.17.

EXAMPLE 10

When the products provided in Examples 7 and 8 are reduced with lithium and ammonia then separated by the method of Example 9 the 6a, 10a-cis and 6a,10a-trans isomers of each of the following compounds are similarly provided

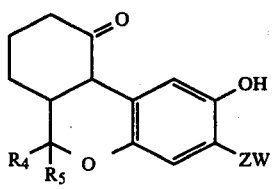

| R₄=R₅= | Z | W |
|---|---|---|
| H | —(CH₂)₆— | C₆H₅ |
| CH₃ | —(CH₂)₇— | 4-FC₆H₄ |
| C₂H₅ | —(CH₂)₈— | 2-ClC₆H₄ |
| n-C₃H₇ | —CH(CH₃)(CH₂)₅— | cyclohexyl |
| n-C₄H₉ | —CH(CH₃)(CH₂)₆— | 4-FC₆H₄ |
| H | —CH(CH₃)(CH₂)₇— | C₆H₅ |
| CH₃ | —(CH₂)₃ | cyclopentyl |
| C₂H₅ | —CH₂— | 4-ClC₆H₄ |

-continued

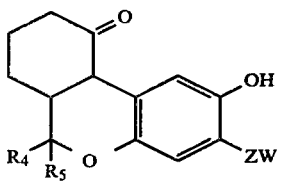

| R₄=R₅= | Z | W |
|---|---|---|
| n-C₃H₇ | —(CH₂)₃— | 2-pyridyl |
| n-C₄H₇ | —(CH₂)₄— | 4-pyridyl |
| H | —(CH₂)₄— | 3-pyridyl |
| CH₃ | —CH(CH₃)— | C₆H₅ |
| C₂H₅ | —CH(CH₃)CH₂CH(C₂H₅)— | C₆H₅ |
| n-C₃H₇ | —CH(C₂H₅)(CH₂)₃— | C₆H₅ |
| n-C₄H₉ | —CH₂CH(CH₃)(CH₂)₂— | C₆H₅ |
| H | —(CH₃)₂C(CH₂)₅— | C₆H₅ |
| CH₃ | —(CH₂)₃—O— | C₆H₅ |
| C₂H₅ | —(CH₂)₃—OCH₂— | CH₃ |
| n-C₃H₇ | —(CH₂)₃—O—(CH₂)₂— | 4-pyridyl |
| n-C₄H₇ | —(CH₂)₃—O—CH(CH₃)— | 4-piperidyl |
| H | —CH(CH₃)(CH₂)₂—O—CH₂CH(C₂H₅)— | cyclohexyl |
| CH₃ | —CH(C₂H₅)(CH₂)₂—O— | 2-(4-FC₆H₄)C₇H₁₂ |
| C₂H₅ | —(CH₂)₄—O—CH₂— | 3-pyridyl |
| n-C₃H₇ | —(CH₂)₄—O—CH₂CH(CH₃)— | 4-(C₆H₅)C₆H₁₀ |
| n-C₄H₉ | —(CH₂)₄—O—(CH₂)₅— | 3-pyridyl |
| H | —(CH₂)₃—S— | cyclopropyl |
| CH₃ | —(CH₂)₃—S— | 4-(4-ClC₆H₄)C₆H₁₀ |
| C₂H₅ | —(CH₂)₃—S—CH₂— | 4-ClC₆H₄ |
| n-C₃H₇ | —CH(CH₃)(CH₂)₂—S—(CH₂)₄— | CH₃ |
| n-C₄H₉ | —CH(C₂H₅)(CH₂)₂—S— | C₆H₅ |
| H | —CH(C₂H₅)(CH₂)₂—S—(CH₂)₂CH(CH₃)— | 4-pyridyl |
| CH₃ | —CH(CH₃)(CH₂)₃—S— | 2-(4-FC₆H₄)C₅H₈ |
| C₂H₅ | —CH(CH₃)(CH₂)₃—S—(CH₂)₄ | CH₃ |
| n-C₃H₇ | —CH(CH₃)(CH₂)₃—S—(CH₂)₄— | CH₃ |
| n-C₄H₉ | —CH(CH₃)(CH₂)₃—S—(CH₂)₄— | CH₃ |
| H | —SCH(CH₃)(CH₂)₅— | CH₃ |
| CH₃ | —S(CH₂)₈— | CH₃ |
| C₂H₅ | —SCH₂— | C₆H₅ |
| n-C₃H₇ | —SCH(CH₃)(CH₂)₃ | C₆H₅ |
| n-C₄H₉ | —SCH₂— | cyclohexyl |
| H | —S(CH₂)₄ | 2-pyridyl |
| CH₃ | —SCH(CH₃)(CH₂)₂— | 4-ClC₆H₄ |
| C₂H₅ | —S— | C₆H₅ |
| n-C₃H₇ | —S— | 3-(C₆H₅)C₇H₁₂ |
| n-C₄H₉ | —S— | CH₃ |
| H | —O(CH₂)₉— | C₆H₅ |
| CH₃ | —O(CH₂)₉— | CH₃ |
| C₂H₅ | —O(CH₂)₂— | 4-pyridyl |
| n-C₃H₇ | —O(CH₂)₃— | 2-piperidyl |
| n-C₄H₉ | —OCH₂— | 4-FC₆H₄ |
| H | —O— | cyclopropyl |
| CH₃ | —O— | cyclopentyl |
| C₂H₅ | —O— | cycloheptyl |
| n-C₃H₇ | —O— | 2-(C₆H₅)C₃H₄ |
| n-C₄H₉ | —O— | 4-pyridyl |
| H | —O— | 4-piperidyl |
| CH₃ | —O(CH₂)₃— | CH₃ |
| C₂H₅ | —OCH₂ | CH₃ |
| n-C₃H₇ | —O(CH₂)₉— | CH₃ |
| n-C₄H₉ | —OC(CH₃)₂(CH₂)₅— | CH₃ |

EXAMPLE 11 dl-cis-6a,7,8,9,10a-Hexahydro-2,10-dihydroxy-6,6-dimethyl-3-(1-methyl-4-phenylbutyl)-6H-dibenzo[b,d]-pyran A solution of 286 mg. (0.73 mmole) of dl-cis-6a,7,8,9,10,10a-hexahydro-2-hydroxy-6,6-dimethyl-3-(1-methyl-4-phenylbutyl)-10-oxo-6H-dibenzo[b,d]pyran in 5 ml. of ethanol was treated with 143 mg. (3.7 mmoles) of sodium borohydride at 0° C. under a nitrogen atmosphere. After stirring for 20 minutes the reaction mixture was poured onto an ice cold mixture of 5% aqueous hydrochloric acid and ether. The ether layer was separated and the aqueous phase further extracted with ether. The combined ether extracts were washed with saturated sodium bicarbonate solution, dried (MgSO₄) and evaporated to dryness to obtain 281 mg. of a foam. Crystallization from ether-petroleum ether gave 141 mg. of the title compound as a mixture of the 10α-ol and 10β-ol isomers; M.P. 117°–119° C.; ¹H-NMR(CDCl₃)ppm, (δ): 7.7 (s,1,aromatic), 7.6 variable (broad s,1,phenolic), 7.4–7.0 (m,5, phenyl), 4.6 (broad m,0.25 equatorial alcoholic CH), 4.6 variable (broad m,1,OH), 3.3–2.4 (m,4,benzylic protons); TLC(1:1 benzene-ether), R$_f$: 0.26, 0.29. Mass spectrum (m/e): 394 (M⁺), 379 (M-15).

EXAMPLE 12

By employing the 6a,10a-cis isomers provided in Example 10 in the procedure of Example 11, the corresponding compounds of the structure below are obtained as a mixture of the 10α-ol and 10β-ol isomers.

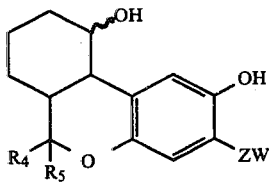

| $R_4=R_5=$ | Z | W |
|---|---|---|
| H | —(CH$_2$)$_6$— | C$_6$H$_5$ |
| n-C$_3$H$_7$ | —CH(CH$_3$)(CH$_2$)$_5$— | cyclohexyl |
| H | —CH(CH$_3$)(CH$_2$)$_7$ | C$_6$H$_5$ |
| C$_2$H$_5$ | —CH$_2$— | 4-ClC$_6$H$_4$ |
| n-C$_4$H$_7$ | —(CH$_2$)$_4$— | 4-pyridyl |
| CH$_3$ | —CH(CH$_3$)— | C$_6$H$_5$ |
| C$_2$H$_5$ | —CH(CH$_3$)CH$_2$CH(C$_2$H$_5$)— | C$_6$H$_5$ |
| H | —(CH$_3$)$_2$C(CH$_2$)$_5$— | C$_6$H$_5$ |
| CH$_3$ | —(CH$_2$)$_3$O— | C$_6$H$_5$ |
| C$_2$H$_5$ | —(CH$_2$)$_3$OCH$_2$— | CH$_3$ |
| n-C$_4$H$_7$ | —(CH$_2$)$_3$OCH(CH$_3$)— | 4-piperidyl |
| CH$_3$ | —CH(C$_2$H$_5$)(CH$_2$)$_2$O— | 2-(4-FC$_6$H$_4$)C$_7$H$_{12}$ |
| n-C$_3$H$_7$ | —(CH$_2$)$_4$OCH$_2$CH(CH$_2$)— | 4-(C$_6$H$_5$)C$_6$H$_{10}$ |
| n-C$_4$H$_9$ | —(CH$_2$)$_4$—O(CH$_2$)$_5$— | 3-pyridyl |
| H | —(CH$_2$)$_3$—S— | cyclopropyl |
| n-C$_3$H$_7$ | —CH(CH$_3$)(CH$_2$)$_2$—S—(CH$_2$)$_4$— | CH$_3$ |
| n-C$_4$H$_9$ | —CH(C$_2$H$_5$)(CH$_2$)$_2$—S— | C$_6$H$_5$ |
| H | —SCH(CH$_3$)(CH$_2$)$_5$— | CH$_3$ |
| CH$_3$ | —S(CH$_2$)$_8$— | CH$_3$ |
| C$_2$H$_5$ | —SCH$_2$— | C$_6$H$_5$ |
| H | —S(CH$_2$)$_4$— | 2-pyridyl |
| CH$_3$ | —SCH(CH$_3$)(CH$_2$)$_2$— | 4-ClC$_6$H$_4$ |
| C$_2$H$_5$ | —S— | C$_6$H$_5$ |
| n-C$_3$H$_7$ | —S— | 3-(C$_6$H$_5$)C$_7$H$_{12}$ |
| n-C$_4$H$_9$ | —S— | CH$_3$ |
| H | —O(CH$_2$)$_9$— | C$_6$H$_5$ |
| CH$_3$ | —O(CH$_2$)$_2$— | 4-pyridyl |
| C$_2$H$_5$ | —O(CH$_2$)$_3$— | 2-pyeridyl |
| n-C$_3$H$_7$ | —OCH$_2$C(CH$_3$)$_2$(CH$_2$)$_4$— | CH$_3$ |
| n-C$_4$H$_9$ | —OCH$_2$— | C$_6$H$_5$ |
| H | —O— | C$_6$H$_5$ |
| CH$_3$ | —O— | cyclopropyl |
| C$_2$H$_5$ | —O— | cycloheptyl |
| n-C$_3$H$_7$ | —O— | 3-(C$_6$H$_5$)C$_7$H$_{12}$ |
| n-C$_4$H$_9$ | —OCH$_2$— | CH$_3$ |
| H | —O(CH$_2$)$_9$ | CH$_3$ |

EXAMPLE 13 dl-trans-6a,7,8,9,10,10a-Hexahydro-2,10-dihydroxy-6,6-dimethyl-3-(1-methyl-4-phenylbutyl)-6H-dibenzo[b,d]-pyran A. Employing the procedure of Example 11, 300 mg. of the transketone obtained in Example 9, part B was reduced with 150 mg. of sodium borohydride to obtain 300 mg. of a foam which was chromatographed on a column containing 30 g. of silica gel. After a column volume of benzene was collected elution was continued with 9:1 benzene-ether taking 12 ml. fractions. The residue from fractions 17-22 was crystallized from petroleum ether to yield 32 mg. of product as tan crystals; M.P. 154°-158° C.; Mass Spectrum: m/e-394(M+), 379(M-15); $^1$H-NMR(CDCl$_3$), ppm(δ): 7.4-7.0(m,6,-phenolic and phenyl), 6.7-6.5(m,2,aromatic), 5.0(m,1,HO), 4.5(m,1,alcoholic CH), 3.2-2.4(m,4,benzylic protons), 1.4 and 1.1 (s,3,gem-methyls); TLC (1:1 benzene/ether) R$_f$: 0.47.

B. The residue from fractions 25-33 was crystallized from petroleum ether to yield 28 mg. of product as white crystals; M.P. 150°-151° C.; $^1$H-NMR(CDCl$_3$)ppm, (δ): 7.4-7.0 (m,6,phenolic and phenyl), 6.7-6.5 (m,2,aromatic), 4.9 (m,1,HO), 4.5(m,1,alcoholic CH), 3.3-2.4(m,4,benzylic protons), 1.4 and 1.1 (s,3,gem-methyls); TLC (1:1 benzene/ether) R$_f$: 0.37.

EXAMPLE 14 dl-7,8,9,10-Tetrahydro-2-hydroxy-3-(1-methyl-4-phenylbutyl)-6-oxo-6H-dibenzo[b,d]pyran A mixture of 5.0 g. (19.5 mmoles) of 2-(2',5'-dihydroxyphenyl)-5-phenylpentane, 3.4 g. (21.7 mmoles) 2-carboethoxycyclohexanone and 1.78 ml. (19.5 mmoles) of phosphorus oxychloride was stirred for five days under a nitrogen atmosphere. The solidified reaction mixture was dissolved in 175 ml. of chloroform, washed with 3×50 ml. of water and 50 ml. of saturated sodium bicarbonate solution, dried (MgSO$_4$) and evaporated to dryness at reduced pressure to obtain 13.8 g. of a partially crystalline solid. Trituration with hexane and evaporation of the filtrate gave 6.0 g. of crude product, M.P. 184°-193° C. Recrystallization from chloroform-hexane provided 2.66 g. of the title compound as tan crystals; M.P. 201°-203° C. A second crop, 1.7 g. was obtained from the mother liquor. $^1$H-NMR(CDCl$_3$)ppm, (δ): 7.4-7.1 (m,5,phenyl), 7.1 and 7.05 (s,1,aromatic), 3.6-3.0 (m,1,CH), 2.9-2.3 (m,6,benzylic and allylic CH$_2$), 1.9-1.4 (m,8,CH$_2$), 1.2 (d,3,J=7), α-CH$_3$); IR(KBr) 6.0μ; Mass spectrum (m/e): 362(M+).

Anal. Calc'd for C$_{24}$H$_{26}$O$_3$: C, 79.53; H, 7.23. Found: C, 79.61; H, 7.43.

EXAMPLE 15

By employing the appropriate starting material in place of 2-(2',5'-dihydroxyphenyl)-5-phenylpentane in each case in procedure of Example 14 the following compounds are provided.

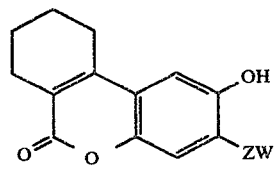

where Z is alkylene:

| Z | W |
|---|---|
| —CH(CH$_3$)CH$_2$— | cyclopentyl |
| —CH(CH$_3$)CH$_2$— | cyclopropyl |
| —CH(CH$_3$)CH(CH$_3$)— | cyclohexyl |

-continued

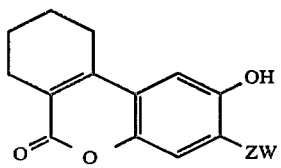

| | |
|---|---|
| —CH(C₂H₅)(CH₂)₃— | C₆H₅ |
| —(CH₂)₂CH(C₂H₅)— | C₆H₅ |
| —CH₂CH(CH₃)(CH₂)₂— | C₆H₅ |
| —(CH₃)₂C(CH₂)₃— | C₆H₅ |
| —(CH₂)₃— | 2-pyridyl |
| —(CH₂)₃— | 3-pyridyl |
| —CH(CH₃)(CH₂)₃— | 4-pyridyl |
| —(CH₂)₄— | 4-pyridyl |
| —(CH₂)₄— | 3-piperidyl |
| —(CH₂)₄— | 4-piperidyl |
| —CH₂CH(CH₃)CH₂— | 2-pyridyl |
| —CH₂CH(CH₃)CH₂— | 4-piperidyl |
| —CH(CH₃)CH(CH₃)CH₂— | 3-piperidyl |
| —(CH₂)₈— | C₆H₅ |
| —CH(CH₃)(CH₂)₆— | C₆H₅ |
| —CH(CH₃)(CH₂)₇— | C₆H₅ |
| —CH(CH₃)(CH₂)₃— | 4-FC₆H₄ |
| CH(CH₃)(CH₂)₄— | 4-ClC₆H₄ |
| —(CH₂)₂— | cyclobutyl |
| —CH(CH₃)(CH₂)₂— | cycloheptyl |
| —CH(CH₃)(CH₂)₂— | 4-ClC₆H₄ |
| —CH(CH₃)(CH₂)₂CH(CH₃)— | cyclohexyl |
| —CH(CH₃)(CH₂)₂CH(CH₃)— | 4-piperidyl | where Z is (alk₁)-X-(alk₂)n:

| alk₁ | X | alk₂ | n | W |
|---|---|---|---|---|
| CH(CH₃)(CH₂)₂ | O | — | 0 | C₆H₅ |
| (CH₂)₃ | O | — | 0 | 4-FC₆H₄ |
| (CH₂)₃ | O | — | 0 | 4-(C₆H₅)C₆H₁₀ |
| (CH₂)₃ | O | — | 0 | CH₃ |
| (CH₂)₃ | O | CH₂ | 1 | 4-piperidyl |
| CH₂CH(CH₃) | O | CH₂ | 1 | CH₃ |
| CH₂CH(CH₃) | O | CH(CH₃)CH₂ | 1 | C₆H₅ |
| CH₂CH(CH₃) | O | CH(CH₃)CH₂ | 1 | CH₃ |
| CH(CH₃)(CH₂)₂ | O | — | 0 | cyclohexyl |
| CH(CH₃)(CH₂)₂ | O | — | 0 | 3-piperidyl |
| CH(CH₃)(CH₂)₂ | O | — | 0 | 2-(4-ClC₆H₄)C₄H₆ |
| CH(CH₃)CH₂ | O | (CH₂)₄ | 1 | CH₃ |
| CH(CH₃)CH₂ | O | C(CH₃)₂ | 1 | CH₃ |
| CH(CH₃)CH₂ | O | (CH₂)₆ | 1 | C₆H₅ |
| CH(CH₃)CH₂ | O | CH(CH₃)CH₂ | 1 | 4-piperidyl |
| CH(C₂H₅)CH₂ | O | (CH₂)₂ | 1 | 4-pyridyl |
| CH(C₂H₅)(CH₂)₂ | O | (CH₂)₄ | 1 | 4-FC₆H₄ |
| CH(C₂H₅)(CH₂)₂ | O | CH(CH₃) | 1 | 2-pyridyl |
| CH(C₂H₅)(CH₂)₂ | O | (CH₂)₂ CH(CH₃) | 1 | cycloheptyl |
| (CH₂)₄ | O | — | 0 | CH₃ |
| (CH₂)₄ | O | — | 0 | cyclobutyl |
| (CH₂)₄ | O | — | 0 | 4-ClC₆H₄ |
| (CH₂)₄ | O | CH₂ | 1 | 4-FC₆H₄ |
| (CH₂)₄ | O | CH₂ | 1 | 4-pyridyl |
| (CH₂)₄ | O | CH₂CH(CH₃) | 1 | 4-(C₆H₅)C₆H₁₀ |
| (CH₂)₄ | O | CH(CH₃)CH₂ | 1 | C₆H₅ |
| (CH₂)₄ | O | (CH₂)₅ | 1 | 4-ClC₆H₄ |
| (CH₂)₃ | S | — | 0 | C₆H₅ |
| (CH₂)₃ | S | — | 0 | cyclopentyl |
| (CH₂)₃ | S | — | 0 | 2-piperidyl |
| (CH₂)₃ | S | CH₃ | 1 | C₆H₅ |
| (CH₂)₃ | S | (CH₂)₂ | 1 | CH₃ |
| (CH₂)₃ | S | (CH₂)₄ | 1 | cyclohexyl |
| CH(CH₃)(CH₂)₂ | S | — | 0 | C₆H₅ |
| CH(CH₃)(CH₂)₂ | S | — | 0 | 3-pyridyl |
| CH(CH₃)(CH₂)₂ | S | — | 0 | cyclopropyl |
| CH(CH₃)(CH₂)₂ | S | CH₂ | 1 | C₆H₅ |
| CH(CH₃)(CH₂)₂ | S | (CH₂)₄ | 1 | CH₃ |
| CH(C₂H₅)(CH₂)₂ | S | — | 0 | 4-FC₆H₄ |
| CH(C₂H₅)(CH₂)₂ | S | — | 0 | 4-(C₆H₅)C₆H₁₀ |
| CH(C₂H₅)(CH₂)₂ | S | CH(CH₃) | 1 | 4-ClC₆H₄ |
| CH(C₂H₅)(CH₂)₂ | S | (CH₂)₂CH(CH₃) | 1 | C₆H₅ |
| CH(CH₃)(CH₂)₃ | O | — | 0 | C₆H₅ |
| CH(CH₃)(CH₂)₃ | O | — | 0 | 4-pyridyl |
| CH(CH₃)(CH₂)₃ | O | (CH₂)₂ | 1 | C₆H₅ |
| CH(CH₃)(CH₂)₃ | O | (CH₂)₂ | 1 | 4-pyridyl |

-continued

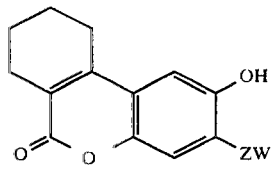

| | | | | |
|---|---|---|---|---|
| CH(CH$_3$)(CH$_2$)$_3$ | S | — | 0 | C$_6$H$_5$ |
| CH(CH$_3$)(CH$_2$)$_3$ | S | — | 0 | CH$_3$ |
| CH(CH$_3$)(CH$_2$)$_3$ | S | (CH$_2$)$_4$ | 1 | C$_6$H$_5$ |
| CH(CH$_3$)(CH$_2$)$_3$ | S | (CH$_2$)$_4$ | 1 | 4-FC$_6$H$_5$ |
| — | S | CH(CH$_3$)CH(CH$_3$)(CH$_2$)$_4$ | 1 | CH$_3$ |
| — | S | (CH$_2$)$_4$ | 1 | CH$_3$ |
| — | S | CH$_2$ | 1 | C$_6$H$_5$ |
| — | S | (CH$_2$)$_2$ | 1 | C$_6$H$_5$ |
| — | S | CH$_2$ | 1 | cyclopropyl |
| — | S | (CH$_2$)$_5$ | 1 | cyclohexyl |
| — | S | (CH$_2$)$_4$ | 1 | cycloheptyl |
| — | S | CH$_2$ | 1 | 2-piperidyl |
| — | S | (CH$_2$)$_3$ | 1 | 4-piperidyl |
| — | S | (CH$_2$)$_3$ | 1 | 3-pyridyl |
| — | S | —CH(CH$_3$)(CH$_2$)$_3$ | 1 | 4-pyridyl |
| — | S | (CH$_2$)$_4$ | 1 | 4-FC$_6$H$_4$ |
| — | S | — | 0 | C$_6$H$_5$ |
| — | S | — | 0 | 4-FC$_6$H$_4$— |
| — | S | — | 0 | 4-ClC$_6$H$_4$ |
| — | S | — | 0 | cyclopropyl |
| — | S | — | 0 | cyclohexyl |
| — | S | — | 0 | 4-pyridyl |
| — | S | — | 0 | 2-pyridyl |
| — | S | — | 0 | 2-piperidyl |
| — | S | — | 0 | 4-(C$_6$H$_5$)C$_6$H$_{10}$ |
| — | S | — | 0 | CH$_3$ |
| — | O | (CH$_2$)$_9$ | 1 | CH$_3$ |
| — | O | (CH$_2$)$_9$ | 1 | C$_6$H$_5$ |
| — | O | CH(CH$_3$)CH$_2$ | 1 | 2-pyridyl |
| — | O | (CH$_2$)$_3$ | 1 | 4-FC$_6$H$_4$ |
| — | O | CH(CH$_3$)(CH$_2$)$_2$ | 1 | 4-piperidyl |
| — | O | CH$_2$ | 1 | 4-FC$_6$H$_4$ |
| — | O | — | 0 | cyclohexyl |
| — | O | — | 0 | cyclopropyl |
| — | O | — | 0 | 4-pyridyl |
| — | O | — | 0 | 3-(C$_6$H$_5$)C$_7$H$_{12}$ |
| — | O | CH$_2$ | 1 | CH$_3$ |
| — | O | (CH$_2$)$_3$ | 1 | CH$_3$ |
| — | O | (CH$_2$)$_6$ | 1 | CH$_3$ |

EXAMPLE 16 dl-7,8,9,10-Tetrahydro-2-hydroxy-6,6-dimethyl-3-(1-methyl-4-phenylbutyl)-6H-dibenzo[b,d]pyran Under a nitrogen atmosphere a solution of 2.00 g. (5.5 mmoles) of dl-7,8,9,10-tetrahydro-2-hydroxy-3-(1-methyl-4-phenylbutyl)-2-oxo-6H-dibenzo[b,d]pyran in ml. of ether was added dropwise to a solution of methyl magnesium iodide prepared from 1.40 g. (57.4 mmoles) of magnesium turnings and 3.43 ml. (55.2 mmoles) of methyl iodide in 50 ml. of ether. After the addition was completed the reaction mixture was heated at reflux overnight, cooled in an ice bath, treated carefully with 1 N hydrochloric acid (6.3 ml.) followed by 6 N hydrochloric acid (23.3 ml.). The acidified mixture was stirred at room temperature for 1.5 hours, the ether layer separated, washed with 2×50 ml. of water and 50 ml. of saturated sodium bicarbonate solution, dried (MgSO$_4$) and concentrated to a dark oil. Silica gel chromatography of the oil, eluting with benzene, gave 1.74 g. (84%) of the title compound as a liquid; $^1$H-NMR (CDCl$_3$)ppm.($\delta$): 7.3–7.0 (m,5,phenyl), 6.6 and 6.4 (s,1,aromatic), 4.8 (s,1,phenolic), 3.1–2.7 (m,1,benzylic CH), 2.4 (broad t,2,benzylic CH$_2$), 2.3–1.8 (m,4,allylic CH$_2$), 1.1 (s,6,gem-dimethyl); IR(CHCl$_3$),$\mu$: 2.8, 3.45; Mass spectrum (m/e): 376 (M+), 361 (M-15).

EXAMPLE 17

Employing the procedures of Examples 7 or 8 starting with the products provided in Examples 14 and 15, the following compounds are similarly prepared wherein R$_4$ and R$_5$ are the same.

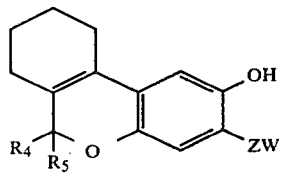

| $R_4 = R_5 =$ | Z | W |
|---|---|---|
| H | —CH(CH₃)(CH₂)₃— | C₆H₅ |
| C₂H₅ | —CH(CH₃)(CH₂)₃— | C₆H₅ |
| n-C₃H₇ | —CH(CH₃)(CH₂)₃— | C₆H₅ |
| n-C₄H₉ | —CH(CH₃)(CH₂)₃— | C₆H₅ |
| H | —CH(CH₃)CH₂— | cyclopropyl |
| CH₃ | —(CH₂)₃— | 2-pyridyl |
| C₂H₅ | —(CH₂)₃— | 3-pyridyl |
| n-C₃H₇ | —CH(CH₃)(CH₂)₃— | 4-pyridyl |
| n-C₄H₉ | —(CH₂)₄— | 3-piperidyl |
| H | —CH₂CH(CH₃)CH₂— | 4-piperidyl |
| CH₃ | —CH(CH₃)CH(CH₃)CH₂— | 3-piperidyl |
| C₂H₅ | —CH(CH₃)(CH₂)₇— | C₆H₅ |
| n-C₃H₇ | —CH(CH₃)(CH₂)₃— | 4-FC₆H₄ |
| n-C₄H₉ | —CH(CH₃)(CH₂)₄— | 4-ClC₆H₄ |
| H | —CH(CH₃)(CH₂)₂— | cycloheptyl |
| CH₃ | —CH(CH₃)(CH₂)₂CH(CH₃)— | 4-piperidyl |
| C₂H₅ | —CH(CH₃)(CH₂)₂O— | C₆H₅ |
| n-C₃H₇ | —(CH₂)₃O— | 4-(C₆H₅)C₆H₁₀ |
| n-C₄H₉ | —(CH₂)₃O— | CH₃ |
| H | —(CH₂)₃OCH₂— | 4-piperidyl |
| CH₃ | —CH₂CH(CH₃)OCH(CH₃)CH₂— | C₆H₅ |
| C₂H₅ | —CH(CH₃)(CH₂)₂O— | 3-piperidyl |
| n-C₃H₇ | —CH(CH₃)(CH₂)₂O— | 2-(4-ClC₆H₄)C₄H₆ |
| n-C₄H₉ | —CH(CH₃)CH₂O(CH₂)₄— | CH₃ |
| H | —CH(CH₃)CH₂OC(CH₃)₂— | CH₃ |
| CH₃ | —CH(CH₃)CH₂O(CH₂)₆— | C₆H₅ |
| C₂H₅ | —CH(C₂H₅)CH₂O(CH₂)₂— | 4-pyridyl |
| n-C₃H₇ | —CH(C₂H₅)(CH₂)₂O(CH₂)₂CH(CH₃)— | cycloheptyl |
| n-C₄H₉ | —(CH₂)₄O— | CH₃ |
| H | —(CH₂)₄O— | 4-ClC₆H₄ |
| CH₃ | —(CH₂)₄OCH₂— | 4-FC₆H₄ |
| C₂H₅ | —(CH₂)₄O(CH₂)₅— | 4-ClC₆H₄ |
| n-C₃H₇ | —(CH₂)₃S— | C₆H₅ |
| n-C₄H₉ | —(CH₂)₃S— | cyclopentyl |
| H | —(CH₂)₃S— | 2-piperidyl |
| CH₃ | —(CH₂)₃SCH₂— | C₆H₅ |
| C₂H₅ | —(CH₂)₃S(CH₂)₂— | CH₃ |
| n-C₃H₇ | —CH(CH₃)(CH₂)₂S— | C₆H₅ |
| n-C₄H₉ | —CH(CH₃)(CH₂)₂S— | cyclopropyl |
| H | —CH(CH₃)(CH₂)₂SCH₂— | C₆H₅ |
| CH₃ | —CH(C₂H₅)(CH₂)₂S— | 4-FC₆H₄ |
| C₂H₅ | —CH(C₂H₅)(CH₂)₂S— | 4-(C₆H₅)C₆H₁₀ |
| n-C₃H₇ | —CH(CH₃)(CH₂)₃O— | C₆H₅ |
| n-C₄H₉ | —CH(CH₃)(CH₂)₃O— | 4-pyridyl |
| H | —CH(CH₃)(CH₂)₃O(CH₂)₂— | C₆H₅ |
| CH₃ | —CH(CH₃)(CH₂)₃S— | C₆H₅ |
| C₂H₅ | —CH(CH₃)(CH₂)₃S(CH₂)₄— | C₆H₅ |
| n-C₃H₇ | —SCH(CH₃)CH(CH₃)(CH₂)₄— | CH₃ |
| n-C₄H₉ | —SCH₂— | C₆H₅ |
| H | —S(CH₂)₂— | C₆H₅ |
| CH₃ | —SCH₂— | cyclopropyl |
| C₂H₅ | —S(CH₂)₅— | cyclohexyl |
| n-C₃H₇ | —S(CH₂)₄— | cycloheptyl |
| n-C₄H₉ | —SCH₂— | 2-piperidyl |
| H | —SCH(CH₃)(CH₂)₃— | 4-pyridyl |
| CH₃ | —S(CH₂)₄— | 4-FC₆H₄ |
| C₂H₅ | —S— | C₆H₅ |
| n-C₃H₇ | —S— | 4-ClC₆H₄ |
| n-C₄H₉ | —S— | cyclohexyl |
| H | —S— | 4-pyridyl |
| CH₃ | —S— | 2-piperidyl |
| C₂H₅ | —S— | 4-(C₆H₅)C₆H₁₀ |
| n-C₃H₇ | —S— | CH₃ |

The remaining compounds provided in Example 15 are reacted in the same manner to provide compounds of the above structure.

dl-cis-6a,7,8,9,10,10a-Hexahydro-2-hydroxy-6,6-dimethyl-3-(1-methyl-4-phenylbutyl)-6H-dibenzo[b,d]-
pyran To a solution of 1.0 g. of dl-7,8,9,10-tetrahydro-2-hydroxy-6,6-dimethyl-3-(1-methyl-4-phenylbutyl)-6H-dibenzo[b,d]pyran in 75 ml. of ethanol is added 200 mg. of 5% palladium-on-carbon catalyst and the resulting mixture is hydrogenated at room temperature and 60 psig. (4.3 kg./cm²) until the theoretical amount of hydrogen is consumed. After filtering to remove the catalyst, the solvent was evaporated to provide the desired 6a,10a-cis compound.

The compounds provided in Example 17 are similarly hydrogenated to provide the corresponding 6a,10a-cis compounds of the formula:

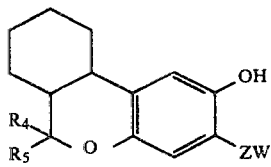

EXAMPLE 19 dl-7,8,9,10-Tetrahydro-2-hydroxy-6,6-dimethyl-3-(1-methyl-4-phenylbutyl)-6H-dibenzo[b,d]pyran As an alternative to the procedure of Example 16, the title compound may be prepared by Wolff-Kishner reduction of the 10-keto compound.

dl-7,8,9,10-Tetrahydro-2-hydroxy-6,6-dimethyl-3-(1-methyl-4-phenylbutyl)-10-oxo-6H-dibenzo[b,d]pyran (780 mg. 2 mmoles.) is added to a solution of 0.25 g. of 85% potassium hydroxide and 0.30 ml. of 85% hydrazine hydrate in 7.5 ml. of diethylene glycol. The mixture is warmed cautiously until any exothermic reaction subsides and then heated at reflux for one hour. The condenser is then set for distillation and distillate taken off until the internal temperature reaches 205° C. The mixture is then refluxed at 190°–205° C. for 3 hours, cooled to 100° C., poured into water and acidified with hydrochloric acid. After extraction with ether, drying and evaporation of solvent the crude title compound is obtained. It may be purified by column chromatography on silica gel, if desired.

EXAMPLE 20 dl-cis-6a,7,8,9,10,10a-Hexahydro-2-hydroxy-6,6-dimethyl-3-(1-methyl-4-phenylbutyl)-6H-dibenzo[b,d]pyran and the corresponding dl-trans-isomer.

As an alternate to the procedure of Example 18, each of the title compounds is obtained by reduction of the corresponding 10-keto compound provided in Example 9 by the procedure of Example 19. Thus, the dl-cis-compound of Example 9, Part A is converted to dl-cis-6a,7,8,9,10,10a-hexahydro-2-hydroxy-6,6-dimethyl-3-(1-methyl-4-phenylbutyl)-6H-dibenzo[b,d]pyran, and the starting material provided in Example 9, Part B provides the above dl-trans title compound.

In a similar manner each of the 6a,10a-cis and 6a,10a-trans-isomers provided in Example 10 are reduced to obtain the corresponding compounds of the formula

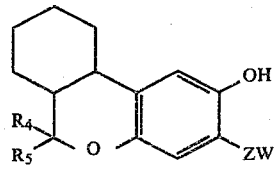

EXAMPLE 21 dl-7,8,9,10-Tetrahydro-2,10α-dihydroxy-6,6-dimethyl-3-(1-methyl-4-phenylbutyl)-6H-dibenzo[b,d]pyran and dl-7,8,9,10-Tetrahydro-2,10β-dihydroxy-6,6-dimethyl-3-(1-methyl-4-phenylbutyl)-6H-dibenzo[b,d]pyran A mixture of 1.00 g. (2.66 mmoles) of dl-7,8,9,10-tetrahydro-2-hydroxy-6,6-dimethyl-3-(1-methyl-4-phenylbutyl)-6H-dibenzo[b,d]pyran and 295 mg. of selenium dioxide in 20 ml. of dioxane were stirred under a nitrogen atmosphere for 13 days. The mixture was concentrated, diluted with 75 ml. of chloroform and filtered to remove precipitated red selenium. The filtrate was concentrated and the residue chromatographed on a column containing 100 g. of silica gel. A column volume of benzene was eluted, then elution started with 3:1 benzene/ether collecting 17 ml. fractions. Early fractions were found to contain 0.54 g. of starting material. Fractions 20–22 contained 39 mg. of one of the title diastereomers of $R_f$ 0.36 upon thin layer chromatography on silica gel plates employing 1:1 benzene/ether solvent system. Upon two crystallizations from ether this product afforded white crystals; M.P. 185°–186° C.; $^1$H-NMR (perdeuteroacetone)ppm. (δ): 7.53 variable (s,1,phenolic), 7.4–7.0 (m,5,phenyl), 7.04 and 7.50 (s,1,aromatic), 4.54–4.32 (m,1,allylic CH), 3.65 variable (d,1,J=7, alcoholic), 1.32 and 1.23 (s,3,gem-methyls), 1.15 (d,3,J=7, α-CH₃); IR(KBr), μ: 3.12, 3.45, 7.05, 7.88, 8.40, 8.65, 9.52, 10.80; Mass spectrum (m/e): 392 (M+).

Anal. Calc'd for $C_{26}H_{32}O_3$: C, 79.55; H, 8.22. Found: C, 79.48; H, 8.49.

Fractions 29–35 were combined, evaporated to dryness and the residual solid triturated with ether to afford 51 mg. of the other title compound, M.P. 176°–179° C. Recrystallization from dichloromethane/ether provided an analytical sample, M.P. 183°–184.5° C. The NMR and infrared spectrum were found to be identical to those of the above, earlier eluting, isomer.

Anal. Calc'd. for $C_{26}H_{32}O_3$: C, 79.55; H, 8.22. Found: C, 79.33; H, 8.25.

Intermediate fractions 23–28 and the mother liquors from above were combined and concentrated to dryness to afford 0.24 g. of a foam which was shown to contain approximately equal amounts of the two isomers by thin layer chromatography.

EXAMPLE 22

A solution of 1.00 g. of dl-7,8,9,10-tetrahydro-2-hydroxy-6,6-dimethyl-3-(1-methyl-4-phenylbutyl)-10-oxo-6H-dibenzo[b,d]pyran in 25 ml. of ethanol is reduced with sodium borohydride by the procedure of Example 11 to produce a mixture of isomeric 10α-ol and 10β-ol compounds. Upon separation by silica gel chromatography as described in Example 15 dl-7,8,9,10-tetrahydro-2,10α-dihydroxy-6,6-dimethyl-3-(1-methyl-4-phenylbutyl)-6H-dibenzo[b,d]pyran and the corresponding 2,10β-diol compound are obtained.

EXAMPLE 23

Sodium borohydride reduction of the products provided in Examples 7 and 8 by the procedure of Example 11 affords a mixture of the corresponding 10α-ol and 10β-ol compounds of the structure below which can be separated by silica gel chromatography as described in Example 21.

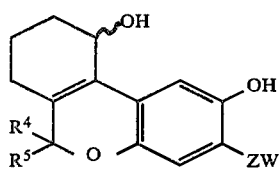

Alternatively, the same compounds are obtained by selenium dioxide oxidation of each of the products of Example 17 by the procedure of Example 21.

EXAMPLE 24

Selenium dioxide oxidation of the compounds provided in Example 17 by the procedure of Example 21 and separation of the resulting mixture of diastereomers by silica gel chromatography as also described in Example 21 provides the corresponding 10α-ol and 10β-ol diasteromers of the formula

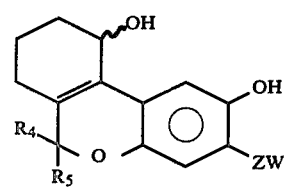

| $R_4=R_5=$ | Z | W |
|---|---|---|
| H | —(CH$_2$)$_6$— | C$_6$H$_5$ |
| H | —CH(CH$_3$)(CH$_2$)$_5$— | cyclohexyl |
| H | —CH(CH$_3$)(CH$_2$)$_7$— | C$_6$H$_5$ |
| H | —(CH$_2$)— | 4-ClC$_6$H$_4$ |
| H | —(CH$_2$)$_3$— | 2-pyridyl |
| H | —CH(CH$_3$)CH$_2$CH(C$_2$H$_5$)— | C$_6$H$_5$ |
| H | —(CH$_2$)$_3$—O— | C$_6$H$_5$ |
| H | —(CH$_2$)$_3$—OCH$_2$— | CH$_3$ |
| H | —(CH$_2$)$_3$—OCH(CH$_3$)— | 4-piperidyl |
| H | —CH(C$_2$H$_5$)(CH$_2$)$_2$—O— | 2-(4-FC$_6$H$_4$)C$_7$H$_{12}$ |
| H | —(CH$_2$)$_4$—O—(CH$_2$CH(CH$_3$)— | 4-(C$_6$H$_5$)C$_6$H$_{10}$ |
| H | —(CH$_2$)$_3$—S— | cyclopropyl |
| H | —(CH$_2$)$_3$—S—CH$_2$— | cyclopentyl |
| H | —CH(C$_2$H$_5$)(CH$_2$)$_2$—S(—CH$_2$)$_2$CH(CH$_3$)— | 4-pyridyl |
| H | —S(CH$_2$)$_8$— | CH$_3$ |
| H | —SCH$_2$— | C$_6$H$_5$ |
| H | —O— | CH$_3$ |
| CH$_3$ | —O— | C$_6$H$_5$ |
| CH$_3$ | —CH(C$_2$H$_5$)(CH$_2$)$_3$— | C$_6$H$_5$ |
| CH$_3$ | —(CH$_2$)$_4$OCH$_2$ | 3-pyridyl |
| CH$_3$ | —(CH$_2$)$_8$— | 4-FC$_6$H$_4$ |
| CH$_3$ | —(CH$_2$)$_3$— | cyclopentyl |
| CH$_3$ | —(CH$_2$)— | 4-ClC$_6$H$_4$ |
| CH$_3$ | —(CH$_2$)$_4$— | 4-pyridyl |
| CH$_3$ | —(CH$_2$)$_3$—O(CH$_2$)$_2$— | 4-pyridyl |
| CH$_3$ | —CH(CH$_3$)(CH$_2$)$_2$OCH$_2$CH(C$_2$H$_5$) | cyclohexyl |
| CH$_3$ | —CH(CH$_3$)(CH$_2$)$_2$S(CH$_2$)$_4$ | CH$_3$ |
| CH$_3$ | —SC(CH$_3$)$_2$(CH$_2$)$_5$— | CH$_3$ |
| C$_2$H$_5$ | —(CH$_2$)$_8$— | 2-ClC$_6$H$_4$ |
| C$_2$H$_5$ | —(CH$_2$)$_4$— | 3-pyridyl |
| C$_2$H$_5$ | —(CH$_3$)$_2$C(CH$_2$)$_5$— | C$_6$H$_5$ |
| C$_2$H$_5$ | —(CH$_2$)$_3$S— | 4-(4-ClC$_6$H$_4$)C$_6$H$_{10}$ |
| C$_2$H$_5$ | —CH(C$_2$H$_5$)(CH$_2$)$_2$S— | C$_6$H$_5$ |
| C$_2$H$_5$ | —CH(CH$_3$) (CH$_2$)$_3$O— | 2-(4-FC$_6$H$_4$)C$_5$H$_8$ |
| C$_2$H$_5$ | —SCH(CH$_3$) (CH$_2$)— | 4-ClC$_6$H$_4$ |
| C$_2$H$_5$ | —S— | CH$_3$ |
| C$_2$H$_5$ | —O— | cyclohexyl |
| n-C$_3$H$_7$ | —CH(CH$_3$) (CH$_2$)$_6$— | 4-FC$_6$H$_4$ |
| n-C$_3$H$_7$ | —CH(CH$_3$)— | C$_6$H$_5$ |
| n-C$_3$H$_7$ | —(CH$_2$)$_4$O(CH$_2$)$_5$ | 3-piperidyl |
| n-C$_3$H$_7$ | —SCH(CH$_3$)(CH$_2$)$_5$— | CH$_3$ |
| n-C$_3$H$_7$ | —S(CH$_2$)$_4$ | 2-pyridyl |
| n-C$_3$H$_7$ | —S— | 3-(C$_6$H$_5$)C$_7$H$_{12}$ |
| n-C$_3$H$_7$ | —O— | 4-piperidyl |
| n-C$_4$H$_9$ | —O— | 3-(C$_6$H$_5$)C$_7$H$_{12}$ |
| n-C$_4$H$_9$ | —CH$_2$CH(CH$_3$)(CH$_2$)$_2$— | C$_6$H$_5$ |
| n-C$_4$H$_9$ | —(CH$_2$)$_3$S(CH$_2$)$_2$— | 4-ClC$_6$H$_4$ |
| n-C$_4$H$_9$ | —CH(CH$_3$)(CH$_2$)$_3$S(CH$_2$)$_4$— | CH$_3$ |
| n-C$_4$H$_9$ | —SCH(CH$_3$)(CH$_2$)$_3$— | C$_6$H$_5$ |
| n-C$_4$H$_9$ | —SCH$_2$ | cyclohexyl |
| n-C$_4$H$_9$ | —S— | C$_6$H$_5$ |

EXAMPLE 25 dl-7,8,9,10-Tetrahydro-2-hydroxy-6-methyl-3-(1-methyl-4-phenylbutyl)-6H-di-benzo[b,d]pyran A solution of 25.6 g. (0.10 mole) 2-(2′,5′-dihydroxyphenyl)-5-phenylpentane and 14.0 g. (0.10 mole) of 2-acetylcyclohexanone in 75 ml. of glacial acetic acid is cooled to 15° C. and anhydrous hydrogen chloride gas is passed through the solution for 30 minutes. The resulting red solution is allowed to warm to room temperature and stirred for four days. The solution is then added to a suspension of 40 g. of sodium bicarbonate in 500 ml. of methanol at −5° C. and the resulting mixture is treated portionwise with 2.0 g. of sodium cyanoborohydride. The mixture is concentrated in vacuo, the residue diluted with water and the aqueous solution extracted with ether (3×300 ml.). The combined extracts are washed with water, 5% aqueous sodium bicarbonate, dried over sodium sulfate and concentrated in vacuo. The residue is dissolved in a solution of 350 ml. of pyridine and 140 g. of acetic anhydride, refluxed for 15 minutes, then allowed to stir at 25° C. overnight. The resulting mixture is again evaporated in vacuo and the residue dissolved in hexane. The solution is washed with water, dilute hydrochloric acid and water, dried ($Na_2SO_4$) and concentrated in vacuo to afford crude dl-7,8,9,10-tetrahydro-2-acetoxy-6-methyl-3-(1-methyl-4-phenylbutyl)-6H-dibenzo[b,d]pyran which is purified by chromatography on silica gel.

The purified 2-acetoxy compound is hydrolyzed by refluxing for 15 minutes with potassium carbonate in 100 ml. of 15% aqueous methanol. The mixture is then diluted with cold water and extracted with ether. The combined ether layers are washed with water, dried ($Na_2SO_4$) and concentrated to dryness afford the title compound.

EXAMPLE 25A dl-5,6,7,8,9,10-Hexahydro-2-hydroxy-6-methyl-3-(1-methyl-4-phenylbutyl)-benzo[c]quinoline A solution of 0.10 mole each of 2-(2′-hydroxy-5′-aminophenyl)-5-phenylpentane and 2-acetylcyclohexanone in 100 ml. of glacial acetic acid is stirred at 50° C. for 30 minutes then cooled to 15° C. and anhydrous hydrogen chloride is passed through the solution for 30 minutes. The resulting solution is stirred at room temperature for two days then added slowly to a suspension of 40 g. of sodium bicarbonate in 500 ml. of methanol at −5° C. and treated with 6.5 g. of sodium cyanoborohydride at room temperature for one hour. The resulting mixture is evaporated to dryness in vacuo, taken up in water and extracted with chloroform. The organic layers are combined, extracted with dilute hydrochloric acid, the aqueous acid phase is separated, made alkaline with sodium hydroxide and extracted with chloroform. The organic extracts are evaporated to dryness and the residue purified by silica gel chromatography to obtain the title compound.

EXAMPLE 25B

By employing the appropriate 2-acylcyclohexanone and 2-(WZ-substituted)hydroquinone or 2-WZ-substituted-p-aminophenol in each case, the following compounds are prepared by the above procedures:

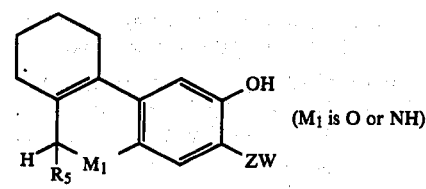

($M_1$ is O or NH)

| $R_5$ | Z | W |
|---|---|---|
| $C_2H_5$ | $-CH(CH_3)(CH_2)_3-$ | $C_6H_5$ |
| $n\text{-}C_3H_7$ | $-CH(CH_3)(CH_2)_3-$ | $C_6H_5$ |
| $n\text{-}C_4H_7$ | $-CH(CH_3)CH_2-$ | cyclopropyl |
| $CH_3$ | $-(CH_2)_3-$ | 2-pyridyl |
| $C_2H_5$ | $-CH_2CH(CH_3)CH_2-$ | 4-piperidyl |
| $n\text{-}C_3H_7$ | $-CH(CH_3)(CH_2)_7-$ | $C_6H_5$ |
| $n\text{-}C_4H_9$ | $-CH(CH_3)(CH_2)_3-$ | $4\text{-}FC_6H_4$ |
| $CH_3$ | $-CH(CH_3)(CH_2)_4-$ | $4\text{-}ClC_6H_4$ |
| $CH_3$ | $-CH(CH_3)(CH_2)_2-$ | cycloheptyl |
| $C_2H_5$ | $-(CH_2)_3O-$ | $4\text{-}(C_6H_5)C_6H_{10}$ |
| $C_2H_5$ | $-(CH_2)_3O-$ | $CH_3$ |
| $n\text{-}C_3H_7$ | $-(CH_2)_3OCH_2-$ | 4-piperidyl |
| $n\text{-}C_3H_7$ | $-CH(CH_3)(CH_2)_2O-$ | $2\text{-}(4\text{-}ClC_6H_4)C_4H_6$ |
| $n\text{-}C_4H_9$ | $-(CH_2)_4O-$ | $CH_3$ |
| $n\text{-}C_4H_9$ | $-(CH_2)_4O-$ | $4\text{-}ClC_6H_4$ |
| $CH_3$ | $-(CH_2)_4O(CH_2)_5-$ | $4\text{-}ClC_6H_4$ |
| $CH_3$ | $-(CH_2)_3S-$ | $C_6H_5$ |
| $CH_3$ | $-(CH_2)_3S-CH_2-$ | $C_6H_5$ |
| $CH_3$ | $-CH(CH_3)(CH_2)_2S-$ | cyclopropyl |
| $CH_3$ | $-CH(CH_3)(CH_2)_2SCH_2-$ | $C_6H_5$ |
| $C_2H_5$ | $-CH(CH_3)(CH_2)_3S(CH_2)_4-$ | $C_6H_5$ |
| $C_2H_5$ | $-SCH_2-$ | $C_6H_5$ |
| $C_2H_5$ | $-S(CH_2)_5-$ | cyclohexyl |
| $CH_3$ | $-S-$ | $C_6H_5$ |
| $C_2H_5$ | $-S-$ | cyclohexyl |
| $n\text{-}C_3H_7$ | $-S-$ | $CH_3$ |

EXAMPLE 25C dl-5,6,7,8,9,10-Hexahydro-2,10-dihydroxy-6-methyl-3-(1-methyl-4-phenylbutyl)-benzo[c]quinoline A mixture of 3.61 g. (10 mmoles) of dl-5,6,7,8,9,10-hexahydro-2-hydroxy-6-methyl-3-(1-methyl-4-phenylbutyl)-benzo[c]quinoline and 1.11 g. of selenium dioxide in 75 ml. of dioxane are stirred under a nitrogen atmosphere for two weeks. The mixture was evaporated, the residue stirred with 300 ml. of chloroform, filtered to remove precipitated selenium, the filtrate concentrated to obtain a mixture of the 10α, and 10β-isomers of the title compound which can be used as is or the isomers separated by column chromatography on silica gel as described in Example 21.

When the 6-alkyl dibenzopyrans and 6-alkyl benzo[c]quinolines provided in Example 25B are reacted by the above procedure, in each case the corresponding 10-hydroxy compounds are obtained by the following formula:

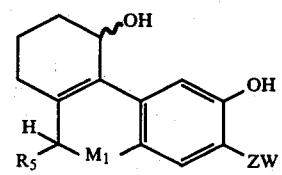

wherein $M_1$, Z, W and $R_5$ have the values shown in Example 25B.

EXAMPLE 25D dl-5,6,7,8,9,10-Hexahydro-2-hydroxy-6-methyl-3-(1-methyl-4-phenylbutyl)-10-oxo-benzo[c]quinoline To a solution of 3.77 g. (10 mmoles) of a mixture of 10α and 10β-isomers of dl-5,6,7,8,9,10-hexahydro-2,10-dihydroxy-6-methyl-3-(1-methyl-4-phenylbutyl)-benzo[c]quinoline in 200 ml. of acetone at −10° C. in a dry nitrogen atmosphere is added 4.2 ml. (11 mmole) of 2.67 M chromic anhydride in dilute sulfuric acid [Jones' reagent, see, e.g., *J. Chem. Soc.*, 3019 (1953)]. After ten minutes at −10° C. the solvent is removed in vacuo, the residue is poured onto an ice-water mixture, made alkaline with sodium hydroxide solution and extracted with ether. The ether extracts are dried (MgSO₄). The dried extracts are evaporated to dryness to obtain the crude product which is purified by column chromatography on silica gel.

The remaining 10-hydroxy compounds provided in Example 25C are reacted by the above procedure or the procedure of Example 21 to obtain the corresponding compounds of the formula

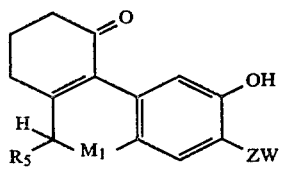

wherein M₁, Z, W and R₅ have the values given in Example 25B.

EXAMPLE 25E

When the compounds provided in Example 25D are reacted with lithium in anhydrous ammonia by the procedure of Example 9A and the isomers separated as by silica gel chromatography the corresponding cis- and trans isomers of the following formula are obtained in each case.

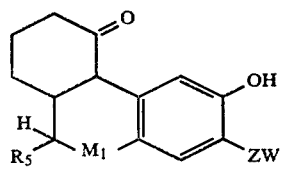

wherein M₁, Z, W and R₅ have the values given in Example 25B.

EXAMPLE 26 dl-7,8,9,19-Tetrahydro-2-hydroxy-6,6-dimethyl-3-(1-methyl-4-phenylbutyl-10-methylene-6H-dibenzo[b,d]pyran A. To 50% sodium hydride/mineral oil (1.52 gm., 32 mmoles), (washed 3×25 ml. portions of pentane) is added 60 ml. of dry dimethylsulfoxide and the mixture heated at 50° C. for 2.5 hours. The heterogeneous mixture turns homogeneous during this heating period. 11.86 (34 mmoles) of methyl triphenylphosphonium bromide is then added in one portion. The yellow solution is heated at 63°-65° C. for 2.5 hours and 1.64 g. (4.2 mmoles) of dl-7,8,9,10-tetrahydro-2-hydroxy-6,6-dimethyl-3-(1-methyl-4-phenylbutyl)-10-oxo-6H-dibenzo[b,d]pyran dissolved in 60 ml. of dimethylsulfoxide is added all at once and heated at 63°-65° C. for an additional 1.5 hours. The reaction is then poured onto 150 ml. ice/water/25 g. NaHCO₃ and extracted 2×50 ml. with ether. The combined ether extracts are dried over MgSO₄, decolorized with charcoal and filtered through a bed of silica gel to afford a crude product which is purified by chromatography on 50 g. silica gel.

B. In a like manner when the compounds provided in Examples 7-10, 25D and 25E are employed as starting material in the above process, the corresponding 10-methylene compounds of the formulae shown below are obtained.

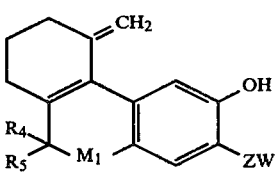

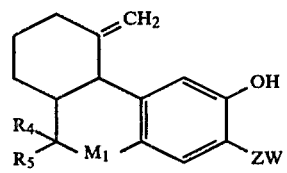

EXAMPLE 27 dl-7,8,9,10-Tetrahydro-2-hydroxy-10-hydroxymethyl-6,6-dimethyl-3-(1-methyl-4-phenylbutyl)-6H-dibenzo[b,d]pyran A. A solution of 0.776 g. (2 mmole) dl-7,8,9,10-tetrahydro-2-hydroxy-6,6-dimethyl-3-(1-methyl-4-phenylbutyl)-10-methylene 6H-dibenzo[b,d]pyran dissolved in 20 ml. of dry tetrahydrofuran is cooled to 0° C. in an ice/water bath. Disiamylborane in tetrahydrofuran (4.2 ml., 2.1 mmoles, 0.5 M solution) is added and the colorless solution allowed to stir overnight at ambient temperature (18 hours). The mixture is cooled in ice and 5 ml. of water added to decompose the excess reagent. It is stirred for 15 minutes and then 2 ml. (6 mmoles) of 3 N sodium acetate followed by 2 ml. 30% hydrogen peroxide added. It is stirred at 0° C. for 15 minutes then allowed to warm to room temperature and stirred overnight (24 hours). The reaction mixture is poured onto 100 ml. ice/water and then extracted with 2×50 ml. ether. The combined ether extracts are washed with sodium sulfite until negative to starch KI test, dried over MgSO₄ and evaporated to dryness to yield a crude product which is chromatographed on silica gel to afford the purified title compound.

B. In the same manner when each of the 10-methylene compounds of Example 26, Part B are used as starting material in the above procedure, the corresponding 10-hydroxymethyl compounds of the formulae below are obtained.

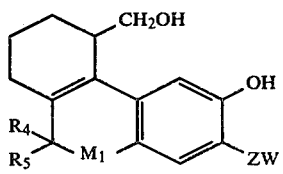

-continued

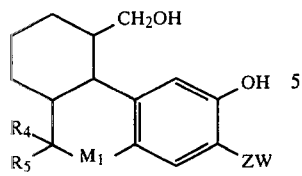

wherein $M_1$ is O or NH and Z, W, $R_4$ and $R_5$ are as set forth in Examples 7–10, 25D and 25E.

Alternatively, the 6α,10α-saturated 10-methylene starting materials are converted to the corresponding 10-hydroxymethyl compounds by employing borane/tetrahydrofuran in place of disiamylborane in tetrahydrofuran.

EXAMPLE 28 dl-7,8,9,10-Tetrahydro-10-acetoxymethyl-2-hydroxy-6,6-dimethyl-3-(1-methyl-4-phenylbutyl)-6H-dibenzo[b,d]pyran A solution of 0.1 mole of dl-7,8,9,10-tetrahydro-2-hydroxy-10-hydroxymethyl-6,6-dimethyl-3-(1-methyl-4-phenylbutyl)-6H-dibenzo[b,d]pyran in 100 ml. of acetonitrile is treated with 0.1 mole of acetic anhydride and the mixture heated for 12 hours under nitrogen. It is then poured onto ice/water and extracted with ethyl acetate (2×100 ml.), the extracts combined, washed with brine and dried $MgSO_4$). Evaporation under reduced pressure followed by silica gel chromatography affords the title product.

Similarly, substitution of anhydrides of propionic, butyric and valeric acid for acetic anhydride affords the corresponding ester derivatives.

EXAMPLE 29 dl-5,6,7,8,9,10-Hexahydro-2-hydroxy-3-(1-methyl-4-phenylbutyl-6-oxo-benzo[c]quinoline In a 100 ml. autoclave is placed a mixture of 7.24 g. (0.020 mole) of dl-7,8,9,10-tetrahydro-2-hydroxy-3-(1-methyl-4-phenylbutyl)-6-oxo-6H-dibenzo[b,d]pyran and 50 ml. of ammonium hydroxide. The mixture is heated at 180° to 200° C. for 40 hours, cooled and acidified with hydrochloric acid. The precipitate is collected by filtration and recrystallized from alchol to obtain the title compound.

When the above procedure is repeated but employing a solution of the appropriate primary amine in place of ammonium hydroxide in each case, the following compounds are obtained in like manner.

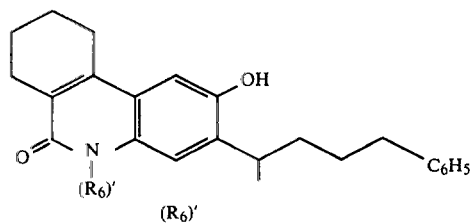

| $(R_6)'$ |
|---|
| $CH_3$ |
| $C_2H_5$ |
| $CH(CH_3)_2$ |
| $CH_2CH_2CH_3$ |
| $CH_2CH(CH_3)$ |
| $CH(CH_3)CH_2CH_3$ |
| $(CH_2)_3CH_3$ |

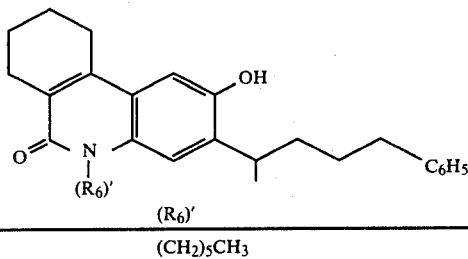

| $(R_6)'$ |
|---|
| $(CH_2)_5CH_3$ |

EXAMPLE 30 dl-5,6,7,8,9,10-Hexahydro-2-hydroxy-3-(1-methyl-4-pehnylbutyl)-5,6,6-trimethyl-benzo[c]quinoline To a refluxing solution of 1.88 g. (5 mmole) of dl-5,6,7,8,9,10-hexahydro-2-hydroxy-5-methyl-3-(1-methyl-4-phenylbutyl)-6-oxo-benzo[c]quinoline in 125 ml. of dry benzene is added over a 5 minute period 16.7 ml. (50 mmole) of a 3 N solution of methylmagnesium bromide in ether and the resulting mixture is heated at reflux for 30 hours. To the cooled (0° C.) mixture is added 50 ml. of 2 N hydrochloric acid. The precipitated solid is collected by filtration. The solid is slurried in water and 6 N sodium hydroxide solution is added to adjust the solution to pH 10–11. The resulting mixture is extracted with chloroform and the extracts evaporated to dryness. The residual crude product is then purified by column chromatography on silica gel.

By employing the appropriate 6-oxo-benzo[c]quinoline selected from those provided in Example 29 and the appropriate Grignard reagent in each case, the following compounds are obtained in a like manner.

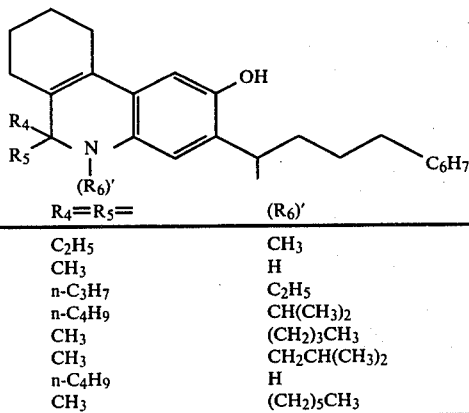

| $R_4=R_5=$ | $(R_6)'$ |
|---|---|
| $C_2H_5$ | $CH_3$ |
| $CH_3$ | H |
| n-$C_3H_7$ | $C_2H_5$ |
| n-$C_4H_9$ | $CH(CH_3)_2$ |
| $CH_3$ | $(CH_2)_3CH_3$ |
| $CH_3$ | $CH_2CH(CH_3)_2$ |
| n-$C_4H_9$ | H |
| $CH_3$ | $(CH_2)_5CH_3$ |

EXAMPLE 31 dl-5,6,7,8,9,10-Hexahydro-2-hydroxy-3-(1-methyl-4-phenylbutyl)-benzo[c]-quinoline To a suspension of 1.0 g. of lithium aluminum hydride in 50 ml. of dry ether is added a solution 3.61 g. (10 mmoles) of dl-5,6,7,8,9,10-hexahydro-2-hydroxy-3-(1-methyl-4-phenylbutyl)-6-oxo-benzo[c]quinoline in 50 ml. of the same solvent. The mixture is heated at reflux for 16 hours and the excess hydride then decomposed by cautious addition of water. The resulting solid is filtered, washed well with ether, the combined ether layers are dried (MgSO₄) and evaporated to dryness to obtain the title compound.

The hydrochloride salt is obtained by dissolving a portion of the free base in ether and passing anhydrous hydrogen chlorine through the cooled solution until precipitation is complete. The resulting precipitate may be purified by recrystallization from alcohol/ether.

EXAMPLE 32

Employing the compounds provided in Example 15 as starting material and reacting each by the procedures of Examples 29, 30 and 31 affords the following compounds wherein $R_4$, $R_5$, $(R_6)$, 'Z and W are as defined in Examples 15, 17, 29 and 30.

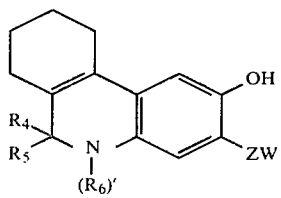

EXAMPLE 33 dl-5,6,7,8,9,10-Hexahydro-6,10-dioxo-2-hydroxy-3-(1-methyl-4-phenylbutyl)-5-methylbenzo[c]quinoline 10-(1,2-dithioethylene)ketal In a sealed tube is placed 9.06 g. (0.020 mole) of dl-7,8,9,10-tetrahydro-6,10-dioxo-2-hydroxy-3-(1-methyl-4-phenylbutyl)-6H-dibenzo[b,d]pyran 10-(1,2-dithioethylene)ketal and 31 g. (0.40 mole) of 40% by weight aqueous methyl amine. The tube is heated at 190°-200° C. for two days then cooled to room temperature. The reaction mixture is evaporated to dryness in vacuo, the residue dissolved in chloroform, washed with water and the solvent evaporated. The residue is recrystallized to obtain the purified title compound When the above procedure is repeated but employing an equivalent amount of ammonium hydroxide or the appropriate primary amine in each case, the following compounds are similarly provided.

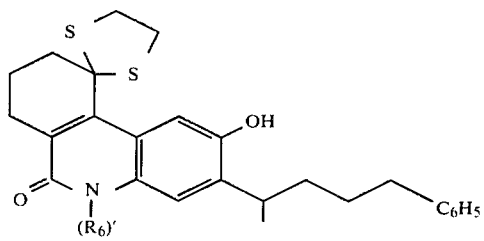

| $(R_6)'$ |
|---|
| H |
| $C_2H_5$ |
| $n-C_3H_7$ |
| $CH(CH_3)_2$ |
| $CH_2CH(CH_3)_2$ |
| $CH(CH_3)CH_2CH_3$ |
| $n-C_6H_{13}$ |

EXAMPLE 34 dl-5,6,7,8,9,10-Hexahydro-2-hydroxy-3-(1-methyl-4-phenylbutyl)-10-oxo-5,6,6-trimethylbenzo[c]quinoline 10-(1,2-dithroethylene)ketal dl-5,6,7,8,9,10-Hexahydro-6,10-dioxo-2-hydroxy-3-(1-methyl-4-phenylbutyl)-5-methylbenzo[c]quinoline 10-(1,2-dithioethylene)ketal (10 mmole) and methylmagnesium iodide (100 mmole) are reacted by the procedure of Example 30 to obtain the title compound.

EXAMPLE 35 dl-5,6,7,8,9,10-Hexahydro-2-hydroxy-3-(1-methyl-4-phenylbutyl)-5-methyl-10-oxo-benzo[c]quinoline 10-(1,2-dithroethylene)ketal The title compound is obtained by reacting dl-5,6,7,8,9,10-hexahydro 6,10-dioxo-2-hydroxy-3-(1-methyl-4-phenylbutyl)-5-methylbenzo[c]quinoline 10-(1,2-dithioethylene)ketal with lithium aluminum hydride by the procedure of Example 31.

EXAMPLE 36 dl-5,6,7,8,9,10-Hexahydro-2-hydroxy-3-(1-methyl-4-phenylbutyl)-10-oxo,5,6,6-trimethylbenzo[c]quinoline The 1,2-dithioethylene ketal provided in Example 34 is reacted with mercuric chloride and cadmium carbonate in water as described in Example 6 to provide the title compound.

EXAMPLE 37 dl-5,6,7,8,9,10-Hexahydro-2-hydroxy-3-(1-methyl-4-phenylbutyl-5-methyl-10-oxo-benzo[c]quinoline The 1,2-dithioethylene ketal provided in Example 35 is reacted with mercuric chloride and cadmium carbonate in water by the procedure of Example 6 to provide the title compound.

EXAMPLE 38

Employing the compounds provided in Example 3 as starting material, protecting the 10-keto group by the procedure of Example 4, reacting the dithioketal obtained with ammonium hydroxide or the appropriate amine by the procedure of Example 33, reacting the product thus obtained either by the procedure of Example 34 but employing the appropriate Grignard reagent or with lithium aluminum hydride by the procedure of Example 35, followed by deprotection by the method of Example 36 and 37, affords the following compounds wherein the values for $R_4$, $R_5$, $(R_6)$, 'Z and W are those given in Examples 10 and 33.

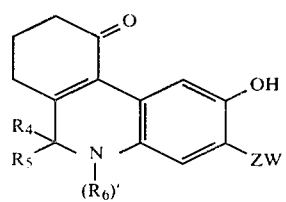

EXAMPLE 39 cis and trans-5,6,6a,7,8,9,10,10a-Octahydro-2-hydroxy-3-(1-methyl-4-phenylbutyl)-10-oxo-5,6,6-trimethylbenzo[c]quinoline Lithium metal, 1.2 g., in 1000 ml. of anhydrous ammonia and 4.03 g. (10 mmole) of 5,6,7,8,9,10-hexahydro-2-hydroxy-3-(1-methyl-4-phenylbutyl)-10-oxo-5,6,6-trimethylbenzo[c]quinoline in 500 ml. of tetrahydrofuran were reacted by the procedure of Example 9 and the resulting mixture of 6a,10a-cis and 6a,10a-trans isomers was isolated and separated by silica gel chromatography as described therein.

When the compounds provided in Example 38 are each reduced with lithium and ammonia and the resulting mixture of cis and trans-isomers are separated in the same manner the following 6a,10a-cis and 6a,10a-trans compounds are obtained.

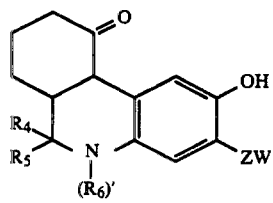

EXAMPLE 40 dl-cis-5,6,6a,7,8,9,10,10a-Octahydro-2,10-dihydroxy-6,6-dimethyl-3-(1-methyl-4-phenylbutyl)-benzo[c]quinoline A solution of 2.5 g. of cis-5,6,6a,7,8,9,10,10a-octahydro-2-hydroxy-6,6-dimethyl-3-(1-methyl-4-phenylbutyl)-10-oxo-benzo[c]quinoline in 100 ml. of methyl alcohol is reduced with sodium borohydride, 600 mg., by the procedure of Example 11 to produce a mixture of isomeric $10\alpha$-ol and $10\beta$-ol compounds. The isomeric mixture is separated, if desired, by silica gel chromatography as described in Example 15.

In a similar manner sodium borohydride reduction of the remaining cis-isomers provided in Example 39 provides the corresponding mixture of cis-$10\alpha$-ol and cis-$10\beta$-ol. Likewise, the trans-isomers provided in Example 39 are reduced to obtain a mixture of trans-$10\alpha$-ol and trans-$10\beta$-ol. The mixtures are separated by silica gel chromatography, if desired. The mixtures thus obtained in each case are of the formula

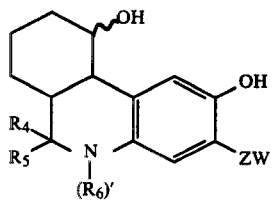

EXAMPLE 41 dl-5,6,7,8,9,10-Hexahydro-2,10-dihydroxy-6,6-dimethyl-3-(1-methyl-4-phenylbutyl)-benzo-[c]quinoline 5,6,7,8,9,10-Hexahydro-2-hydroxy-6,6-dimethyl-3-(1-methyl-4-phenylbutyl)-10-oxo-benzo[c]quinoline is reduced with sodium borohydride in isopropyl alcohol as solvent to provide the title compound as a mixture of $10\alpha$-ol and $10\beta$-ol. The isomers are separated by silica gel chromatography.

In the same manner each of the 10-oxo compounds provided in Examples 36, 37 and 38 are reduced to provide mixtures of the formula

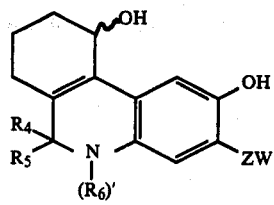

the mixtures are separated by silica gel chromatography to provide the respective $10\alpha$-ol and $10\beta$-ol compounds.

Alternatively, the same compounds are obtained by selenium dioxide oxidation of the compounds provided in Examples 30, 31 and 32 by the procedures of Examples 21 and 25C.

EXAMPLE 42

5,6,6a,7,8,9,10,10a-Octahydro-2-hydroxy-10-hydroxymethyl-6,6-diemthyl-3-(1-methyl-4-phenylbutyl)-benzo[c]quinoline A. 5,6,6a,7,8,9,10,10a-Octahydro-2-hydroxy-6,6-dimethyl-3-(1-methyl-4-phenylbutyl)-10-methylene-benzo[c]quinoline To 50% sodium hydride in mineral oil (3.04 g., 0.064 mole), washed with 3×50 ml. of pentane, is added 120 ml. of dry dimethylsulfoxide and the mixture heated at 50° C. for two hours during which time the mixture becomes homogeneous. Then 23.6 g. (0.068 mole) of methyl triphenylphosphonium bromide is added in one portion and the resulting yellow solution is heated at 65° C. for 2.5 hours. 5,6,6a,7,8,9,10,10a-Octahydro-2-hydroxy-3-(1-methyl-4-phenylbutyl)-6,6-dimethyl-10-oxo-benzo[c]quinoline (3.37 g., 0.0084 mole) dissolved in 120 ml. of dimethylsulfoxide is added all at once and the mixture heated at 63°-65° C. for an additional 1.5 hours. The reaction mixture is poured onto 300 ml. of ice water containing 50 g. of sodium bicarbonate and extracted with ether (2×100 ml.). The ether extracts are dried (MgSO4), carbon tested and filtered through a bed of silica gel to afford the crude 10-methylene compound which is purified by silica gel chromatography.

B. A solution of 0.80 g. (2 mmole) of the 10-methylene compound obtained in Part A, above, is dissolved in 20 ml. of dry tetrahydrofuran and cooled to 0° C. Borane-tetrahydrofuran complex (3.0 ml. of 1 M solution) is added the resulting solution allowed to stir overnight at ambient temerature. The mixture is cooled in ice and water (5 ml.) is added to decompose the excess reagent. The resulting mixture is stirred for 15 minutes and then two ml. of 3 N sodium acetate and two ml. of 30% hydrogen peroxide added. After stirring for 15 minutes at 0° C. the mixture is allowed to warm to room temperature and stirred for 24 hours, poured onto ice/water (100 ml.) and extracted twice with 50 ml. portions of ether. The combined ether extracts are washed with sodium sulfite until negative to the starch-potassium iodide test, dried over magnesium sulfate and evaporated to dryness to yield the crude 10-hydroxymethyl compound which is further purified by silica gel chromatography.

EXAMPLE 43

When each of the benzo[c]quinolines provided in Examples 25E and 39 are employed as starting material in the procedures of Example 42 the corresponding 10-hydroxymethyl compounds are obtained of the formula

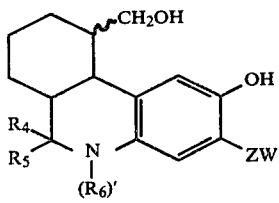

EXAMPLE 44

5,6,7,8,9,10-Hexahydro-2-hydroxy-6,6-dimethyl-3-(1-methyl-4-phenylbutyl)10-methylene-benzo[c]quinoline A 1 N ethereal solution of butyllithium (9 ml.) is added with stirring, under a nitrogen atmosphere to a suspension of 3.57 g. (10 mmoles) of methyltriphenylphosphonium bromide (prepared from methyl bromide and triphenylphosphine) in 50 ml. of ether. 5,6,7,8,9,10-Hexahydro-2-hydroxy-3-(1-methyl-4-phenylbutyl)-6,6-dimethyl-10-oxo-benzo[c]quinoline (600 mg., 1.5 mmoles) dissolved in 100 ml. of ether is added and the mixture is stirred for four hours then allowed to stand overnight at room temperature. Ether is distilled off as tetrahydrofuran is added until most of the ether is replaced. The mixture was then refluxed for six hours, cooled and worked-up as described in Part A of Example 42 to obtain the title compound.

EXAMPLE 45

When each of the α,β-unsaturated-10-keto-benzo[c]quinolines provided in Example 36, 37 and 38 are employed as starting material in the procedure of Example 44, Part A, the corresponding 10-methylene compounds of the following formula are obtained.

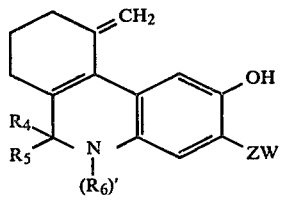

EXAMPLE 46

A solution of 342 mg. (0.86 mmole) of 5,6,7,8,9,10-hexahydro-2-hydroxy-6,6-dimethyl-3-(1-methyl-4-phenylbutyl)-10-methylene-benzo[c]quinoline in 10 ml. of dry tetrahydrofuran is treated at 0° C., under a dry nitrogen atmosphere, with 1.75 ml. of 0.5 M disiamylborane (see e.g., Zweifel et al., J. Am. Chem. Soc., 84, 190, 1962) in tetrahydrofuran and allowed to stand at 0°–5° C. for one hour. Water, 0.25 ml., is added at 0° C. to decompose any excess disiamylborane. The mixture is allowed to warm to room temperature, 0.40 ml of 2.5 N sodium hydroxide and 0.27 ml. of 30% hydrogen peroxide is added and the mixture stirred at room temperature for one hour. The reaction mixture is poured onto ice/water and extracted with ether. The combined extracts are washed with sodium sulfite until negative to starch-potassium iodide test, dried (MgSO4) and evaporated to dryness to provide the crude title compound which is further purified by silica gel chromatography.

EXAMPLE 47

When the 10-methylene compounds obtained in Example 45 are reacted with disiamylborane and oxidized with hydrogen peroxide by the procedure of Example 46, 10-hydroxymethyl compounds of the formula shown below are similarly obtained.

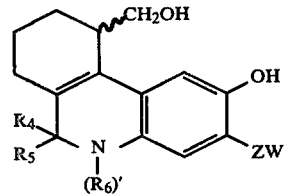

EXAMPLE 48

The 10-keto compounds obtained in Examples 6, 7, 8, 25E, 36, 37, 38 and 39 are reduced by the Wolff-Kishner method of Example 19 to obtain the corresponding compounds of the formulae

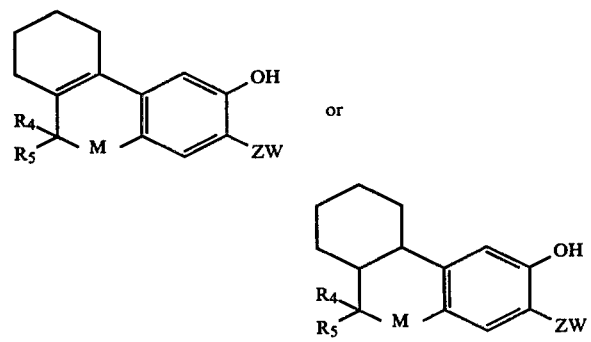

wherein $R_4$, $R_5$, Z and W are as defined for the starting materials and M is O, NH or $N(R_6)'$ where $(R_6)'$ is alkyl having from one to six carbon atoms. For those cases where M is NH or $N(R_6)'$ the product is isolated after the reflux period by acidifying to pH 9.5–10.5, extracting with a water immiscible organic solvent such as ethyl ether, chloroforn or methylene chloride, drying the extracts with anhydrous MgSO4 or Na2SO4, evaporation of solvent and purification of the crude residual product by chromatography, if desired.

EXAMPLE 49

The $\Delta^{6a,10a}$-unsaturated compounds obtained in Examples 25, 25A, 25B and 48 are catalytically hydrogenated by the procedure of Example 18 to obtain the corresponding 6a,10a-cis compounds of the formula

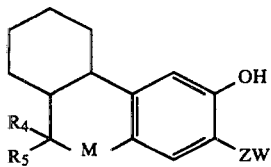

wherein $R_4$, $R_5$, Z, W and M are as defined in Example 48.

EXAMPLE 50

5,6,7,8,9,10-Hexahydro-2-acetoxy-3-(1-methyl-4-phenylbutyl)-6,6-dimethyl-10-oxo-benzo[c]quinoline Pyridine (2.2 ml.) is added to a suspension of 5,6,7,8,9,10-hexahydro-2-hydroxy-3-(1-methyl-4-phenylbutyl)-6,6-dimethyl-10-oxobenzo[c]quinoline (250 mg., 0.642 mmole) in 2.2 ml. of acetic anhydride under a nitrogen atmosphere. The mixture is stirred for 1.5 hours at room temperature and then poured onto ice (50 ml.). The mixture is extracted with ether, the extracts washed with water (4×50 ml.) and brine (1×60 ml.), dried (MgSO4) and evaporated under reduced pressure.

The residue is dissolve in a mininum amount of ether and purified by silica gel chromatography. The fractions containing the title compound are combined and evaporated to dryness.

EXAMPLE 51

The 2-hydroxy-substituted-benzo[b,d]pyrans and benzo[c]quinoline compounds provided by the above procedures are converted to their corresponding 2-acetoxy derivatives by the procedure of Example 50. Compounds having the formulae below are thus prepared wherein the values for Q, M, $R_4$, $R_5$, R, Z and W are as set forth in the Examples for the 2-hydroxy compounds.

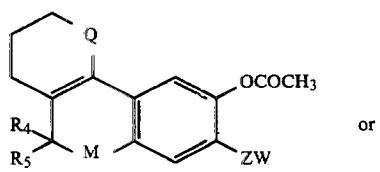

When Q is —CH2OH the product obtained is a diacetate. The corresponding 2-acetoxy-10-hydroxymethyl compound is obtained by mild alkaline hydrolysis in, e.g., 0.1 N ethanolic potassium carbonate at room temperature or hydrolysis under mild acidic conditions, e.g. 0.1 N hydrochloric acid at room temperature.

Substitution of acetic anhydride by benzoic anhydride, propionic anhydride, butyric anhydride or valeric anhydride in the procedure of this Example affords the corresponding isomeric 2-benzoyloxy, 2-propionyloxy, 2-butyryloxy and 2-valeryloxy derivatives. Use of the 2-acetoxy-10-hydroxymethyl compounds, provided above, as starting material affords the corresponding mixed diesters in which the 2-substituent is acetoxy and the 10-substituent is benzoyloxy, propionyloxy, butyryloxy or valeryloxy.

EXAMPLE 52

5,6,6a,7,8,9,10,10a-Octahydro-2-(4-morpholinobutyryloxy)-10-hydroxymethyl-6,6-dimethyl-3-(1-methyl-4-phenylbutyl)benzo[c]quinoline Hydrochloride To a 25° C. solution of 5,6,6a,7,8,9,10,10a-octahydro-2-hydroxy-10-hydroxymethyl-6,6-dimethyl-3-(1-methyl-4-phenylbutyl)benzo[c]quinoline (626 mg., 1.5 mmole) in dry methylene chloride (25 ml.) is added 4-morpholinobutyric acid hydrochloride (0.315 g., 1.5 mmole) and the mixture stirred at room temperature under a nitrogen atmosphere. A 0.1 M solution of dicyclohexylcarbodiimide in methylene chloride (12.5 ml., 1.5 mmole) is added dropwise and the mixture stirred for 6 hours. It is then cooled in ice, filtered and evaporated to give the title product which is purified as the free base by column chromatography on silica gel.

Treatment of the isolated free base with excess of dry hydrogen chloride in ether yields the dihydrochloride salt.

By repetition of the above procedure but employing the appropriate reactant of formula (I) or (II) wherein $R_1$ is hydrogen and the appropriate alkanoic acid or acid of formula $HCl.R_2R_3N(CH_2)_pCOOH$ wherein $R_2$ and $R_3$ are as previously defined affords the following compounds:

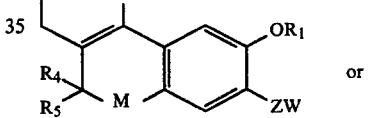

or

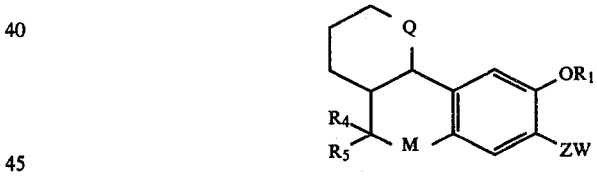

wherein M, Q, Z, W, $R_4$ and $R_5$ are as defined in the above examples and $R_1$ is as shown below.

| $R_1$ |
|---|
| COCH2CH3 |
| CO(CH2)2CH3 |
| CO(CH2)3CH3 |
| COCH2NH2 |
| CO(CH2)2NH2 |
| CO(CH2)4NH2 |
| CO(CH2)N(CH3)2 |
| CO(CH2)2NH(C2H5) |
| CO(CH2)4NHCH3 |
| CONH2 |
| CON(C2H5)2 |
| CON(C4H9)2 |
| CO(CH2)3NH(C3H7) |
| CO(CH2)2N(C4H9)2 |
| COCH2-piperidino |
| COCH2-pyrrolo |
| CO(CH2)2-morpholino |
| CO(CH2)2-N-butylpiperazino |
| CO(CH2)3-pyrrolidino |
| CO-piperidino |
| CO-morpholino |

| R₁ |
|---|
| CO-pyrrolo |
| CO-N-(methyl)piperazino |
| CO-C₆H₅ |
| COCH(CH₃)(CH₂)₂-piperidino |

Basic esters are obtained as their hydrochloride salts. Careful neutralization with sodium hydroxide affords the free basic esters.

EXAMPLE 53 dl-5,6,7,8,9,10-Hexahydro-2-acetoxy-3-(1-methyl-4-phenylbutyl)-5-benzoyl-6,6-dimethyl-10-oxo-benzo[c]quinoline To a stirred solution of the product of Example 50, 5,6,7,8,9,10-hexahydro-2-acetoxy-3-(1-methyl-4-phenylbutyl)-6,6-dimethyl-10-oxo-benzo[c]quinoline (812 mg.) in 2.5 ml. pyridine is added 421 mg. benzoyl chloride in 5 ml. chloroform. After two hours, the reaction mixture is poured onto ice and extracted twice with ether. The combined ether extracts are washed with water, sodium bicarbonate, dried (MgSO₄) and filtered to yield the title compound after concentration and crystallization from ether/petroleum ether.

Repetition of the above procedure but using an equivalent amount of acetyl chloride in place of benzoyl chloride affords the corresponding 2,5-diacetate.

In a like manner the compounds provided in Example 51 and those of Example 52, except those containing a primary or secondary amino group in the R₁ substituent, are reacted with benzoyl, carbobenzyloxy, acetyl, propionyl, butyryl, isobutyryl, valeryl, 2-phenylacetyl or 4-phenylbutyryl chlorides; or ethyl chlorocarbonate or butyl chlorocarbonate to provide the corresponding compounds of the formula:

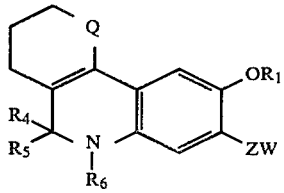 or

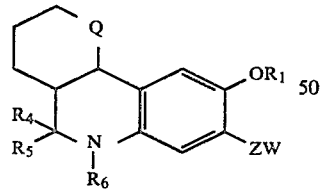

wherein R₄, R₅, Q, ZW and R₁ are as defined in Examples 51 and 52 and R₆ is benzoyl, carbobenzyloxy, acetyl, propionyl, butyryl, isobutyryl, valeryl, 2-phenylacetyl, 4-phenylbutyryl, ethoxycarbonyl or butoxycarbonyl.

EXAMPLE 54 dl-5,6,7,8,9,10-Hexahydro-5-formyl-2-hydroxy-3-(1-methyl-4-phenylbutyl)-6,6-dimethyl-10-oxobenzo[c]quinoline A solution of 5,6,7,8,9,10-hexahydro-2-hydroxy-3-(1-methyl-4-phenylbutyl)-6,6-dimethyl-10-oxo-benzo[c]quinoline (226 g., 0.58 mole) in ethyl formate (1140 g., 14.6 moles) is added dropwise to sodium hydride (72 g., 3.0 moles, obtained by washing 144 g. of 50% sodium hydride with hexane, 3×500 ml.), with good stirring. After about 1.5 hours when ⅔ of the ethyl formate solution is added, the addition is discontinued to allow the vigorous foaming to subside. Diethyl ether (600 ml.) is added and the mixture stirred for 15 minutes before adding the remainder of the ethyl formate solution. When addition is complete, diethyl ether (600 ml.) is added, the reaction mixture stirred for an additional 10 minutes and then poured onto ice water (2 liters). It is acidified to pH 1 with 10% HCl and the aqueous phase separated and extracted with ethyl acetate (2×2 liters). The combined organic solutions are washed successively with water (2×2 liters), brine (1×one liter) and dried (MgSO₄). Concentration to dryness affords the title compound which may be further purified by silica gel chromatography, if desired.

The remaining compounds of formulae (I) and (II) prepared above, wherein R₁ is hydrogen and M is NH are converted to the corresponding N-formyl derivatives in like manner.

EXAMPLE 55 dl-5,6,7,8,9,10-Hexahydro-5-(4-ethoxycarbonylbutyl)-2-hydroxy-3-(1-methyl-4-phenylbutyl)6,6-dimethyl-10-oxo-benzo[c]quinoline To a stirred mixture of 150 ml. toluene, 10 ml. of triethylamine and 4.52 g. (11.6 mmole) of 5,6,7,8,9,10-hexahydro-2-hydroxy-3-(1-methyl-4-phenylbutyl)-6,6-dimethyl-10-oxo-benzo[c]quinoline is added 2.5 g. (12.8 mmole) of ethyl 4-bromobutyrate in 20 ml. of toluene. The resulting mixture is heated at reflux for two hours, cooled, poured onto an ice-water mixture and extracted with ether. The organic extracts are dried (MgSO₄) and evaporated in vacuo to dryness to afford the crude title compound which may be purified by silica gel chromatography, if desired.

When the above procedure is repeated but employing the appropriate ω-bromo ester of the formula Br(CH₂)ᵧCOOAlk₃ (y is 1 to 4 and Alk₃ is alkyl having from one to four carbon atoms) or a corresponding ω-chloro ester in place of ethyl 4-bromobutyrate affords the corresponding compounds of the formula

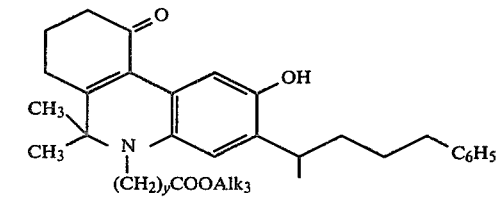

In like manner the remaining compounds of formula (I) and (II) prepared above, wherein M is NH are converted to the corresponding compounds wherein M is NR₆ and R₆ is —(CH₂)ᵧCOOAlk₃ as defined above.

EXAMPLE 56

5,6,7,8,9,10-Hexahydro-2-hydroxy-3-(5-cyclohexylpentylsulfinyl)-6,6-diethylbenzo[c]quinoline Equimolar amounts of m-chloroperbenzoic acid and 5,6,7,8,9,10-hexahydro-2-hydroxy-3-(5-cyclohexylthio)-6,6-diethylbenzo[c]quinoline are added to a mixture of chloroform and acetic acid (2:1 by weight) and the reaction mixture is stirred for one hour at room temperature. The organic phase is then separated, washed with water, dried over anhydrous MgSO₄ and evaporated to dryness to give the title compound.

In like manner the remaining thioethers provided in the previous examples are oxidized to the corresponding sulfoxides of the formulae (I) or (II) where Z is —(alk₁)ₘ—X—(alk₂)ₙ— and X is SO.

EXAMPLE 57

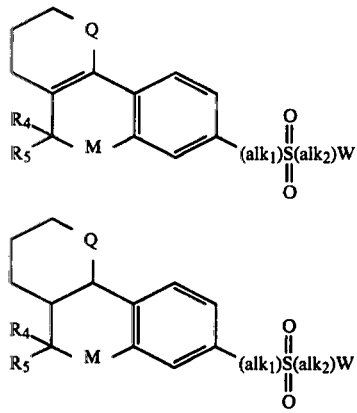

When the procedure of Example 56 is repeated but using two equivalents of m-chloroperbenzoic acid per mole of thioether reactant, a corresponding sulfonyl compound of the appropriate structure, above, is obtained wherein M, Q, W, R₄ and R₅ are all as previously defined.

EXAMPLE 58

General Hydrochloride Salt Formation

Excess hydrogen chloride is passed into a solution of the appropriate compound of formulae I–II wherein M is an amino moiety, NR₆, and/or R₁ is an amine-containing moiety. The resulting precipitate is separated and is recrystallized from an appropriate solvent, e.g. methanol-ether (1:10).

The remaining compounds of formulae I–II wherein M is an amino moiety, NR₆, and/or R₁ is an amine-containing moiety, are converted to their hydrochlorides in like manner.

Similarly, the hydrobromide, sulfate, nitrate, phosphate, acetate, butyrate, citrate, malonate, maleate, fumarate, malate, glycolate, gluconate, lactate, salicylate, sulfosalicylate, succinate, pamoate and tartrate salts are prepared.

EXAMPLE 59

One hundred mg. of dl-7,8,9,10-tetrahydro-2-hydroxy-6,6-dimethyl-3-(1-methyl-4-phenylbutyl)-6H-dibenzo[b,d]pyran are intimately mixed and ground with 900 mg. of starch. The mixture is then loaded into telescoping gelatin capsules such that each capsule contains 10 mg. of drug and 90 mg. of starch.

EXAMPLE 60

A tablet base is prepared by blending the ingredients listed below:

| | |
|---|---|
| Sucrose | 80.3 parts |
| Tapioca starch | 13.2 parts |
| Magnesium stearate | 6.5 parts |

Sufficient dl-7,8,9,10-tetrahydro-2,10α-dihydroxy-6,6-dimethyl-3-(1-methyl-4-phenylbutyl)-6H-dibenzo[b,d]pyran is blended into this base to provide tablets containing 0.5, 1, 5, 10, 25 and 50 mg. of drug.

EXAMPLE 61

Suspensions of dl-5,6,7,8,9,10-hexahydro-2,10-dihydroxy-3-(1-methyl-4-phenylbutyl)benzo[c]quinoline are prepared by adding sufficient amounts of drug to 0.5% methylcellulose to provide suspensions having 0.1, 0.5, 1, 5 and 10 mg. of drug per ml.

PREPARATION A

2-Bromo-5-phenylpentane

To a phosphorus pentabromide, prepared by addition of bromine (9.0 g.) in methylene chloride (10 ml.) to phosphorous tribromide (15.0 g.) in methylene chloride (15 ml.) at 0° C., is added 5-phenyl-2-pentanol (8.2 g.) in methylene chloride at 0° C. The mixture is stirred for 2.5 hours at 0° C. and is then allowed to warm to room temperature. Water (50 ml.) is added, the mixture stirred for one hour and the methylene chloride layer separated. The extraction is repeated and the combined extracts washed with water, saturated sodium bicarbonate solution, brine and then dried over magnesium sulfate. Concentration of the dried extracts gives 12.4 g. of title product as a light yellow oil.

NMR: $\delta_{CDCl_3}^{TMS}$ 1.6 (D, 3, methyl, J=7 Hz), 1.6–2.0 (M, 4, ethylene), 2.3–3.0 (bd, T, 2, benzylic-methylene), 3.7–4.2 (M, 1, methine), 6.9–7.4 (M, 5, aromatic).

PREPARATION B

2-(2',5'-Dimethoxyphenyl)-5-Phenylpentane

A solution of 1-bromopropylbenzene (51.7 g., 0.26 mole) in ether (225 ml.) is added dropwise over a one hour period to a refluxing mixture of magnesium (7.32 g.) in ether (78 ml.). The reaction mixture is refluxed for 30 minutes longer and then a solution of 2,5-dimethoxyacetophenone (50 g.) in ether (60 ml.) is added dropwise and heated to reflux for 1.5 hours. The reaction is quenched by addition of saturated ammonium chloride (250 ml.) the ether layer is separated and the aqueous phase extracted with ether (3×200 ml.). The combined ether extracts are dried over magnesium sulfate and concentrated under vacuum to yield 80.3 g. (100%) of 2-(2'5'-dimethyloxyphenyl)-5-phenyl-2-pentanol as an oil. The oil (78.1 g., 0.26 mole), 21.7 g. of p-toluenesulfonic acid and 1250 ml. of phenol are combined and heated at reflux for one hour, while collecting the water (5.5 ml.) evolved in a Dean-Stark apparatus. The mixture is cooled to room temperature, washed with 200 ml. portions of water, saturated sodium bicarbonate and brine, then dried over magnesium sulfate. The filtered phenol layer yields 75.6 g. of 2-(2',5'-dimethoxyphenyl)-5-phenyl-2-pentene as an orange oil upon evaporation.

A 73.4 g. portion of the orange oil is hydrogenated in a mixture containing ethanol (400 ml.), concentrated hydrochloric acid (2 ml.) and 5% palladium-on-carbon (5 g). The catalyst is filtered off and the ethanol removed under vacuum.yielding 74.0 g. of oil. The oil is distilled at 0.5 mm. pressure, 128°–143° C. to yield 49.7 g. (67%) of product. The major fraction is distilled at 136°-143° C. The NMR spectrum is consistent with the desired product

PREPARATION C

2-(2',5'-Dihydroxyphenyl)-5-phenylpentane

A mixture of 2-(B 2',5'-dimethoxyphenyl)-5-phenylpentane (47.7 g.) and pyridine hydrochloride (203 g.) under nitrogen is heated to 200° C. for 6 hours with vigorous stirring. The reaction mixture is cooled, dissolved in 6 N hydrochloric acid (300 ml.) and diluted with water to 900 ml. The aqueous solution is extracted with ethyl acetate (4×200 ml.), the ethyl acetate extracts dried over sodium sulfate and concentrated under vacuum to yield 50.7 g. of crude product. The crude oil dissolved in benzene is purified by siica gel chromatography, eluting with 95:5 benzene/ether, to yield 36.9 g. of 2-(2',5'-dihydroxyphenyl)-5-phenylpentane.

A portion recrystallized from benzene/hexane melts at 78°-80° C. The NMR spectrum is consistent with that expected for the desired compound.

Following the procedures of Preparation B and C, the compounds listed below are prepared by substituting the appropriate 1-bromoalkylbenzene for 1-bromopropylbenzene:
2-(2,5-(dihydroxyphenyl)-6-phenylhexane,
1-(2,5-dihydroxyphenyl)-2-phenylethane,
2-(2,5-dihydroxyphenyl-4-phenylbutane.

The following compounds are prepared in like manner from the appropriate alcohol and 2,5-dimethoxybenzaldehyde, 2,5-dimethoxyacetophenone or 2,5-dimethoxypropiopiophenone by the methods of Preparation A, B and C:

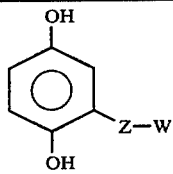

| Z | W* |
|---|---|
| CH(CH₃)CH₂ | C₅H₉ |
| CH(CH₃)(CH₂)₂ | C₅H₉ |
| CH(CH₃)CH₂ | C₃H₅ |
| CH(CH₃)CH(CH₃) | C₆H₁₁ |
| CH(CH₃)(CH₂)₃ | C₆H₁₁ |
| CH(CH₃)(CH₂)₄ | C₅H₉ |
| CH(CH₃)(CH₂)₅ | C₆H₁₁ |
| CH(C₂H₅)(CH₂)₂ | C₆H₁₁ |
| (CH₂)₃ | C₅H₉ |
| CH(C₂H₅)(CH₂)₃ | C₆H₅ |
| CH(CH₃)(CH₂)₇— | C₆H₅ |
| (CH₂)₄ | C₆H₅ |
| (CH₂)₂CH(C₂H₅) | C₆H₅ |
| CH(CH₃)CH₂CH(C₂H₅) | C₆H₅ |

*
C₃H₅ = cyclopropyl
C₅H₉ = cyclopentyl
C₆H₁₁ = cyclohexyl

PREPARATION D

1-(2,5-Dihydroxyphenyl)-2-methyl-4-phenylbutane

A solution of n-butyl lithium (29 ml. of 2.2 M) is added dropwise to 2,5-dimethoxybenzyl triphenylphosphonium bromide (31.5 g.) in tetrahydrofuran (200 ml.) with stirring and the resulting deep red solution is stirred for one-half hour. Benzyl acetone (9.4 g.) is added dropwise and the reaction mixture stirred for 12 hours. It is then adjusted to pH 7 by addition of acetic acid and concentrated under reduced pressure. The residue is extracted with methylene chloride and the extract evaporated to give crude 1-(2,5-dimethoxyphenyl)-2-methyl-4-phenyl-1-butene as an oil. It is purified by chromatography on silica gel and elution with benzene.

The 1-(2,5-kimethoxyphenyl)-2-methyl-4-phenyl-1-butene-(9.4 g.) thus prepared is dissolved in ethanol (250 ml.) and catalytically hydrogenated at 45 p.s.i. in the presence of palladium-on charcoal (1 g. of 10%) and concentrated hydrochloric acid (1 ml.). to obtain 1-(2,5-dimethoxyphenyl)-2-methyl-4-phenylbutane, which is demethylated according to the procedure of Preparation C to give 1-(2,5-dihydroxyphenyl)-2-methyl-4-phenylbutane.

The 2,5-dimethoxybenzyl triphenylphosphonium bromide is prepared by refluxing a mixture of 2,5-dimethoxybenzyl bromide (12 g.) and triphenylphosphine (14.2.) in acetonitrile (200 ml.) for one hour and isolating the product by standard methods.

PREPARATION E

2-Methyl-2-(2,5-dihydroxyphenyl)-5-phenylpentane

To a solution of the Grignard reagent prepared from 2-phenylbromoethane (5.5 g.), magnesium (0.8 g.) and dry ether (60 ml.) is added a solution of 2-methyl-2-(2,5-dimethoxyphenyl)propionitrile (2.75 g.) in dry ether (20 ml.). The ether is distilled off and replaced by dry benzene (50 ml.) and the mixture refluxed for 48 hours. It is then decomposed by careful treatment with dilute sulfuric acid and heated on a steam bath for one hour. The mixture is then extracted with ether, the extract dried (MgSO₄) and concentrated to an oil. Distillation of the oil in vacuo affords 2-methyl-2-(2,5-dimethoxyphenyl)-5-phenyl-3-pentanone.

The thus-produced pentanone (58 g.) is dissolved in ethanol (400 ml.) and treated with sodium borohydride (10 g.) at room temperature. The reaction mixture is stirred for 12 hours and is then cooled and neutralized with 6 N hydrochloric acid. The ethanol is removed under reduced pressure and the residue extracted with ether. The extract is dried (MgSO₄) and concentrated to give 2-methyl-2-(2,5-dimethoxyphenyl)-5-phenyl-3-pentanol.

The pentanol (16 g.) is taken up in ether (100 ml.) and reacted with powdered potassium (2.5 g.) in ether (200 ml.). Carbon disulfide (equimolar to the potassium) is added and the mixture stirred for a half hour. Methyl iodide (9.0 g.) is then added and the reaction mixture stirred for 6 hours. The resulting suspension is filtered and the filtrate concentrated under reduced pressure. The residue is taken up in ethanol (150 ml.), Raney nickel added (25 g.) and the mixture refluxed for 18 hours. Evaporation of the alcohol and distillation of the residue gives 2-methyl-2-(2,5-dimethoxyphenyl)-5-phenyl-3-pentene.

The pentene derivative is catalytically hydrogenated according to the procedure of Preparation D and the resulting 2-methyl-2-(2,5-dimethoxyphenyl)-5-phenyl-3-pentane demethylated via the procedure of Preparation C to give the product.

PREPARATION F

2,5-Dibenzyloxyacetophenone

Over a period of 1.5 hours, methyl lithium (531 ml. of a 2 molar solution, 1.06 M) is added under a nitrogen atmosphere to a rapidly stirring solution of 2,5-dibenzyloxybenzoic acid (175 g., 0.532 M) in ether (250 ml.) tetrahydrofuran (1400 ml.) maintained at 15°–20° C. After stirring an additional 0.75 hour at 10°–15° C., water (600 ml.) is slowly added keeping the reaction temperature below 20° C. The aqueous layer is separated and extracted with ether (3×250 ml.). The organic phases are combined, washed with saturated sodium chloride solution (4×300 ml.), dried over sodium sulfate, and concentrated under vacuum to give the desired product.

PREPARATION G

Ethyl 3-(2,5-Dibenzyloxyphenyl)crotonate (Wittig Reaction)

A mixture of 2,5-dibenzyloxyacetophenone (43.2 g., 0.13 mole) and carbethoxymethylenetriphenylphosphorane (90.5 g., 0.26 mole) is heated under a nitrogen atmosphere at 170° C. for 4 hours. The clear melt is cooled to room temperature, triturated with ether and the precipitate of triphenyl phosphine oxide removed by filtration. The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives a residue which is purified by crystallization.

In like manner, ethyl 3-(2,5-dimethoxyphenyl)crotonate is prepared from 2,5-dimethoxyacetophenone (51.7 g.) and carbethoxymethylene triphenylphosphorane (200 g.).

PREPARATION H 3-(2,5-Dibenzyloxyphenyl)-1-butanol

A solution of ethyl 3-(2,5-dibenzyloxyphenyl)crotonate (24.1 g., 60 mM) in ether (250 ml.) is added to a mixture of lithium aluminum hydride (3.42 g., 90 mM) and ether (250 ml.). Aluminum chloride (0.18 g., 1.35 mM) is added and the mixture refluxed for 12 hours and then cooled. Water (3.4 ml.), sodium hydroxide (3.4 ml. of 6 N) and water (10 ml.) are then added successively to the reaction mixture. The inorganic salts which precipitate are filtered off and the filtrate is then concentrated in vacuo to give the desired alcohol.

In like manner, ethyl 3-(2,5-dimethoxyphenyl)crotonate is reduced to 3-(2,5-dimethoxyphenyl)butanol.

PREPARATION I 3-(2,5-Dibenzyloxyphenyl)butyl Tosylate

Tosyl chloride (11.1 g., 58.1 mM) is added to a solution of 3-(2,5-dibenzyloxyphenyl)-1-butanol (20.7 g., 57 mM) in pyridine (90 ml.) at −45° C. The reaction mixture is held at −35° C. for 18 hours and is then diluted with cold 2 N hydrochloric acid (1500 ml.) and extracted with ether (5×250 ml.). The combined extracts are washed with saturated sodium chloride solution (4×250 ml.) and then dried ($Na_2SO_4$). Concentration of the dried extract affords the product which may be purified by standard methods, if desired.

PREPARATION J 3-(2,5-Dibenzyloxyphenyl)-1-phenoxybutane

A solution of phenol (4.56 g., 48.6 mM) in dimethylformamide (40 ml.) is added under a nitrogen atmosphere to a suspension of sodium hydride (2.32 g., 48.6 mM of 50% previously washed with pentane) in dimethylformamide (70 ml.) at 60° C. The reaction mixture is stirred for one hour at 60°–70° C., after which a solution of 3-(2,5-dibenzyloxyphenyl)butyl tosylate (23.93 g., 46.3 mM) in dimethylformamide (80 ml.) is added. The reaction mixture is stirred at 80° C. for a half hour and is then cooled to room temperature, diluted with cold water (2500 ml.) and extracted with ether (4×400 ml.). The combined extracts are washed successively with cold 2 N hydrochloric acid (2×300 ml.) and saturated sodium chloride solution (3×300 ml.) and then dried ($Na_2SO_4$). Removal of the solvent under reduced pressure affords the product as an oil. The oily residue is dissolved in benzene and filtered through silica gel (100 g.). Concentration of the filtrate under reduced pressure gives the product.

Repetition of Procedures G through J, but using the 2,5-dibenzyloxy derivatives of benzaldehyde, acetophenone or propiophenone, the appropriate carbethoxy (or carbomethoxy) alkylidene triphenyl phosphorane; and the appropriate alcohol, phenol, thiophenol, hydroxypyridine or hydroxypiperidine as reactants affords the following compounds:

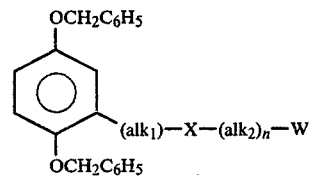

For convenience, the various values of W for given values of —(alk$_1$)—X—(alk$_2$)$_n$— are collectively tabulated.

| alk$_1$ | X | 2 | n | W |
|---|---|---|---|---|
| (CH$_2$)$_3$ | O | — | 0 | C$_6$H$_5$, 4-FC$_6$H$_4$, C$_4$H$_7$, 4-ClC$_6$H$_4$,C$_6$H$_{11}$, 4-pyridyl, 3-pyridyl, 4-(C$_6$H$_5$)C$_6$H$_{10}$, 4-piperidyl, CH$_3$, 4-(4-FC$_6$H$_4$)C$_6$H$_{10}$. |
| (CH$_2$)$_3$ | O | CH$_2$ | 1 | C$_6$H$_5$, 4-FC$_6$H$_4$, C$_6$H$_{11}$, 4-piperidyl, CH$_3$. |
| (CH$_2$)$_3$ | O | (CH$_2$)$_2$ | 1 | C$_6$H$_5$, CH$_3$, 4-ClC$_6$H$_4$, 4-pyridyl. |
| (CH$_2$)$_3$ | O | CH(CH$_3$) | 1 | C$_6$H$_5$, 4-FC$_6$H$_4$, CH$_3$, 4-piperidyl, 2-pyridyl. |
| (CH$_2$)$_3$ | O | CH(CH$_3$)(CH$_2$)$_2$ | 1 | C$_6$H$_5$, 4-pyridyl, CH$_3$. |
| CH(CH$_3$)(CH$_2$)$_2$ | O | — | 0 | C$_6$H$_5$, 4-FC$_6$H$_4$, C$_6$H$_{11}$, C$_3$H$_5$, 4-pyridyl, C$_7$H$_{13}$, 3-piperidyl, CH$_3$. 4-(C$_6$H$_5$)C$_6$H$_{10}$, 2-(4-ClC$_6$H$_4$)C$_4$H$_6$. |
| CH(CH$_3$)(CH$_2$)$_2$ | O | CH$_2$ | 1 | C$_6$H$_5$, 4-FC$_6$H$_4$, 4-piperidyl, 2-piperidyl, CH$_3$. |
| CH(CH$_3$)(CH$_2$)$_2$ | O | (CH$_2$)$_2$ | 1 | C$_6$H$_5$, 4-FC$_6$H$_4$, 4-pyridyl, 4-piperidyl, CH$_3$, C$_5$H$_9$. |
| CH(CH$_3$)(CH$_2$)$_2$ | O | (CH$_2$)$_4$ | 1 | C$_6$H$_5$, 4-pyridyl, 2-piperidyl, CH$_3$, 4-(C$_6$H$_5$)C$_6$H$_{10}$. |
| CH(CH$_3$)(CH$_2$)$_2$ | O | (CH$_2$)$_2$CH(CH$_3$) | 1 | C$_6$H$_5$, 4-FC$_6$H$_4$, CH$_3$, C$_3$H$_5$. |
| CH(CH$_3$)(CH$_2$)$_2$ | O | CH(CH$_3$) | 1 | C$_6$H$_5$, 4-ClC$_6$H$_4$, CH$_3$, 3-piperidyl, C$_7$H$_{13}$. |
| CH(CH$_3$)(CH$_2$)$_2$ | O | CH$_2$CH(C$_2$H$_5$) | 1 | C$_6$H$_5$, CH$_3$, C$_6$H$_{11}$. |
| CH(C$_2$H$_5$)(CH$_2$)$_2$ | O | — | 0 | C$_6$H$_5$, 4-FC$_6$H$_4$, 2-pyridyl, CH$_3$, 4-piperidyl, C$_3$H$_5$, 2-(4-FC$_6$H$_4$)C$_7$H$_{12}$. |
| CH(C$_2$H$_5$)(CH$_2$)$_2$ | O | (CH$_2$)$_2$ | 1 | C$_6$H$_5$, 4-FC$_6$H$_4$, 4-pyridyl, C$_6$H$_{11}$, 2-piperidyl, CH$_3$. |
| CH(C$_2$H$_5$)(CH$_2$)$_2$ | O | (CH$_2$)$_4$ | 1 | C$_6$H$_5$, 4-FC$_6$H$_4$, 4-pyridyl, C$_3$H$_5$, C$_5$H$_9$. |

-continued

| alk₁ | X | Z | n | W |
|---|---|---|---|---|
| CH(C₂H₅)(CH₂)₂ | O | CH(CH₃) | 1 | C₆H₅, 4-FC₆H₄, CH₃, 2-pyridyl, 4-piperidyl, C₆H₁₁. |
| CH(C₂H₅)(CH₂)₂ | O | (CH₂)₂CH(CH₃) | 1 | C₆H₅, 4-FC₆H₄, C₇H₁₃. |
| (CH₂)₄ | O | — | 0 | C₆H₅, 4-FC₆H₄, 4-ClC₆H₄, 4-pyridyl, C₄H₇, 2-piperidyl, CH₃. |
| (CH₂)₄ | O | CH₂ | 1 | C₆H₅, 4-FC₆H₄, 4-pyridyl, 3-pyridyl, 4-piperidyl, CH₃, C₆H₁₁. |
| (CH₂)₄ | O | CH₂CH(CH₃) | 1 | C₆H₅, 4-FC₆H₄, 4-(C₆H₅)C₆H₁₀. |
| (CH₂)₄ | O | CH(CH₃)CH₂ | 1 | C₆H₅, CH₃, 2-pyridyl, 3-piperidyl, 4-piperidyl, 4-FC₆H₄. |
| (CH₂)₄ | O | (CH₂)₅ | 1 | C₆H₅, 4-pyridyl, 3-piperidyl, 4-ClC₆H₄. |
| (CH₂)₃ | S | — | 0 | C₆H₅, 4-FC₆H₄, 4-ClC₆H₄, 4-pyridyl, 2-pyridyl, 2-piperidyl, 4-piperidyl, CH₃, C₃H₅, C₅H₉, C₆H₁₁, 4-(ClC₆H₄)C₆H₁₀. |
| (CH₂)₃ | S | CH₂ | 1 | C₆H₅, 4-FC₆H₄, CH₃, 2-pyridyl, 4-pyridyl, 3-piperidyl, C₅H₉. |
| (CH₂)₃ | S | (CH₂)₂ | 1 | C₆H₅, 4-ClC₆H₄, 4-pyridyl, CH₃, C₃H₅. |
| (CH₂)₃ | S | (CH₂)₄ | 1 | C₆H₅, 4-FC₆H₄, 4-pyridyl, CH₃, 4-piperidyl, C₆H₁₁. |
| CH(CH₃)(CH₂)₂ | S | — | 0 | C₆H₅, 4-FC₆H₄, C₆H₁₁, CH₃, 4-pyridyl, 3-pyridyl, 4-piperidyl, C₃H₇, 4-(C₆H₅)C₆H₁₀. |
| CH(CH₃)(CH₂)₂ | S | CH₂ | 1 | C₆H₅, 4-FC₆H₄, CH₃, 2-pyridyl. |
| CH(CH₃)(CH₂)₂ | S | (CH₂)₂ | 1 | C₆H₅, 4-ClC₆H₄, CH₃, 4-pyridyl, 3-piperidyl. |
| CH(CH₃)(CH₂)₂ | S | (CH₂)₄ | 1 | C₆H₅, CH₃, 4-pyridyl. |
| CH(C₂H₅)(CH₂)₂ | S | — | 0 | C₆H₅, 4-FC₆H₄, 4-(C₆H₅)C₆H₁₀, 4-pyridyl, 3-pyridyl, 2-piperidyl, C₆H₁₁. |
| CH(C₂H₅)(CH₂)₂ | S | CH(CH₃) | 1 | C₆H₅, 4-ClC₆H₄, CH₃, 4-piperidyl. |
| CH(C₂H₅)(CH₂)₂ | S | (CH₂)₂CH(CH₃) | 1 | C₆H₅, CH₃, 4-pyridyl. |
| CH(CH₃)(CH₂)₃ | O | — | 0 | C₆H₅, CH₃, 4-FC₆H₄, 4-pyridyl, C₃H₅, C₇H₁₃, 2-(4-FC₆H₄)C₅H₈. |
| CH(CH₃)(CH₂)₃ | O | (CH₂)₂ | 1 | C₆H₅, CH₃, 3-pyridyl, 4-piperidyl, C₆H₁₁. |
| CH(CH₃)(CH₂)₃ | S | — | 0 | C₆H₅, CH₃, 4-ClC₆H₄, 2-pyridyl, C₆H₁₁, 3-(4-ClC₆H₄)C₆H₁₀. |
| CH(CH₃)(CH₂)₃ | S | (CH₂)₄ | 1 | CH₃, C₆H₅, 4-FC₆H₄, 4-pyridyl. |

PREPARATION K

3-(2,5-Dihydroxyphenyl)-1-phenoxybutane

A solution of 3-(2,5-dibenzyloxyphenyl)-1-phenoxybutane (14.7 g., 133.5 mM) in a mixture of ethyl acetate (110 ml.), ethanol (110 ml.) and concentrated hydrochloric acid (0.7 ml.) is hydrogenated for 2 hours under 60 p.s.i. hydrogen in the presence of 10% palladium-on-carbon (1.5 g.). Removal of the catalyst by filtration and concentration of the filtrate gives an oil. The oil is purified by chromatography on silica gel (100 g.) and eluting with benzene-ethyl acetate consisting of 0–10% ethyl acetate. The middle fractions are combined and concentrated to give the title product.

In like manner, the remaining ethers (X=O) of Preparation J are debenzylated to afford the corresponding 2,5-dihydroxy derivatives.

The thio ethers are debenzylated by treatment with trifluoroacetic acid. The procedure comprises stirring a solution of the dibenzyl ether (X=S) in trifluoroacetic acid at room temperature for two hours. The reaction mixture is evaporated to dryness and the residue taken up in ether. The ether solution is washed with water, dried (MgSO₄) and evaporated to give the debenzylated compound.

PREPARATION L

1-Bromo-3-(2,5-Dimethoxyphenyl)butane

A solution of phosphorous tribromide (5.7 ml., 0.06 mole) in ether (30 ml.) is added to a solution of 3-(2,5-dimethoxyphenyl)-1-butanol (30.0 g., 0.143 mole) in ether (20 ml.) at −5° C. to −10° C. and the reaction mixture stirred at −5° C. to −10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.), saturated sodium chloride solution (1×50 ml.) and dried (Na₂SO₄). Removal of the ether and vacuum distillation of the residue affords the title compound.

The following compounds are prepared from 2,5-dimethoxybenzaldehyde, 2,5-dimethoxyacetopheone and 2,5-dimethoxypropiophenone and the appropriate carbethoxyalkylidene triphenylphosphorane by the procedures of Preparations G, H and L.

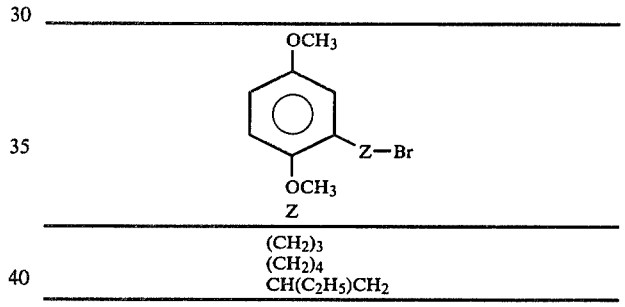

| Z |
|---|
| (CH₂)₃ |
| (CH₂)₄ |
| CH(C₂H₅)CH₂ |

PREPARATION M

4-(2,5-Dihydroxyphenyl)-1-(4-pyridyl)pentane

A mixture of 3-(2,5-dimethoxyphenyl)butyl triphenylphosphonium bromide (19.0 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°–5° C. Following completion of addition, the mixture is stirred for one hour at 0°–5° and then concentrated under reduced pressure. The concentrate is diluted with water (200 ml.) and then acidified with 6 N HCl. The aqueous acid solution is extracted with benzene (4×50 ml.). It is then made basic and extracted with ethyl acetate (3×50 ml.). Evaporation of the combined extracts after drying (MgSO₄) affords 4-(2,5-dimethoxyphenyl)-1-(4-pyridyl)-1-pentene.

Catalytic hydrogenation of the thus-produced pentene derivative according to the procedure given in Preparation D gives 4-(2,5-dimethoxyphenyl)-1-(4-pyridyl)pentane.

The pentane derivative thus obtained is demethylated by heating a mixture of the compound (7.15 g., 25 mmoles) and pyridine hydrochloride (35 g.) under a nitrogen atmosphere at 210° C. for 8 hours. The hot mixture is poured into water (40 ml.) and the resulting solution made basic with 6 N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel.

The 3-(2,5-dimethoxyphenyl)butyltriphenylphosphonium bromide is prepared by refluxing a mixture of 1-bromo-3-(2,5-dimethoxyphenyl)butane (21.5 g., 78.5 mmoles) and triphenyl phosphine (20.5 g., 78.5 mmoles) in xylene (60 ml.) for 18 hours. The reaction mixture is then cooled to room temperature and filtered. The filter cake is washed with ether and dried in a vacuum desicator to give the desired product.

Repetition of this procedure but using the appropriate bromo-(2,5-dimethoxyphenyl)alkane and the appropriate aldehyde or ketone affords the following compounds.

![structure with OH groups at 1,3 positions and Z—W substituent]

| Z | W* |
|---|---|
| (CH$_2$)$_3$ | 2-pyridyl |
| (CH$_2$)$_3$ | 3-pyridyl |
| (CH$_2$)$_3$ | 4-pyridyl |
| (CH$_2$)$_3$ | 2-piperidyl |
| (CH$_2$)$_3$ | 4-piperidyl |
| (CH$_2$)$_4$ | 2-pyridyl |
| (CH$_2$)$_4$ | 4-pyridyl |
| (CH$_2$)$_4$ | 3-piperidyl |
| (CH$_2$)$_4$ | 4-piperidyl |
| CH$_2$CH(CH$_3$)CH$_2$ | 2-pyridyl |
| CH$_2$CH(CH$_3$)CH$_2$ | 4-piperidyl |
| CH(CH$_3$)CH(CH$_3$)CH$_2$ | 3-pyridyl |
| CH(CH$_3$)CH(CH$_3$)CH$_2$ | 4-pyridyl |
| CH(CH$_3$)CH(CH$_3$)CH$_2$ | 3-piperidyl |
| CH(CH$_3$)(CH$_2$)$_2$ | 2-pyridyl |
| CH(CH$_3$)(CH$_2$)$_2$ | 3-pyridyl |
| CH(CH$_3$)(CH$_2$)$_2$ | 4-piperidyl |
| CH(CH$_3$)(CH$_2$)$_3$ | 3-pyridyl |
| CH(CH$_3$)(CH$_2$)$_3$ | 4-piperidyl |
| CH(CH$_3$)CH(C$_2$H$_5$)CH$_2$ | 4-pyridyl |
| CH(C$_2$H$_5$)(CH$_2$)$_2$ | 4-pyridyl |
| CH(C$_2$H$_5$)(CH$_2$)$_2$ | 2-piperidyl |
| CH(C$_2$H$_5$)(CH$_2$)$_2$ | 4-piperidyl |
| CH$_2$CH(C$_2$H$_5$)CH$_2$ | 3-pyridyl |
| CH(C$_2$H$_5$)(CH$_2$)$_3$ | 3-pyridyl |
| CH(C$_2$H$_5$)(CH$_2$)$_3$ | 4-piperidyl |
| CH(C$_2$H$_5$)CH(CH$_3$)CH$_2$ | 2-pyridyl |
| CH(C$_2$H$_5$)CH(C$_2$H$_5$)CH$_2$ | 4-pyridyl |
| CH(C$_2$H$_5$)CH(C$_2$H$_5$)CH$_2$ | 2-piperidyl |
| (CH$_2$)$_3$ | C$_6$H$_{11}$ |
| CH(CH$_3$)(CH$_2$)$_3$ | C$_6$H$_{11}$ |
| (CH$_2$)$_4$ | C$_3$H$_5$ |
| (CH$_2$)$_2$ | C$_4$H$_7$ |
| CH$_2$CH(CH$_3$)CH$_2$ | C$_5$H$_9$ |
| CH(CH$_3$)(CH$_2$)$_2$ | C$_7$H$_{13}$ |
| CH(CH$_3$)CH(CH$_3$)CH$_2$ | C$_6$H$_{11}$ |
| (CH$_2$)$_6$ | C$_6$H$_5$ |
| (CH$_2$)$_7$ | C$_6$H$_5$ |
| (CH$_2$)$_8$ | C$_6$H$_5$ |
| CH(CH$_3$)(CH$_2$)$_6$ | C$_6$H$_5$ |
| CH(CH$_3$)(CH$_2$)$_7$ | C$_6$H$_5$ |
| CH(CH$_3$)(CH$_2$)$_3$ | 4-FC$_6$H$_4$ |
| C(CH$_3$)$_2$(CH$_2$)$_3$ | C$_6$H$_5$ |
| CH(CH$_3$)(CH$_2$)$_3$ | 4-ClC$_6$H$_4$ |
| CH(CH$_3$)(CH$_2$)$_4$ | 4-ClC$_6$H$_4$ |
| CH(CH$_3$)(CH$_2$) | 4-ClC$_6$H$_4$ |
| CH(CH$_3$)(CH$_2$) | 4-FC$_6$H$_4$ |
| CH(CH$_3$)(CH$_2$)$_2$ | 4-FC$_6$H$_4$ |

-continued

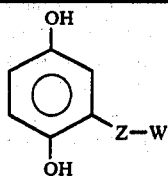

| Z | W* |
|---|---|
| CH(CH$_3$)(CH$_2$)$_2$ | 4-ClC$_6$H$_4$ |
| (CH$_2$)$_3$CH(CH$_3$) | C$_6$H$_{11}$ |
| CH(CH$_3$)(CH$_2$)$_2$CH(CH$_3$) | C$_6$H$_5$ |
| CH(CH$_3$)(CH$_2$)$_2$CH(CH$_3$) | C$_6$H$_{11}$ |
| CH(CH$_3$)(CH$_2$)$_2$CH(CH$_2$) | 4-piperidyl |
| CH(CH$_3$)(CH$_2$)$_3$ | C$_6$H$_{11}$ |
| (CH$_2$)$_3$ | C$_6$H$_{11}$ |
| (CH$_2$)$_4$ | C$_6$H$_{11}$ |
| (CH$_2$)$_8$ | C$_6$H$_{11}$ |

*C$_3$H$_5$ = cyclopropyl
C$_4$H$_7$ = cyclobutyl
C$_5$H$_9$ = cyclopentyl
C$_6$H$_{11}$ = cyclohexyl
C$_7$H$_{13}$ = cycloheptyl

PREPARATION N

2,5-Dimethoxy-α-methylstyrene Oxide

To a solution of dimethylsulfoxonium methylide (69.4 mM) in dimethyl sulfoxide (65 ml.) at room temperature is added solid 2,5-dimethoxyacetophenone (10 g., 55.5 mM). The reaction mixture is stirred for one hour at 25° C., for one-half hour at 50° C. and is then cooled. The mixture is diluted with water (50 ml.) and added to a mixture of ice water (200 ml.)—ether (250 ml.)—low boiling petroleum ether (25 ml.). The organic extract is washed twice with water (250 ml.), dried (MgSO$_4$) and evaporated to an oil. Fractional distillation of the oil yields 2,5-dimethoxy-α-methylstyrene oxide.

PREPARATION O

2-(2,5-Dimethoxyphenyl)-2-hydroxypropyl-2-phenylethyl Ether

A mixture of dry 2-phenylethanol (30 ml., 251 mM) and sodium metal (690 mg., 30 mM) is heated at 110° C. for 30 minutes. The resulting 1 M solution of sodium 2-phenylethoxide is cooled to 60° C., 2,5-dimethoxy-α-methylstyrene oxide (2 g., 10.3 mM) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. −65° C., 0.1 mm.) leaving a residue which is purified via column chromatography on silica gel 60 (300 g.) and eluted in 15 ml. fractions with ether-pentane. Fractions containing the title compound are combined and evaporated to dryness.

PREPARATION P

2-(2,5-Dimethoxyphenyl)propyl 2-Phenylethyl Ether

To a 0° C. solution of 2-(2,5-dimethoxyphenyl)-2-hydroxypropyl 2-phenylethyl ether (550 mg., 1.74 mM) in pyridine (2 ml.) is added dropwise phosphorous oxychloride (477 ml., 5.22 mM). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3 × 50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases, the reaction is filtered through diatomaceous earth and the filtrate evaporated to an oil. The oil is purified via preparative layer chromatography on silica gel plates, eluting with 6:1 pentane: ether to yield 2-(2,5-dimethoxyphenyl)propyl 2-phenylethyl ether.

PREPARATION Q 2-(2,5-Dihydroxyphenyl)propyl 2-Phenylethyl Ether

A mixture of 2-(2,5-dimethoxyphenyl)propyl 2-phenylethyl ether (195 mg., 0.65 mM), pyridine (0.4 ml., 4.96 mM) and dry pyridine hydrochloride (4 g., 34.6 mM) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to dryness. The residue is purified via preparative layer chromatography on silica gel plates by elution with ether-pentane.

The following compounds are prepared from appropriate alkanols by the methods of Procedures O, P, and Q.

[Structure: 2,5-dihydroxyphenyl group with -CH(CH₃)-CH₂-O-(alk₂)-W substituent]

| (alk₂) | W |
|---|---|
| —(CH₂)₆— | CH₃ |
| —(CH₂)₆ | C₆H₅ |
| —(CH₂)₄ | CH₃ |
| —CH(CH₃)CH₂ | CH₃ |
| —CH(CH₃)(CH₂)₄ | CH₃ |
| —(CH₂)— | 4-FC₆H₄ |
| —(CH₂)₂— | 4-pyridyl |
| —(CH₂)₂— | 2-piperidyl |
| —CH(CH₃)CH₂— | 4-piperidyl |
| —(CH₂)₂CH(CH₃)(CH₂)₂— | CH₃ |
| —CH(CH₃)— | CH₃ |
| —C(CH₃)₂— | CH₃ |

PREPARATION R 4-(2,5-Dihydroxyphenyl)-1-phenoxypentane

Under a nitrogen atmosphere a mixture of 2,5-dibenzyloxyacetophenone (50.0 g., 0.15 M) in tetrahydrofuran (175 ml.) and 3-phenoxypropyltriphenylphosphonium bromide (7.18 g., 0.15 M) in dimethylsulfoxide (450 ml.) is added dropwise over 1.75 hours to a suspension of 50% sodium hydride (7.89 g., 0.165 M) (previously washed with pentane) in tetrahydrofuran (75 ml.) maintained at 0°–5° C. After stirring for 4 hours at 0°–5° C. the reaction is allowed to warm to room temperature and is then carefully stirred into ice water (2000 ml.), acidified with concentrated hydrochloric acid, and extracted with ethyl acetate (5×400 ml.). The combined organic phases are washed with saturated sodium chloride solution (3×300 ml.), dried over sodium sulfate and concentrated under vacuum to yield an oil which is triturated with ether to precipitate triphenylphosphine oxide. Filtration, followed by concentration of the filtrate, gives an oily residue which is chromatographed over silica gel (1300 g.) eluting with benzene-hexane to obtain 4-(2,5-dibenzyloxyphenyl)-1-phenoxypent-3-ene.

A solution of 4-(2,5-dibenzyloxyphenyl)-1-phenoxypent-3-ene (51 g., 0.113 M) in a mixture of absolute ethanol (160 ml.), ethyl acetate (160 ml.) and concentrated hydrochloric acid (0.2 ml.) is hydrogenated for 12 hours under 55 lbs. hydrogen in the presence of 10% Pd/C. Removal of the catalyst by filtration and concentration of the filtrate under vacuum yields the desired product.

PREPARATION S 2,5-Dimethoxy-β-methylstyrene oxide

To a −78° C. solution of diphenylsulfonium ethylide (1.0 mole) in tetrahydrofuran (one liter) is slowly added 2,5-dimethoxybenzaldehyde (1.0 mole). The reaction mixture is stirred at −78° C. for 3 hours and then allowed to warm to room temperature. It is then added to ether-water and the ether phase separated. The ether phase is washed with water, dried (MgSO₄) and evaporated. Fractional distillation of the residue gives the title product.

PREPARATION T 3-(2,5-Dihydroxyphenyl)-2-propylbutyl Ether

To a solution of sodium butoxide in butanol (0.5 liters of 1 M) is added 2,5-dimethoxy-β-methylstyrene oxide (6.33 M). The mixture is heated for 18 hours a 70° C. and is then cooled and added to a mixture of ether-water. The ether solution is separated, dried (MgSO₄) and evaporated to give 3-(2,5-dimethoxyphenyl)-3-hydroxy-2-propylbutyl ether. It is purified by column chromatography on silica gel with ether-pentane elution.

By means of the procedures of Preparations P and Q, the title product is produced.

Similarly, the following are prepared from appropriate alcohols:

[Structure: 2,5-dihydroxyphenyl group with -CH₂-CH(CH₃)-O-(alk)₂-W substituent]

| (alk₂) | W | (alk₂) | W |
|---|---|---|---|
| CH₂ | CH₃ | CH(CH₃)CH₂ | CH₃ |
| (CH₂)₆ | CH₃ | CH(C₂H₅)—(CH₂)₂ | CH₃ |
| (CH₂)₃ | C₆H₅ | CH(CH₃)CH₂ | C₆H₅ |
| (CH₂)₂ | 4-FC₆H₄ | | |
| (CH₂)₂ | 4-pyridyl | | |

PREPARATION U (4-Halophenyl)cyclohexanols a. 3- and 4-(4-Fluorophenyl)cyclohexanols A benzene solution containing equimolar amounts of 4-fluorostyrene and 2-methoxybutadiene and hydroquinone (1% by weight based on diene) is heated in a sealed tube at 150° C. for 10 hours. The reaction vessel is cooled, the contents removed and concentrated to give 1-methoxy-4(and 5)-4-(fluorophenyl)cyclohexene which are separated by distillation in vacuo. Hydrolysis of the ether with 3% hydrochloric acid affords 3- and 4-(4-fluorophenyl)cyclohexanones.

Sodium borohydride reduction of the ketones according to the procedure of Example 7 affords the keto compounds.

In like manner, the corresponding 3- and 4-(4-chlorophenyl)cyclohexanols are prepared from 4-chlorostyrene.

b. 2-(4-Fluorophenyl)cyclohexanol

This compound is prepared from cyclohexane oxide and p-fluorophenyl lithium according to the procedure of Huitric et al., *J. Org. Chem.*, 27, 715–9 (1962), for preparing 2-(4-chlorophenyl)cyclohexanol.

PREPARATION V (2-Halophenyl)cycloalkanols

The procedure of Huitric et al., *J. Org. Chem.*, 27, 715–9 (1962) is employed but using the appropriate cycloalkylene oxide and p-halo (Cl or F) phenyl lithium reactants to produce the following compounds:

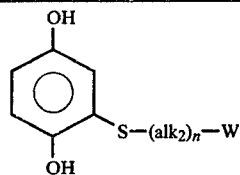

| a | Y  | a | Y |
|---|----|---|---|
| 2 | Cl | 2 | F |
| 3 | Cl | 3 | F |
| 5 | Cl | 5 | F |

PREPARATION W

Alkylation of 2,5-Dihydroxyphenylmercaptan

A solution of 2,5-dihydroxyphenylmercaptan (3.5 g., 0.01 mole) in absolute ethanol (50 ml.) is made just alkaline with sodium ethoxide. The appropriate bromide of formula Br-(alk$_2$)$_n$-W (0.01 mole) is added and the mixture refluxed for 3 hours. It is then concentrated under reduced pressure and the residue extracted with ether. Evaporation of the ether affords the product.

The following compounds are thus prepared:

| n | (alk$_2$) | W |
|---|-----------|---|
| 1 | —CH(CH$_3$)(CH$_2$)$_5$— | CH$_3$ |
| 1 | —CH(CH$_3$)CH(CH$_3$)(CH$_2$)$_4$— | CH$_3$ |
| 1 | —C(CH$_3$)$_2$(CH$_2$)$_5$— | CH$_3$ |
| 1 | —(CH$_2$)$_8$— | CH$_3$ |
| 1 | —(CH$_2$)$_4$— | CH$_3$ |
| 1 | —CH$_2$— | C$_6$H$_5$ |
| 1 | —(CH$_2$)— | C$_6$H$_5$ |
| 1 | —CH(CH$_3$)(CH$_2$)$_3$— | C$_6$H$_5$ |
| 1 | —CH$_2$— | C$_3$H$_5$ |
| 1 | —CH$_2$— | C$_5$H$_9$ |
| 1 | —CH$_2$— | C$_6$H$_{11}$ |
| 1 | —(CH$_2$)$_2$— | C$_5$H$_9$ |
| 1 | —(CH$_2$)$_3$— | C$_5$H$_9$ |
| 1 | —(CH$_2$)$_3$— | C$_6$H$_{11}$ |
| 1 | —(CH$_2$)$_4$— | C$_5$H$_9$ |
| 1 | —(CH$_2$)$_3$CH(C$_2$H$_5$)— | C$_6$H$_{11}$ |
| 1 | —(CH$_2$)$_7$— | C$_5$H$_9$ |
| 1 | —(CH$_2$)$_4$— | C$_7$H$_{13}$ |
| 1 | —(CH$_2$)$_2$— | C$_7$H$_{13}$ |
| 1 | —(CH$_2$)$_5$— | C$_4$H$_7$ |

-continued

| n | (alk$_2$) | W |
|---|-----------|---|
| 1 | —(CH$_2$)$_5$— | C$_3$H$_5$ |
| 1 | —(CH$_2$)— | 2-piperidyl |
| 1 | —(CH$_2$)$_3$— | 4-piperidyl |
| 1 | —(CH$_2$)— | 2-pyridyl |
| 1 | —(CH$_2$)$_3$— | 3-pyridyl |
| 1 | —(CH$_2$)$_4$— | 2-pyridyl |
| 1 | —CH(CH$_3$)(CH$_2$)$_2$— | 2-pyridyl |
| 1 | —CH(CH$_3$)(CH$_2$)$_3$— | 4-pyridyl |
| 1 | —CH(C$_2$H$_5$)(CH$_2$)$_2$— | 4-piperidyl |
| 1 | —(CH$_2$)$_4$— | 4-FC$_6$H$_4$ |
| 1 | —CH(CH$_3$)(CH$_2$)$_2$— | 4-ClC$_6$H$_4$ |
| 1 | —CH(CH$_3$)(CH$_2$)$_3$— | 4-FC$_6$H$_4$ |
| 0 | — | C$_6$H$_5$ |
| 0 | — | 4-FC$_6$H$_4$ |
| 0 | — | 4-ClC$_6$H$_4$ |
| 0 | — | C$_3$H$_5$ |
| 0 | — | C$_5$H$_9$ |
| 0 | — | C$_6$H$_{11}$ |
| 0 | — | C$_7$H$_{13}$ |
| 0 | — | 4-pyridyl |
| 0 | — | 2-piperidyl |
| 0 | — | 2-pyridyl |
| 0 | — | 2-(C$_6$H$_5$)C$_3$H$_4$ |
| 0 | — | 4-(C$_6$H$_5$)C$_6$H$_{10}$ |
| 0 | — | 3-(C$_6$H$_5$)C$_7$H$_{12}$ |
| 0 | — | CH$_3$ |

PREPARATION X dl-2-(2,5-Dibenzyloxyphenyl)-2-hydroxy-1-(2-phenylethoxy)propane To a 20° C. solution of dimethylsulfoxonium methylide (0.184 mole) in dimethylsulfoxide (185 ml.) is added 2,5-dibenzyloxyacetophenone (51.0 g., 0.153 mole). After stirring 1.5 hours at 20° C., the reaction is diluted with 200 ml. of ice water and added to 500 ml. ether and 200 ml. ice water. The organic phase is washed with cold water (2×200 ml.), dried over magnesium sulfate and evaporated to an oil. A solution of the thus produced crude 1-(2,5-dibenzyloxyphenyl)-1-methyloxirane (0.153 mole) in dimethylsulfoxide (100 ml.) is rapidly added to a 20° C. solution of sodium phenethoxide (0.306 mole) in dimethylsulfoxide (150 ml., made by the slow addition of 36.5 ml. [0.306 mole] of phenethanol to a slurry of 7.34 g. [0.306 mole] sodium hydride in 150 ml. dimethylsulfoxide). The reaction is slowly heated over a half-hour period to 70° C., stirred 30 minutes and cooled to 20° C. The reaction is diluted with 200 ml. ice water and added to ether (2 l.) and ice water (1 liter). The organic phase is washed with cold water (2×1 l.), dried over magnesium sulfate and evaporated to dryness. The residue is purified via column chromatography on 1.5 kg. of silica gel, and eluted with ether-pentane to yield dl-2-(2,5-dibenzyloxyphenyl)-2-hydroxy-1-(2-phenylethoxy)propane.

PREPARATION Y dl-2-(2,5-Dihydroxyphenyl)-1-(2-phenylethoxy)propane

To a 0° C. solution of dl-2-(2,5-dibenzyloxyphenyl)-2-hydroxy-1-(2-phenylethoxy)propane (29.0 g., 61.9 mmole) in pyridine (50 ml., 0.619 mole) is slowly added phosphorusoxy chloride (5.65 ml., 61.9 mmoles). The reaction is allowed to warm to 20° C. and is stirred at 20° C. for 20 hours. The reaction is added to a 0° C. solution of 3.3 N NaOH (300 ml.) and the resultant mixture extracted with ether (3×500 ml.). Each extract is washed with saturated potassium carbonate (1×500 ml.) and water (3×500 ml.). The combined organic extract is dried over magnesium sulfate, silica gel and then decolorized (carbon) and evaporated. The residue is purified via column chromatography on silica gel (200 g.) eluted with ether-pentane to yield an olefin mixture. To a solution of this mixture of olefins (3.62 g.) in ethanol (10 ml.) and ethyl acetate (10 ml.) is added solid sodium bicarbonate (300 mg.) and 10% Pd/C (1.2 g.). This mixture is stirred 6 hours under one atmosphere of hydrogen. The reaction is diluted with ethyl acetate and filtered through diatomaceous earth. The evaporated filtrate is purified via column chromatography on silica gel (200 g.) eluted with ether-pentane to yield dl-2-(3,5-dihydroxyphenyl)-1-(2-phenylethoxy)-propane.

PREPARATION Z

5-Phenyl-2-(2',5'-benzyloxy)phenoxypentane

A mixture of 5-phenyl-2-pentanol (16.4 g., 100 mM), triethylamine (28 ml., 200 mM) and dry tetrahydrofuran (80 ml.) under a nitrogen atmosphere is cooled in an ice/water bath. Methanesulfonyl chloride (8.5 ml., 110 mM) in dry tetrahydrofuran (20 ml.) is added dropwise at such a rate that the temperature holds essentially constant. The mixture is allowed to warm to room temperature and is then filtered to remove triethylamine hydrochloride. The filter cake is washed with dry tetrahydrofuran and the combined wash and filtrate evaporated under reduced pressure to give the product as an oil. The oil is dissolved in chloroform (100 ml.) and the solution washed with water (2×100 ml.) and then with saturated brine (1×20 ml.). Evaporation of the solvent affords 21.7 g. (89.7%) yield of 5-phenyl-2-pentanol mesylate which is used in the next step without further purification.

A mixture of 3.06 g. (10 mmoles) 2,5-bis(benzyloxy)-phenol (prepared by the procedure of U.S. Pat. No. 3,419,600), 2.76 g. (20 mmoles) of potassium carbonate, 10 ml. of N,N-dimethylformamide and 2.64 g. (11 mmoles) 5-phenyl-2-pentanol mesylate is heated under a nitrogen atmosphere at 80°–82° C. for 1.75 hours. The mixture is cooled to room temperature and then poured into ice/water (100 ml.). The aqueous solution is extracted with ethyl acetate (2×25 ml.) and the combined extracts washed successively with water (3×25 ml.) and saturated brine (1×25 ml.). The extract is then dried (MgSO₄), decolorized with charcoal and evaporated to give the desired product.

PREPARATION AA

5-Phenyl-2-(2',5'-dihydroxyphenoxy)pentane

5-Phenyl-2-(2',5'-benzyloxy)phenoxypentane is hydrogenated by the procedure of Preparation K to obtain the title compound.

The following compounds are prepared from the appropriate alkanol and 2,5-bis(benzyloxy)phenol by the procedures of Preparations Z followed by hydrogenation as described above.

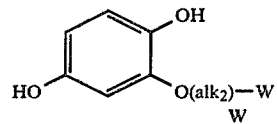

| alk₂ | W |
|---|---|
| CH₂C(CH₃)₃(CH₂)₄ | CH₃ |
| (CH₂)₉ | C₆H₅ |
| (CH₂)₉ | CH₃ |
| CH(CH₃)CH₂ | 2-pyridyl |
| (CH₂)₂ | 4-pyridyl |
| (CH₂)₃ | 2-piperidyl |
| (CH₂)₃ | 4-FC₆H₄ |
| CH(CH₃)(CH₂)₂ | 4-piperidyl |
| CH(CH₃)(CH₂)₂ | 4-ClC₆H₄ |
| CH₂ | C₆H₅ |
| CH₂ | 4-FC₆H₄ |
| — | C₆H₅ |
| — | cyclopropyl |
| — | cyclopentyl |
| — | cyclohexyl |
| — | cycloheptyl |
| — | 2-(C₆H₅)C₃H₄ |
| — | 3-(C₆H₅)C₇H₁₂ |
| — | 4-pyridyl |
| — | 4-piperidyl |
| CH₂ | CH₃ |
| (CH₂)₃ | CH₃ |
| (CH₂)₆ | CH₃ |
| C(CH₃)₂(CH₂)₅ | CH₃ |

PREPARATION BB 2-(2'-Hydroxy-5'-aminophenyl)-5-phenylpentane 40.0 ml. of concentrated ammonia (sp. gr. 0.90) is cooled in ice and sulfur dioxide gas is passed in until 10.0 g. of the gas has been absorbed. To the resulting solution is added 25.6 g. (0.10 mole) of 2-(2',5'-dihydroxyphenyl)-5-phenylpentane and the mixture is heated in an autoclave at 170°–190° C. for 16 hours. After cooling, the reaction mixture is acidified with hydrochloric acid, filtered to remove insoluble material, extracted with ethyl ether and the extracts discarded. The aqueous layer is made alkaline by addition of sodium hydroxide and extracted with chloroform. The organic extracts are evaporated to dryness to provide the crude product, which may be purified by column chromatography on silica gel, if desired.

By employing the appropriate ZW-substituted hydroquinone as starting material in place of 2-(2',5'-dihydroxyphenyl)-5-phenylpentane the following ZW-substituted p-aminophenols are similarly provided.

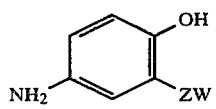

| Z | W |
|---|---|
| —CH(CH₃)(CH₂)₃ | C₆H₅ |
| —CH(CH₃)(CH₂)₃— | C₆H₅ |
| —CH(CH₃)CH₂— | cyclopropyl |
| —(CH₂)₃— | 2-pyridyl |
| —CH₂CH(CH₃)CH₂— | 4-piperidyl |
| —CH(CH₃)(CH₂)₇— | C₆H₅ |
| —CH(CH₃)(CH₂)₃— | 4-FC₆H₄ |
| —CH(CH₃)(CH₂)₄— | 4-ClC₆H₄ |
| —CH(CH₃)(CH₂)₂— | cycloheptyl |
| —(CH₂)₃O— | 4-(C₆H₅)C₆H₁₀ |
| —(CH₂)₃O— | CH₃ |
| —(CH₂)₃OCH₂— | 4-piperidyl |
| —CH(CH₃)(CH₂)₂O— | 2-(4-ClC₆H₄)C₄H₆ |
| —(CH₂)₄O— | CH₃ |

-continued

| Z | W |
|---|---|
| —(CH$_2$)$_4$O— | 4-ClC$_6$H$_4$ |
| —(CH$_2$)$_4$O(CH$_2$)$_5$— | 4-ClC$_6$H$_4$ |
| —(CH$_2$)$_3$S— | C$_6$H$_5$ |
| —(CH$_2$)$_3$S—CH$_2$— | C$_6$H$_5$ |
| —CH(CH$_3$)(CH$_2$)$_2$S— | cyclopropyl |
| —CH(CH$_3$)(CH$_2$)$_2$SCH$_2$— | C$_6$H$_5$ |
| —CH(CH$_3$)(CH$_2$)$_3$S(CH$_2$)$_4$— | C$_6$H$_5$ |
| —SCH$_2$— | C$_6$H$_5$ |
| —S(CH$_2$)$_5$— | cyclohexyl |
| —S— | C$_6$H$_5$ |
| —S— | cyclohexyl |
| —S— | CH$_3$ |

What is claimed is:

1. A compound of the formula

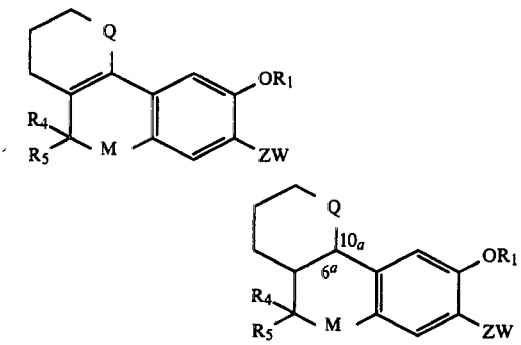

wherein Q is a member selected from the group consisting of CH$_2$, C=O CHOH and CHCH$_2$OH;

M is O or NR$_6$ wherein

R$_6$ is a member selected from the group consisting of hydrogen, —(CH$_2$)$_y$-carboalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms, C$_6$H$_5$—(CH$_2$)$_x$-wherein x is an integer from one to four and C$_6$H$_5$—(CH$_2$)$_{x-1}$CO—;

R$_1$ is hydrogen, alkanoyl having from one to five carbon atoms or —CO—(CH$_2$)$_p$-NR$_2$R$_3$ wherein p is 0 or an integer from 1 to 4; each of R$_2$ and R$_3$ when taken individually is hydrogen or alkyl having from one to four carbon atoms; R$_2$ and R$_3$ when taken together with the nitrogen to which they are attached form a 5- or 6-membered heterocyclic ring selected from piperidino, pyrrolo, pyrrolidino, morpholino and N-alkylpiperazino having from one to four carbon atoms in the alkyl group;

each of R$_4$ and R$_5$ is hydrogen, or unbranched alkyl having from one to four carbon atoms;

Z is (a) alkylene having from one to nine carbon atoms;

(b) -(alk$_1$)$_m$-X-(alk$_2$)$_n$- wherein each of (alk$_1$) and (alk$_2$) is alkylene having from one to nine carbon atoms, with the proviso that the summation of carbon atoms in (alk$_1$) plus (alk$_2$) is not greater than nine;

each of m and n is 0 or 1;

X is O, S, SO, or SO$_2$;

W is methyl, phenyl, p-chlorophenyl, p-fluorophenyl, pyridyl, piperidyl, cycloalkyl having from three to seven carbon atoms, or monosubstituted cycloalkyl wherein the substituent is phenyl, p-chlorophenyl or fluorophenyl; and the pharmaceutically acceptable acid addition salts of said compounds containing a basic amino group;

with the proviso that when W is methyl, Z is —(alk$_1$)$_m$—X—(alk$_2$)$_n$—.

2. A compound according to claim 1, formula (I).

3. A compound according to claim 2 wherein Q is CH$_2$.

4. A compound according to claim 3 wherein R$_1$ is hydrogen and M is 0 or NR$_6$ where R$_6$ is hydrogen or alkyl having from one to six carbon atoms.

5. A compound according to claim 4 wherein M is 0.

6. The compound according to claim 5 wherein R$_4$ and R$_5$ are each methyl, Z is CH(CH$_3$)CH$_2$CH$_2$CH$_2$ and W is phenyl.

7. A compound according to claim 2 wherein Q is C=O.

8. A compound according to claim 7 wherein R$_1$ is hydrogen and M is 0 or NR$_6$ where R$_6$ is hydrogen or alkyl having from one to six carbon atoms.

9. A compound according to claim 2 wherein Q is CHOH.

10. A compound according to claim 9 wherein M is 0, R$_4$ and R$_5$ are each methyl, Z is CH(CH$_3$)CH$_2$CH$_2$CH$_2$ and W is phenyl.

11. The compound according to claim 10 wherein R$_1$ is hydrogen and said hydroxy group in Q is in the α-configuration.

12. A compound according to claim 1, formula (II).

13. A compound according to claim 12, wherein Q is C=O.

14. A compound according to claim 13 wherein R$_1$ is hydrogen and M is 0 or NR$_6$ where R$_6$ is hydrogen or alkyl having from one to six carbon atoms.

15. A compound according to claim 14 wherein M is 0, R$_4$ and R$_5$ are each methyl, Z is CH(CH$_3$)CH$_2$CH$_2$CH$_2$ and W is phenyl.

16. The compound according to claim 15 wherein the hydrogen atoms in the 6a and 10a positions are in a cis relationship.

17. A compound according to claim 12 wherein Q is CHOH.

18. A compound according to claim 17 wherein M is 0, R$_4$ and R$_5$ are each methyl, Z is CH(CH$_3$)CH$_2$CH$_2$CH$_2$ and W is phenyl.

19. The compound according to claim 18 wherein R$_1$ is hydrogen and the hydrogen atoms in the 6a and 10a positions are in a cis- relationship.

20. A process for producing analgesia in a mammal which comprises orally or parenterally administering to the mammal an analgesic producing quantity of a compound of the formula

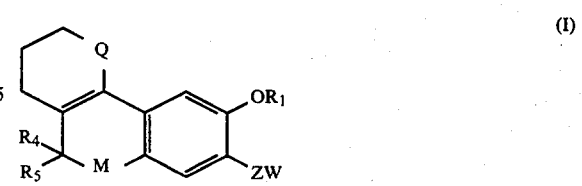

-continued (II)

[Chemical structure showing a bicyclic compound with Q, $10^a$, $OR_1$, $R_4$, $6^a$, $R_5$, M, and ZW substituents]

wherein Q is a member selected from the group consisting of $CH_2$, C=O, CHOH and $CHCH_2OH$;

M is O or $NR_6$ wherein $R_6$ is a member selected from the group consisting of hydrogen, —$(CH_2)_y$— carboalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms, $C_6H_5$—$(CH_2)_x$— wherein x is an integer from one to four and $C_6H_5$—$(CH_2)_{x-1}$—CO—;

$R_1$ is hydrogen, alkanoyl having from one to five carbon atoms or —CO—$(CH_2)_p$—$NR_2R_3$ wherein p is 0 or an integer from 1 to 4; each of $R_2$ and $R_3$ when taken individually is hydrogen or alkyl having from one to four carbon atoms; $R_2$ and $R_3$ when taken together with the nitrogen to which they are attached form a 5- or 6-membered heterocyclic ring selected from piperidino, pyrrolo, pyrrolidino, morpholino and N-alkylpiperazino having from one to four carbon atoms in the alkyl group;

each of $R_4$ and $R_5$ is hydrogen, or unbranched alkyl having from one to four carbon atoms;

Z is (a) alkylene having from one to nine carbon atoms;

(b) —$(alk_1)_m$—X—$(alk_2)_n$— wherein each of $(alk_1)$ and $(alk_2)$ is alkylene having from one to nine carbon atoms, with the proviso that the summation of carbon atoms in $(alk_1)$ plus $(alk_2)$ is not greater than nine;

each of m and n is 0 or 1;

X is O, S, SO or $SO_2$;

W is methyl, phenyl, p-chlorophenyl, p-fluorophenyl, pyridyl, piperidyl, cycloalkyl having from three to seven carbon atoms, or monosubstituted cycloalkyl wherein the substituent is phenyl, p-chlorophenyl or p-fluorophenyl; and the pharmaceutically acceptable acid addition salts of said compounds containing a basic amino group;

with the proviso that when W is methyl, Z is —$(alk_1)_m$—X—$(alk_2)_n$—.

21. A process according to claim 20 wherein said compound is of formula (I).

22. A process according to claim 21 wherein Q is $CH_2$.

23. A process according to claim 22 wherein M is O, $R_4$ and $R_5$ are each methyl, Z is $CH(CH_3)CH_2CH_2CH_2$ and W is phenyl.

24. The process according to claim 23 wherein $R_1$ is hydrogen.

25. The process according to claim 21 wherein Q is CHOH.

26. A process according to claim 25 wherein M is O, $R_4$ and $R_5$ are each methyl, Z is $CH(CH_3)CH_2CH_2CH_2$, W is phenyl and said hydroxy group in Q is in the α-configuration.

27. The process according to claim 26 wherein $R_1$ is hydrogen.

28. A process according to claim 20 wherein said compound is of formula (II).

29. A process according to claim 28 wherein Q is C=O.

30. A process according to claim 29 wherein M is O, $R_4$ and $R_5$ are each methyl, Z is $CH(CH_3)CH_2CH_2CH_2$, W is phenyl and the hydrogen atoms in the 6a and 10a positions are in a cis-relationship.

31. The process according to claim 30 wherein $R_1$ is hydrogen.

32. A process according to claim 28 wherein Q is CHOH.

33. A process according to claim 32 wherein M is O, $R_4$ and $R_5$ are each methyl, Z is $CH(CH_3)CH_2CH_2CH_2$, W is phenyl and the hydrogen atoms in the 6a and 10a positions are in a cis-relationship.

34. A process according to claim 33 wherein $R_1$ is hydrogen.

35. A pharmaceutical composition active as in analgesic comprising a pharmaceutically acceptable carrier and an analgesia producing amount of a compound of claim 1.

* * * * *

UNITED STATES PATENT AND TRADEMARK OFFICE
CERTIFICATE OF CORRECTION

PATENT NO. : 4,206,225

DATED : June 3, 1980

INVENTOR(S) : Michael R. Johnson

It is certified that error appears in the above-identified patent and that said Letters Patent are hereby corrected as shown below:

Column 1, line 47, " $\Delta^{6a(10A)}$ " should read -- $\Delta^{6a(10a)}$ --.

Column 4, lines 1 - 2, correct the spelling of "configuration"

Column 5, line 6, that portion of the formula reading

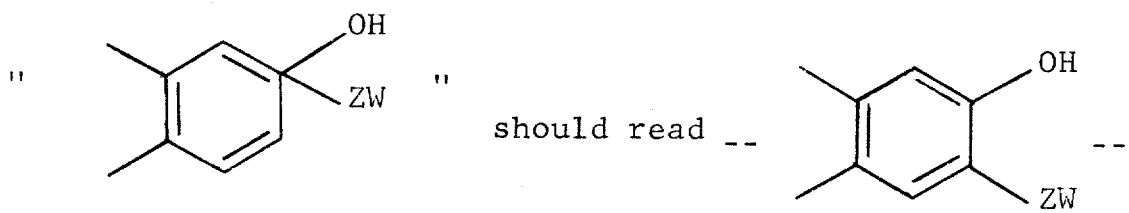

Column 11, line 48, correct the spelling of "previously".

Column 13, lines 2 and 3, correct the spelling of "mixture".

UNITED STATES PATENT AND TRADEMARK OFFICE
CERTIFICATE OF CORRECTION

PATENT NO. : 4,206,225
DATED : June 3, 1980
INVENTOR(S) : Michael R. Johnson

It is certified that error appears in the above-identified patent and that said Letters Patent are hereby corrected as shown below:

Column 21, line 45, "V" should read --$Y_1$--.

Column 25, line 15, "$MPE_550$" should read --$MPE_{50}$--.

Column 25, line 19, "Bendassett" should read --Benbasset--.

Column 45, line 1, insert "EXAMPLE 18".

Column 54, line 45, in the structural formula, "$C_6H_7$" should read --$C_6H_5$--.

Signed and Sealed this

Twenty-seventh Day of January 1981

[SEAL]

Attest:

RENE D. TEGTMEYER

Attesting Officer     Acting Commissioner of Patents and Trademarks